(12) United States Patent
Dolle et al.

(10) Patent No.: US 7,671,052 B2
(45) Date of Patent: Mar. 2, 2010

(54) PHENYL DERIVATIVES AND METHODS OF USE

(75) Inventors: Roland E. Dolle, King of Prussia, PA (US); Karin Worm, East Windsor, NJ (US); Q. Jean Zhou, Malvern, PA (US)

(73) Assignee: Adolor Corporation, Exton, PA (US)

( * ) Notice: Subject to any disclaimer, the term of this patent is extended or adjusted under 35 U.S.C. 154(b) by 1012 days.

(21) Appl. No.: 11/242,318

(22) Filed: Oct. 3, 2005

(65) Prior Publication Data

US 2006/0074086 A1 Apr. 6, 2006

Related U.S. Application Data

(60) Provisional application No. 60/616,024, filed on Oct. 5, 2004.

(51) Int. Cl.
  *A61K 31/535* (2006.01)
  *A61K 31/17* (2006.01)
  *C07D 265/30* (2006.01)
  *C07D 211/78* (2006.01)
  *C07C 275/00* (2006.01)

(52) U.S. Cl. .................. 514/237.5; 514/595; 544/176; 546/316; 564/56

(58) Field of Classification Search .............. 514/237.5, 514/595; 544/176; 546/316; 564/56
See application file for complete search history.

(56) References Cited

U.S. PATENT DOCUMENTS

| | | | | |
|---|---|---|---|---|
| 3,663,608 A | | 5/1972 | Holava et al. ............ | 260/501.1 |
| 4,055,664 A | * | 10/1977 | Skibbe ....................... | 514/654 |
| 2004/0087590 A1 | | 5/2004 | Makriyannis et al. .. | 514/252.03 |

FOREIGN PATENT DOCUMENTS

| EP | 0 020 018 B1 | 6/1983 |
|---|---|---|
| WO | WO 2004/017920 A2 | 3/2004 |
| WO | WO 2004/060882 A1 | 7/2004 |

OTHER PUBLICATIONS

Abad, J.L., et al., "Synthesis of dideuterated and enantiomers of monodeuterated tridecanoic acids at C-9 and C-10 positions," *J. Org. Chem.*, 2000, 65, 8582-8588.
Chen, J., et al., "The hydroboration of 3-butenyl derivatives with 9-borabicyclo[3.3.1]nonane," *J. Organomet. Chem.*, 1978, 156, 213-219.
Cheng, Y.-C., et al., "Relationship between the inhibition constant ($K_i$) and the concentration of inhibitor which causes 50 percent inhibition ($I_{50}$) of an enzymatic reaction," *Biochem. Pharmacol.*, 1973, 22, 3099-3108.
Chaikin, S.W., et al., "Reduction of aldehydes, ketones and acid chlorides by sodium borohydride," *J. Am. Chem. Soc.*, 1949, 71, 122-125.
Compton, D.R., "Cannabinoid behaviors: specific versus nonspecific actions," *Marijuana: An International Research Report*, 1987, 7, 213-218.
DeLean, A.P., et al., "Simultaneous analysis of families of sigmoidal curves: application to bioassay, radioligand assay, and physiological dose-response curves," *Am. J. Physiol.*, 1978, 235, E97-E102.
Dixon, W.J., "Efficient analysis of experimental observations," *Annul. Rev. Pharmacol. Toxicol.*, 1980, 20, 441-462.

Gill, E.W., et al., "Brain levels of $\Delta^1$-tetrahydrocannabinol and its metabolites in mice-correlation with behaviour, and the effect of the metabolic inhibitors SKF 525A and piperonyl butoxide," *Biochem. Pharmacol.*, 1972, 21, 2237-2248.
Gill, E.W., et al., "Preliminary experiments on the chemistry and pharmacology of cannabis," *Nature*, 1970, 228, 134-136.
Howlett, A.C., et al., "International union of pharmacology. XVII. Classification of cannabinoid receptors," *Pharmacological Reviews*, 2002, 54(2), 161-202.
Kim, S.H., et al., "An experimental model for peripheral neuropathy produced by segmental spinal nerve ligation in the rat," *Pain*, 1992, 50, 355-363.
LaBuda, C.J., et al., "Enhanced formalin nociceptive responses following L5 nerve ligation in the rat reveals neuropathy-induced inflammatory hyperalgesia," *Pain*, 2001, 94, 59-63.
LaBuda, C.J., et al., "Morphine and gabapentin decrease mechanical hyperalgesia and escape/avoidance behavior in a rat model of neuropathic pain," *Neurosci. Letts.*, 2000, 290, 137-140.
LaBuda, C.J., et al., "A behavioral test paradigm to measure the aversive quality of inflammatory and neuropathic pain in rats," *Exp. Neurol.*, 2000, 163, 490-494.
Little, P., et al., "Stereochemical Effects of 11-OH-$\Delta$8-THC-Dimethylheptyl in Mice and Dogs", *Pharmaology Biochemistry. & Behavior*, 1989, 32, 661-666.
Malan, T.P., Jr., et al., "$CB_2$ cannabinoid receptor agonists: pain relief without psychoactive effects?," *Curr. Op. Pharm.*, 2003, 3(1), 62-67.
Mechoulam, R., "Cannabinoids as therapeutic agents," *CRC Press*, Boca Raton, FL, 1986, 1-19.
Parolaro, D., "Presence and functional regulation of cannabinoid receptors in immune cells,"*Life Sci.*, 1999, 65(6/7), 637-644.
Pertwee, R.B., "Pharmacology of cannabinoid receptor ligands," *Current Medicinal Chem.*, 1999, 6, 635-664.
Pertwee, R.G., "The ring test: a quantitative method of assessing the 'cataleptic' effect of cannabis in mice," *Br. J. Pharmacology*, 1972, 46, 753-763.
Pertwee, R.G., "Cannabinoid receptors and pain," *Prog. Neurobiol.*, 2001, 63, 569-611.
Rice, A.S., "Cannabinoids and pain," *Curr. Opin. Investig. Drugs*, 2001, 2(3), 399-414.
Rinaldi-Carmona, M., et al., "SR 144528, the first potent and selective antagonist of the CB2 cannabinoid receptor," *J. of Pharmacology & Experimental Therapeutics*, 1998, 284(2), 644-650.

* cited by examiner

*Primary Examiner*—Rei-Tsang Shiao
*Assistant Examiner*—Joseph R Kosack
(74) *Attorney, Agent, or Firm*—Feldman Gale, P.A.; David A. Cherry

(57) ABSTRACT

Novel phenyl compounds, pharmaceutical compositions containing these compounds, and methods for their pharmaceutical use are disclosed. In certain embodiments, the compounds are agonists and/or ligands of cannabinoid receptors and may be useful, inter alia, for treating and/or preventing pain, gastrointestinal disorders, genitourinary disorders, inflammation, glaucoma, auto-immune diseases, ischemic conditions, immune-related disorders, and neurodegenerative diseases, for providing cardioprotection against ischemic and reperfusion effects, for inducing apoptosis in malignant cells, and as an appetite stimulant.

73 Claims, No Drawings

PHENYL DERIVATIVES AND METHODS OF USE

CROSS REFERENCE TO RELATED APPLICATION

This application claims the benefit of U.S. Provisional Application Ser. No. 60/616,024, filed Oct. 5, 2004, the disclosure of which is incorporated herein by reference in its entirety.

FIELD OF THE INVENTION

The present invention generally relates to novel phenyl compounds and the use thereof. More particularly, the present invention relates to novel phenyl compounds and their use, inter alia, as agonists of cannabinoid receptors.

BACKGROUND OF THE INVENTION

*Cannabis sativa* preparations have long been known as therapeutic agents to treat various diseases (Mechoulam, R., "Cannabinoids as Therapeutic Agents" CRC Press, Boca Raton, Fla. 1-19, 1986). The native active constituent, delta 9-tetrahydrocannabinol ($\Delta^9$-THC), is prescribed today, under the generic name dronabinol, as an anti-emetic and for enhancement of appetite, mainly in AIDS patients. However, separation between the clinically undesirable psychotropic effects and the therapeutically desirable effects on the peripheral nervous systems, the cardiovascular system, and the immune and endocrine systems is problematic. The discovery of two cannabinoid receptors, CB1 and CB2, has helped to elucidate the diverse cannabinoid effects.

The CB1 receptor has been cloned from rat, mouse, and human tissues and exhibits 97-99% amino acid sequence identity across species. The CB2 receptor exhibits 48% homology with the CB1 receptor (A. C. Howlett et al. *Pharmacological Reviews* 2002, 54, 161-202). The structures of both receptors are consistent with seven transmembrane G-protein coupled receptors. In addition, both receptors exert their effect by negative regulation of adenylyl cyclase activity through pertussis toxin-sensitive GTP-binding proteins. They were also shown to activate the mitogen activated protein kinase (MAPK) in certain cell types (Parolaro, D., *Life Sci.* 1999, 65, 637-44).

The CB1 receptor is expressed mainly in the central nervous system (CNS) and to a lesser extent in other tissues including, for example, gastrointestinal tissues, immune cells, reproductive organs, heart, lung, urinary bladder and adrenal gland. The CB2 receptor is expressed mostly in peripheral tissue associated with immune functions including, for example, macrophages, B, T cells and mast cells, as well as in peripheral nerve terminals (Pertwee, R. G., *Prog. Neurobiol.* 2001, 63, 569-611). The central distribution pattern of CB1 receptors accounts for several unwanted pharmacological properties of cannabinoids, such as impaired cognition and memory, altered control of motor function, and psychotropic and other neurobehavioral effects. CB1 receptors are also found on pain pathways in brain, spinal cord and at the peripheral terminals of primary sensory neurons (A. S. Rice, *Curr. Opin. Investig. Drugs* 2001 2 (3), 399-414). CB2 receptors have not been observed within the CNS.

CB1 knockout mice have been shown to be unresponsive to cannabinoids in behavioral assays providing molecular evidence that the psychotropic effects, including sedation, hallucinations and antinociception are manifested through the activation of the CB1 receptor that are present primarily in the CNS. Analysis of the CB2 knockout mouse has corroborated the evidence for the function of CB2 receptors in modulating the immune system. The CB2 receptor does not affect immune cell development and differentiation as determined by FACS analysis of cells from the spleen, lymph node and thymus from CB2 knockout mice. Further studies in these mice have shown that the immunosuppressive effects of $\Delta^9$-THC are mediated by the CB2 receptor.

Cannabinoid receptor agonists, such as CP55,940 and WIN 55,212-2, produce potent antinociception with equivalent efficacy to morphine in animal models of acute pain, persistent inflammatory pain, and neuropathic pain. They also induce a number of unwanted CNS side effects. Furthermore, the known cannabinoid receptor agonists are in general highly lipophilic and insoluble in water. Thus there is a need for cannabinoid receptor agonists with improved properties for the use as therapeutic agents.

Known CB1 cannabinoid receptor agonists produce a characteristic profile of in vivo effects in mice, including suppression of spontaneous activity, antinociception, hypothermia, and catalepsy. Measurement of these four properties, commonly referred to as the tetrad test, has played a key role in establishing the structure-activity relation of cannabinoids and cannabimimetics acting at CB1 receptors. Catalepsy in mice is indicative of CB1 activation and predictive of cannabinoid psychoactivity. Pertwee showed a correlation between catalepsy in the ring test in mice and the previously validated dog static ataxia model (R. G. Pertwee, *Br. J. Pharmacology* 1972, 46, 753-763). Therefore, catalepsy in mice is viewed as excellent predictor of CNS effects in humans (D. R. Compton, *Marijuana: An International Research Report* 7, 213-218, 1987; E. W. Gill and G. Jones, *Biochem. Pharmacol.* 21, 2237-2248, 1972; E. W. Gill et al. *Nature* 228, 134-136, 1970).

Efforts have been made to separate therapeutic effects from undesirable CNS side effects by increasing the selectivity for the CB2 receptor, thereby leading to efforts to design compounds with selectivity for the CB2 receptor over the CB1 receptor. These compounds would be predicted to lack side effects even if they penetrate the CNS because they would not activate the CB1 receptors in the CNS (Malan, T. Philip, Jr. et al., "CB2 cannabinoid receptor agonists: pain relief without psychoactive effects?", *Curr Op. Pharm.* 2003, 3 (1), 62-67; WO2004/017920).

There is considerable interest in developing new cannabimimetic compounds possessing preferentially high affinity for the CB2 receptor. Such compounds that preferentially stimulate the CB2 receptor, directly or indirectly, may provide clinically useful effects without major effects on the subject's central nervous system and can offer a rational therapeutic approach to a variety of disease states.

There is likewise considerable interest in developing new cannabimimetic compounds which selectively stimulate CB1 and/or CB2 receptors located in peripheral tissues and/or which do not cross the blood/brain barrier. Such compounds that preferentially stimulate peripheral CB1 and/or CB2 receptors, directly or indirectly, may provide clinically useful effects without major effects on the subject's central nervous system and may offer a rational therapeutic approach to a variety of disease states. The present invention is directed to these and other important ends.

SUMMARY OF THE INVENTION

Accordingly, the present invention is directed, in part, to novel phenyl compounds which may be agonists of cannabinoid receptors and which thus may be useful, inter alia, for the treatment of diseases or disorders which are associated with the cannabinoid receptor system.

Specifically, in one embodiment, the present invention relates to compounds of formula I:

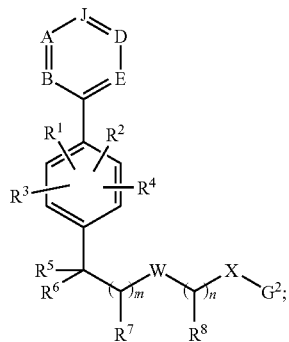

wherein:

$R^1$, $R^2$, $R^3$, and $R^4$ are each independently H, alkyl, $-OR^{9a}$, $-N(R^{10})(R^{11})$, $-C(=O)N(R^{12})(R^{13})$, $-C(=O)-OR^{9b}$, $-OP(=O)(OR^{9c})(OR^{9d})$, $-CN$, or

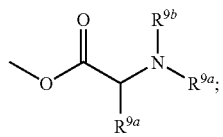

$R^5$ and $R^6$ are each independently H or alkyl, or taken together with the carbon atom to which they are attached form a 3- to 8-membered carbocyclic ring, wherein 1 to 3 of the ring carbon atoms independently may be optionally replaced by $-O-$, $-S-$, $-S(=O)-$, $-S(=O)_2-$, or $-N(R^{9e})-$;

each $R^7$ and $R^8$ is independently H, alkyl, halogen, or $-OR^{9f}$;

A, B, D, and E are each independently N, $CR^{14a}$, $C-[C(R^{15a})(R^{16a})]_p-N(R^{17})-G^1$, or $C-[C(R^{15b})(R^{16b})]_p-OC(=O)-N(R^{18a})(R^{18b})$;

J is N or $CR^{14b}$, provided that no more than two of A, B, D, E, and J are N;

each $G^1$ is independently $-S(=O)_2R^{19}$, $-S(=O)_2N(R^{20a})(R^{20b})$, $-C(=O)$-heterocycloalkyl, $-C(=O)$-heteroaryl, $-C(=O)-N(R^{18c})(R^{18d})$, $-C(=CHNO_2)-N(R^{18c})(R^{18d})$, or $-C(=N-CN)-N(R^{18e})(R^{18f})$;

$G^2$ is alkyl, acyl, aryl, heteroaryl, heterocycloalkyl, $-S(=O)_2R^{19}$, $-S(=O)_2N(R^{20a})(R^{20b})$, $-C(=O)$-heterocycloalkyl, $-C(=O)$-heteroaryl, $-C(=O)-N(R^{18c})(R^{18d})$, $-C(=O)-OR^{9b}$, $-C(=CHNO_2)-N(R^{18c})(R^{18d})$, or $-C(=N-CN)-N(R^{18e})(R^{18f})$;

each $R^{9a}$, $R^{9b}$, $R^{9c}$, $R^{9d}$, $R^{9e}$, and $R^{9f}$ is independently H or alkyl;

each $R^{10}$, $R^{11}$, $R^{12}$, and $R^{13}$ is independently H, alkyl, alkenyl, aryl, or heteroaryl, or each $R^{10}$ and $R^{11}$ or $R^{12}$ and $R^{13}$, taken together with the nitrogen atom to which they are attached, independently form a 4- to 8-membered heterocyclic ring wherein 1 or 2 of the ring carbon atoms independently may be optionally replaced by $-O-$, $-S-$, $-S(=O)-$, $-S(=O)_2-$, $-NH-$, $-N(alkyl)-$, $-N(C(=O)-R^{9a})-$, or $-N(S(=O)_2-R^{9a})-$;

each $R^{14a}$ and $R^{14b}$ is independently H, halogen, alkyl, $-CH_2F$, $-CHF_2$, $-CF_3$, $-CN$, $-(CH_2)_r-OH$, or $-(CH_2)_r-O$-alkyl;

each $R^{18a}$, $R^{18b}$, $R^{18c}$, $R^{18d}$, $R^{18e}$, $R^{18f}$, $R^{20a}$, and $R^{20b}$ is independently H, alkyl, alkenyl, or aryl, or each $R^{18a}$ and $R^{18b}$ or $R^{18c}$ and $R^{18d}$ or $R^{20a}$ and $R^{20b}$, taken together with the nitrogen atom to which they are attached independently form a 4- to 8-membered heterocyclic ring wherein 1 or 2 of the ring carbon atoms independently may be optionally replaced by $-O-$, $-S-$, $-S(=O)_2-$, $-NH-$, $-N(alkyl)-$, $-N(C(=O)-R^{9a})-$, or $-N(S(=O)_2-R^{9a})-$;

each $R^{19}$ is independently H, alkyl, aryl, OH, or $-O$-alkyl;

W is a single bond, $-O-$, $-S-$, $-CH_2-$, $-CF_2-$, alkylidene, $-CH(halogen)-$, $-CH(OH)-$, or $-CH(O-alkyl)-$, provided that when W is $-O-$ or $-S-$, then $n \geq 2$ and each $R^7$ and $R^8$ is independently H or alkyl;

X is a single bond, $-CH=CH-$, $-O-$, or $-N(R^{21})-$, provided that when X is $-O-$, $G^2$ is other than $-C(=N-CN)-N(R^{18e})(R^{18f})$; and provided that when X is $-O-$ or $-N(R^{21})-$, then $R^8$ is H or alkyl; and provided that when $G^2$ is $-C(=CHNO_2)-N(R^{18c})(R^{18d})$, then X is $-N(R^{21})-$; and provided that when $G^2$ is heterocycloalkyl or heteroaryl and attached to X through a ring heteroatom, then X is a single bond;

each $R^{15a}$, $R^{15b}$, $R^{16a}$, $R^{16b}$, $R^{17}$, and $R^{21}$ is independently H or alkyl; or $R^{17}$ and $R^{18c}$, taken together with the atoms through which they are connected form a 4- to 8-membered heterocyclic ring wherein 1 or 2 of the ring carbon atoms independently may be optionally replaced by $-O-$, $-S-$, $-S(=O)-$, $-S(=O)_2-$, $-NH-$, $-N(alkyl)-$, $-N(C(=O)-R^{9a})-$, or $-N(S(=O)_2-R^{9a})-$; or $R^{18c}$ and $R^{21}$, taken together with the atoms through which they are connected form a 4- to 8-membered heterocyclic ring wherein 1 or 2 of the ring carbon atoms independently may be optionally replaced by $-O-$, $-S-$, $-S(=O)-$, $-S(=O)_2-$, $-NH-$, $-N(alkyl)-$, $-N(C(=O)-R^{9a})-$, or $-N(S(=O)_2-alkyl)-$;

m and n are each independently an integer from 1 to 5;
each p is independently an integer from 0 to 5; and
each r is independently an integer from 0 to 4;

with the proviso that:
at least one of A, B, D, and E is $C-[C(R^{15a})(R^{16a})]_p-N(R^{17})-G^1$ or $C-[C(R^{15b})(R^{16b})]_p-OC(=O)-N(R^{18a})(R^{18b})$;

or a pharmaceutically acceptable salt thereof.

The present invention is also directed, in part, to pharmaceutical compositions comprising a pharmaceutically acceptable carrier and at least one compound of formula I.

The present invention is also directed, in part, to methods of binding cannabinoid receptors in a patient in need thereof, comprising the step of administering to a patient an effective amount of and at least one compound of formula I. In preferred form, the present cannabinoid receptor agonists may be used in methods for the treatment or prevention of a disease or disorder selected from the group consisting of pain, gastrointestinal disorders, genitourinary disorders, inflammation, glaucoma, auto-immune diseases, ischemic conditions, immune-related disorders, and neurodegenerative diseases, and combinations thereof. In alternate embodiments, the present cannabinoid receptor agonists may be used in the methods for providing cardioprotection against ischemic and reperfusion effects, for inducing apoptosis in malignant cells, and for appetite modulation.

These and other aspects of the invention will become more apparent from the present specification and claims.

DETAILED DESCRIPTION OF ILLUSTRATIVE EMBODIMENTS

The present invention is generally directed to phenyl compounds, their use, inter alia, as agonists of cannabinoid receptors, pharmaceutical compositions containing these compounds, and methods of their pharmaceutical use.

As employed above and throughout the disclosure, the following terms, unless otherwise indicated, shall be understood to have the following meanings.

As used herein, "compounds of formula I" collectively refers to compounds of formula I, IIa, and IIIb, or any combination thereof.

As used herein, "alkyl" refers to an optionally substituted, saturated straight, or branched, hydrocarbon radical having from about 1 to about 20 carbon atoms (and all combinations and subcombinations of ranges and specific numbers of carbon atoms therein). Alkyl groups include, but are not limited to, methyl, ethyl, n-propyl, isopropyl, n-butyl, isobutyl, t-butyl, n-pentyl, isopentyl, neopentyl, n-hexyl, isohexyl, 3-methylpentyl, 2,2-dimethylbutyl, and 2,3-dimethylbutyl.

As used herein, "alkenyl" refers to an optionally substituted alkyl group having from about 2 to about 10 carbon atoms and one or more double bonds (and all combinations and subcombinations of ranges and specific numbers of carbon atoms therein), wherein alkyl is as previously defined.

As used herein, "acyl" refers to an alkyl-C(=O)— group, wherein alkyl is as previously defined.

As used herein, "alkylene" refers to an optionally substituted bivalent alkyl radical having the general formula —$(CH_2)_n$—, where n is 1 to 10. Non-limiting examples include methylene, dimethylene, trimethylene, pentamethylene, and hexamethylene.

As used herein, "alkylidene" refers to an optionally substituted bivalent aliphatic radical derived from univalent aliphatic or cycloaliphatic hydrocarbon radicals whose names end in "yl" by removal of one of the hydrogen atoms from the carbon atom with the free valence, said radical having from about 1 to about 20 carbon atoms (and all combinations and subcombinations of ranges and specific numbers of carbon atoms therein). "Lower alkylidene" refers to those divalent aliphatic and cycloaliphatic groups with from about 1 to about 10 carbon atoms. Alkylidene groups include, but are not limited to, methylidene, ethylidene, n-propylidene, isopropylidene, cyclopropylidene, n-butylidene, isobutylidene, t-butylidene, 2-butenylidene, 2-butynylidene, n-pentylidene, cyclopentylidene, isopentylidene, neopentylidene, n-hexylidene, isohexylidene, cyclohexylidene, cyclooctylidene, adamantylidene, 3-methylidene pentylidene, 2,2-dimethylidene butylidene, and 2,3-dimethylbutylidene.

As used herein, "alkynyl" refers to an optionally substituted alkyl group having from about 2 to about 10 carbon atoms and one or more triple bonds (and all combinations and subcombinations of ranges and specific numbers of carbon atoms therein), wherein alkyl is as previously defined.

As used herein, "alkoxy" and "alkoxyl" refer to an optionally substituted alkyl-O-group wherein alkyl is as previously defined. Exemplary alkoxy and alkoxyl groups include methoxy, ethoxy, n-propoxy, i-propoxy, n-butoxy, and heptoxy.

As used herein, "aryl" and "aromatic" each refer to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

As used herein, "aralkyl" refers to an optionally substituted moiety composed of an alkyl radical bearing an aryl substituent and having from about 6 to about 50 carbon atoms (and all combinations and subcombinations of ranges and specific numbers of carbon atoms therein), with from about 6 to about 10 carbon atoms being preferred. Non-limiting examples include, for example, benzyl, diphenylmethyl, triphenylmethyl, phenylethyl, and diphenylethyl.

As used herein, "heteroaryl" refers to an optionally substituted aryl ring system wherein in at least one of the rings, one or more of the carbon atom ring members is independently replaced by a heteroatom group selected from the group consisting of S, O, N, and NH, wherein aryl is as previously defined. Heteroaryl groups having a total of from about 5 to about 14 carbon atom ring members and heteroatom ring members(and all combinations and subcombinations of ranges and specific numbers of carbon and heteroatom ring members) are preferred. Exemplary heteroaryl groups include, but are not limited to, pyrryl, furyl, pyridyl, pyridine-N-oxide, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl. Heteroaryl may be attached via a carbon or a heteroatom to the rest of the molecule.

As used herein, "cycloalkyl" or "carbocyclic ring" each refers to an optionally substituted, mono-, di-, tri-, or other multicyclic alicyclic ring system having from about 3 to about 20 carbon atoms (and all combinations and subcombinations of ranges and specific numbers of carbon atoms therein). In some preferred embodiments, the cycloalkyl groups have from about 3 to about 8 carbon atoms. Multi-ring structures may be bridged or fused ring structures, wherein the additional groups fused or bridged to the cycloalkyl ring may include optionally substituted cycloalkyl, aryl, heterocloalkyl, or heteroaryl rings. Exemplary cycloalkyl groups include, but are not limited to, cyclopropyl, cyclobutyl, cyclopentyl, cyclohexyl, cyclooctyl, adamantyl, 2-[4-isopropyl-1-methyl-7-oxa-bicyclo[2.2.1]heptanyl], and 2-[1,2,3,4-tetrahydro-naphthalenyl].

As used herein, "alkylcycloalkyl" refers to an optionally substituted ring system comprising a cycloalkyl group having one or more alkyl substituents, wherein cycloalkyl and alkyl are each as previously defined. Exemplary alkylcycloalkyl groups include, for example, 2-methylcyclohexyl, 3,3-dimethylcyclopentyl, trans-2,3-dimethylcyclooctyl, and 4-methyldecahydronaphthalenyl.

As used herein, "cycloalkylalkyl" refers to an optionally substituted ring comprising an alkyl radical having one or more cycloalkyl substituents, wherein cycloalkyl and alkyl are as previously defined. In some preferred embodiments, the alkyl moieties of the cycloalkylalkyl groups have from about 1 to about 3 carbon atoms. Exemplary cycloalkylalkyl groups include, but are not limited to, cyclohexylmethyl, 4-[4-methyldecahydronaphthalenyl]-pentyl, 3-[trans-2,3-dimethylcyclooctyl]-propyl, and cyclopentylethyl.

As used herein, "heteroaralkyl" and "heteroarylalkyl" each refers to an optionally substituted ring system comprising an alkyl radical bearing a heteroaryl substituent, having from about 2 to about 50 carbon atoms (and all combinations and subcombinations of ranges and specific numbers of carbon atoms therein), with from about 6 to about 25 carbon atoms being preferred. Non-limiting examples include 2-(1H-pyrrol-3-yl)ethyl, 3-pyridylmethyl, 5-(2H-tetrazolyl)methyl, and 3-(pyrimidin-2-yl)-2-methylcyclopentanyl.

As used herein, "heterocycloalkyl" and "heterocyclic ring" each refers to an optionally substituted ring system composed of a cycloalkyl radical wherein in at least one of the rings, one or more of the carbon atom ring members is independently replaced by a heteroatom group selected from the group consisting of O, S, N, and NH, wherein cycloalkyl is as previously defined. Heterocycloalkyl ring systems having a total of from about 5 to about 14 carbon atom ring members and heteroatom ring members (and all combinations and subcombinations of ranges and specific numbers of carbon and heteroatom ring members) are preferred. In other preferred embodiments, the heterocyclic groups may be fused to one or more aromatic rings. Heterocycloalkyl may be attached via a ring carbon or a ring heteroatom to the rest of the molecule. Exemplary heterocycloalkyl groups include, but are not limited to, azepanyl, tetrahydrofuranyl, hexahydropyrimidinyl, tetrahydrothienyl, piperidinyl, pyrrolidinyl, isoxazolidinyl, isothiazolidinyl, pyrazolidinyl, oxazolidinyl, thiazolidinyl, piperazinyl, 2-oxo-morpholinyl, morpholinyl, 2-oxo-piperidinyl, piperadinyl, decahydroquinolyl, octahydrochromenyl, octahydro-cyclopenta[c]pyranyl, 1,2,3,4,-tetrahydroquinolyl, 1,2,3,4-tetrahydroquinazolinyl, octahydro-[2]pyridinyl, decahydro-cycloocta[c]furanyl, 1,2,3,4-tetrahydroisoquinolyl, 2-oxo-imidazolidinyl, and imidazolidinyl. In some embodiments, two moieties attached to a heteroatom may be taken together to form a heterocycloalkyl ring, such as when $R^5$ and $R^6$, taken together with the nitrogen atom to which they are attached, form a heterocycloalkyl ring. In certain of these embodiments, 1 or 2 of the heterocycloalkyl ring carbon atoms may be replaced by other moieties which contain either one (—O—, —S—, —N($R^9$)—) or two (—N($R^{10}$)—C(═O)—, or —C(═O)—N($R^{10}$)—) ring replacement atoms. When a moiety containing one ring replacement atom replaces a ring carbon atom, the resultant ring, after replacement of a ring atom by the moiety, will contain the same number of ring atoms as the ring before ring atom replacement.

As used herein, the term "spiroalkyl" refers to an optionally substituted alkylene diradical, both ends of which are bonded to the same carbon atom of the parent group to form a spirocyclic group. The spirocyclic group, as herein defined, has 3 to 20 ring atoms, preferably with 3 to 10 ring atoms. Exemplary spiroalkyl groups taken together with its parent group include, but are not limited to, 1-(1-methyl-cyclopropyl)-propan-2-one, 2-(1-phenoxy-cyclopropyl)-ethylamine, and 1-methyl-spiro[4.7]dodecane.

As used herein, "halo" and "halogen" each refers to a fluoro, chloro, bromo, or iodo moiety, with fluoro or chloro being preferred.

Typically, substituted chemical moieties include one or more substituents that replace hydrogen. Exemplary substituents include, for example, halo (e.g., F, Cl, Br, I), alkyl, cycloalkyl, alkylcycloalkyl, cycloalkylalkyl, alkenyl, alkynyl, aralkyl, aryl, heteroaryl, heteroaralkyl, spiroalkyl, heterocycloalkyl, hydroxyl (—OH), nitro (—NO$_2$), cyano (—CN), amino (—NH$_2$), —N-substituted amino (—NHR"), —N,N-disubstituted amino (—N(R")R"), oxo (═O), carboxy (—COOH), —O—C(═O)R", alkoxycarbonyl (—C(═O)R"), —OR", —C(═O)OR", -(alkylene)-C(═O)—OR", —NHC(═O)R", aminocarbonyl (—C(═O)NH$_2$), —N-substituted aminocarbonyl (—C(═O)NHR"), —N,N-disubstituted aminocarbonyl (—C(═O)N(R")R"), thiol, thiolato (—SR"), sulfonic acid (—SO$_3$H), phosphonic acid (—PO$_3$H), —P(═O)(OR")OR", —S(═O)R", —S(═O)$_2$R", —S(═O)$_2$NH$_2$, —S(═O)$_2$ NHR", —S(═O)$_2$NR"R", —NHS(═O)$_2$R", —NR"S(═O)$_2$R", —CF$_3$, —CF$_2$CF$_3$, —NHC(═O)NHR", —NHC(═O)NR"R", —NR"C(═O)NHR", —NR"C(═O)NR"R", —NR"C(═O)R" and the like.

In relation to the aforementioned substituents, each moiety R" can be, independently, any of H, alkyl, cycloalkyl, alkenyl, aryl, aralkyl, heteroaryl, or heterocycloalkyl, or when two R" groups are attached to the same nitrogen atom within a substituent, as herein above defined, R" and R" can be taken together with the nitrogen atom to which they are attached to form a 3- to 8-membered heterocycloalkyl ring, wherein one or two of the heterocycloalkyl ring carbon atoms independently may be optionally replaced by —O—, —S—, —SO, —SO$_2$—, —NH—, —N(alkyl)-, —N(acyl)-, —N(aryl)-, or —N(aroyl)-groups, for example.

As used herein, "cannabinoid" refers to any one of a group of naturally occurring compounds of related structure that may be isolable from *Cannabis sativa*, more commonly known as marijuana, and structurally modified derivatives thereof. Cannabinoids include for example, compounds such as $\Delta^9$-tetrahydrocannabinol, $\Delta^8$-tetrahydrocannabinol, cannabichromene, cannabicyclol, cannabidiol, cannabielsoin, cannabigerol, cannabinol, cannabitriol, nabilone, and nantradol, and numerous structural variants. Typically cannabinoids are lipophilic in terms of their solubility.

As used herein, "cannabimimetic" refers to any of a group of endogenous or exogenous receptor ligands that bind one or more of the receptors bound by cannabinoids and mimic one or more behaviors of cannabinoids while so bound. Examples of endogenous cannabimimetics (also referred to as "endocannabinoids") produced in mammalian tissues include, for example, arachidonoylethanolamide (anandamide), 2-arachidonoyl glycerol, 1(3)-arachidonoyl glycerol, and palmitoylethanolamide. Examples of exogenous cannabimimetics include, for example WIN 55,212-2, CP 55,940, HU-210, and the like. Other examples of exogenous cannbimimetics may be found in publications such as R. B. Pertwee, "Pharmacology of Cannabinoid Receptor Ligands", Current Medicinal Chemistry, 1999, 6, 635-664, and A. C. Howlett, et al. "International Union of Pharmacology. XXVII. Classification of Cannabinoid Receptors", Pharmacological Reviews, 2002, 54(2), 161-202, the disclosures of which are each hereby incorporated herein by reference, in their entireties.

As used herein, "side effect" refers to a consequence other than the one(s) for which an agent or measure is used, as the adverse effects produced by a drug, especially on a tissue or organ system other then the one sought to be benefited by its administration. In the case, for example, of cannabinoids, the term "side effect" may refer to such conditions as, for example, psychotropic effects, such as confusion, anxiety, panic, distortion of perception, fantasizing, sedation, inner unrest, irritability and insomnia, sweating, rhinorrhoea, loose stools, hiccups, dry mouth, tachycardia, ataxia, dizziness, orthostatic hypotension, and anorexia.

As used herein, "effective amount" refers to an amount of a compound as described herein that may be therapeutically effective to inhibit, prevent or treat the symptoms of particular disease, disorder or side effect. Such diseases, disorders and side effects include, but are not limited to, those pathological conditions associated with the binding of cannabinoid receptors (for example, in connection with the treatment and/or prevention of pain), wherein the treatment or prevention comprises, for example, agonizing the activity thereof by contacting cells, tissues or receptors with compounds of the present invention. Thus, for example, the term "effective amount," when used in connection with cannabinoids, for example, for the treatment of pain, refers to the treatment and/or prevention of the painful condition. The term "effective amount", when used in connection with the present cannabinoid receptor agonist compounds, refers to the treatment, reduction and/or prevention of side effects typically associated with cannabinoids including, for example, such side effects as those hereinabove mentioned.

As used herein, "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, "in combination with", "combination therapy" and "combination products" refer, in certain embodiments, to the concurrent administration to a patient of cannabinoids and the compounds of the present invention. When administered in combination, each component may be administered at the same time or sequentially in any order at different points in time. Thus, each component may be administered separately but sufficiently closely in time so as to provide the desired therapeutic effect.

As used herein, "dosage unit" refers to physically discrete units suited as unitary dosages for the particular individual to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

As used herein, "hydrate" refers to a compound of the present invention which is associated with water in the molecular form, i.e., in which the H-OH bond is not split, and may be represented, for example, by the formula $R.H_2O$, where R is a compound of the invention. A given compound may form more than one hydrate including, for example, monohydrates ($R.H_2O$) or polyhydrates ($R.nH_2O$ wherein n is an integer >1) including, for example, dihydrates ($R.2H_2O$), trihydrates ($R.3H_2O$), and the like, or hemihydrates, such as, for example, $R.n_{1/2}H_2O$, $R.n_{1/3}H_2O$, $R.n_{1/4}H_2O$ and the like wherein n is an integer.

As used herein, "solvate" refers to a compound of the present invention which is associated with solvent in the molecular form, i.e., in which the solvent is coordinatively bound, and may be represented, for example, by the formula R.(solvent), where R is a compound of the invention. A given compound may form more than one solvate including, for example, monosolvates (R.(solvent)) or polysolvates (R.n(solvent)) wherein n is an integer >1) including, for example, disolvates (R.2(solvent)), trisolvates (R.3(solvent)), and the like, or hemisolvates, such as, for example, $R.n_{1/2}$(solvent), $R.n_{1/3}$(solvent), $R.n_{1/4}$(solvent) and the like wherein n is an integer. Solvents herein include mixed solvents, for example, methanol/water, and as such, the solvates may incorporate one or more solvents within the solvate.

As used herein, "acid hydrate" refers to a complex that may be formed through association of a compound having one or more base moieties with at least one compound having one or more acid moieties or through association of a compound having one or more acid moieties with at least one compound having one or more base moieties, said complex being further associated with water molecules so as to form a hydrate, wherein said hydrate is as previously defined and R represents the complex herein described above.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout may exist in alternate forms and such alternate forms are intended to be included within the scope of the compounds described and claimed in the present application. Accordingly, reference herein to compounds of formula I, IIa, and/or IIb is intended to include reference to these alternate forms. For example, many amino-containing compounds can be used or prepared as an acid addition salt. Often such salts improve isolation and handling properties of the compound. For example, depending on the reagents, reaction conditions, and the like, compounds as described herein can be used or prepared, for example, as their hydrochloride or tosylate salts. Alternate forms of the compounds described herein also include, for example, isomorphic crystalline forms, all chiral and racemic forms, including stereoisomeric and partial stereoisomeric forms, N-oxides, hydrates, solvates, and acid salt hydrates.

Certain acidic or basic compounds of the present invention may exist as zwitterions. All forms of the compounds, including free acid, free base and zwitterions, are contemplated to be within the scope of the present invention. It is well known in the art that compounds containing both amino and carboxy groups often exist in equilibrium with their zwitterionic forms. Thus, any of the compounds described herein throughout that contain, for example, both amino and carboxy groups, also include reference to their corresponding zwitterions.

As used herein, "patient" refers to animals, including mammals, preferably humans.

As used herein, "agonist" refers to a ligand that produces a conformational change in the receptor and alters the equilibrium of the receptor's active and inactive states, which in turn induces a series of events, resulting in a measurable biological response. Agonists include, for example, conventional agonists, which exhibit positive receptor activity, and inverse agonists, which exhibit a negative intrinsic activity.

As used herein, "prodrug" refers to compounds specifically designed to maximize the amount of active species that reaches the desired site of reaction, which are of themselves typically inactive or minimally active for the activity desired, but through biotransformation are converted into biologically active metabolites.

As used herein, "stereoisomers" refers to compounds that have identical chemical constitution, but differ as regards the arrangement of the atoms or groups in space.

As used herein, "partial stereoisomer" refers to stereoisomers having two or more chiral centers wherein at least one of the chiral centers has defined stereochemistry (i.e., R or S) and at least one has undefined stereochemistry (i.e., R or S). When the term "partial stereoisomers thereof" is used herein, it refers to any compound within the described genus whose configuration at chiral centers with defined stereochemistry centers is maintained and the configuration of each undefined chiral center is independently selected from R or S. For example, if a stereoisomer has three chiral centers and the stereochemical configuration of the first center is defined as having "S" stereochemistry, the term "or partial stereoisomer thereof" refers to stereoisomers having SRR, SRS, SSR, or SSS configurations at the three chiral centers, and mixtures thereof.

In addition, asymmetric carbon atoms may be introduced into the present compounds, including the compounds of formula I, depending on, for example, the chemical structure of the moiety A, B, D, or E, when $R^{15a}$ and $R^{16a}$ or $R^{15b}$ and $R^{16b}$ in the moiety $C-[C(R^{15a})(R^{16a})]_p-N(R^{17})-G^1$, or $C-[C(R^{15b})(R^{16b})]_p-OC(=O)-R(R^{18a})(R^{18b})$, are non-identical, and the independent selection of any variables contained therein. For example, when $R^{15a}$ is hydrogen and $R^{16a}$ is other than H, the carbon atom to which $R^{16a}$ is attached is asymmetric.

As used herein, "N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

When any variable occurs more than one time in any constituent or in any formula, its definition in each occurrence is independent of its definition at every other occurrence. Combinations of substituents and/or variables are permissible only if such combinations result in stable compounds.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form or to any specific optical or geometric isomer, except where such stereochemistry is clearly defined.

Accordingly, the present invention is directed, in part, to a new class of cannabinoid receptor modulator compounds, preferably phenyl compounds, which are highly useful in connection with the binding of cannabinoid receptors. Compounds binding cannabinoid receptors may act as agonists, inverse agonists, and/or antagonists toward the cannabinoid receptors. In situations where a cannabimimetic compound or ligand agonizes one or more cannabinoid receptors, the resultant binding is believed to trigger an event or series of events in the cell that results in a change in the cell's activity, its gene regulation, or the signals that it sends to neighboring cells, similar to that of a cannabinoid. Thus, in some embodiments, compounds of the invention may serve as preventatives or treatments of diseases or disorders in which cannabinoid receptors are implicated. In situations where a cannabimimetic compound or ligand antagonizes one or more cannabinoid receptors, the resultant binding typically occurs comparatively to a greater extent relative to that of the endogenous cannabinoid, but does not trigger one or more of the events of signal transduction. Compounds acting as inverse agonists are believed to bind more strongly to the inactive form of the receptor, thereby inhibiting the normal regulatory functions of the receptor and its endogenous regulatory ligands. Compounds with either inverse agonist or antagonist properties are highly useful, for example, in connection with the study of functions of cannabinoid receptors, which may result, for example, in the development of new cannabimimetic agonist compounds, such as those, for example, reported in Rinaldi-Carmona, M. et al., *Journal of Pharmacology and Experimental Therapeutics*, 1998, 284 (2), 644-650, the disclosure of which is hereby incorporated herein by reference, in its entirety.

In one embodiment, the present invention is directed to compounds of formula I:

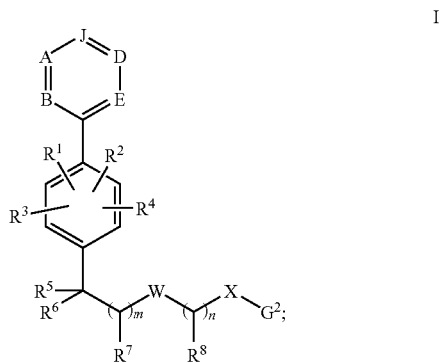

wherein:

$R^1$, $R^2$, $R^3$, and $R^4$ are each independently H, alkyl, $-OR^{9a}$, $-N(R^{10})(R^{11})$, $-C(=O)N(R^{12})(R^{13})$, $-C(=O)-OR^{9b}$, $-OP(=O)(OR^{9c})(OR^{9d})$, $-CN$, or

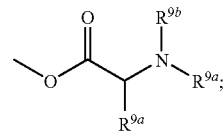

$R^5$ and $R^6$ are each independently H or alkyl, or taken together with the carbon atom to which they are attached form a 3- to 8-membered carbocyclic ring, wherein 1 to 3 of the ring carbon atoms independently may be optionally replaced by $-O-$, $-S-$, $-S(=O)-$, $-S(=O)_2-$, or $-N(R^{9e})-$;

each $R^7$ and $R^8$ is independently H, alkyl, halogen, or $-OR^{9f}$;

A, B, D, and E are each independently N, $CR^{14a}$, $C-[C(R^{5a})(R^{16a})]_p-N(R^{17})-G^1$, or $C-[C(R^{15b})(R^{16b})]_p-C(=O)-N(R^{18a})(R^{18b})$;

J is N or $CR^{14b}$, provided that no more than two of A, B, D, E, and J are N;

each $G^1$ is independently $-S(=O)_2R^{19}$, $-S(=O)_2N(R^{20a})(R^{20b})$, $-C(=O)$-heterocycloalkyl, $-C(=O)$-heteroaryl, $-C(=O)-N(R^{18c})(R^{18d})$, $-C(=CHNO_2)-N(R^{18c})(R^{18d})$, or $-C(=N-CN)-N(R^{18e})(R^{18f})$;

$G^2$ is alkyl, acyl, aryl, heteroaryl, heterocycloalkyl, $-S(=O)_2R^{19}$, $-S(=O)_2N(R^{21a})(R^{20b})$, $-C(=O)$-heterocycloalkyl, $-C(=O)$-heteroaryl, $-C(=O)-N(R^{18c})(R^{18d})$, $-C(=O)-OR^{9b}$, $-C(=CHNO_2)-N(R^{18c})(R^{18d})$, or $-C(=N-CN)-N(R^{18e})(R^{18f})$;

each $R^{9a}$, $R^{9b}$, $R^{9c}$, $R^{9d}$, $R^{9e}$, and $R^{9f}$ is independently H or alkyl;

each $R^{10}$, $R^{11}$, $R^{12}$, and $R^{13}$ is independently H, alkyl, alkenyl, aryl, or heteroaryl, or each $R^{10}$ and $R^{11}$ or $R^{12}$ and $R^{13}$, taken together with the nitrogen atom to which they are attached, independently form a 4- to 8-membered heterocyclic ring wherein 1 or 2 of the ring carbon atoms independently may be optionally replaced by —O—, —S—, —S(=O)—, —S(=O)$_2$—, —NH—, —N(alkyl)-, —N(C(=O)—R$^{9a}$)—, or —N(S(=O)$_2$—R$^{9a}$)—;

each $R^{14a}$ and $R^{14b}$ is independently H, halogen, alkyl, —CH$_2$F, —CHF$_2$, —CF$_3$, —CN, —(CH$_2$)$_r$—OH, or —(CH$_2$)$_r$—O-alkyl;

each $R^{18a}$, $R^{18b}$, $R^{18c}$, $R^{18d}$, $R^{18e}$, $R^{18f}$, $R^{20a}$, and $R^{20b}$ is independently H, alkyl, alkenyl, or aryl, or each $R^{18a}$ and $R^{18b}$ or $R^{18c}$ and $R^{18d}$ or $R^{20a}$ and $R^{20b}$, taken together with the nitrogen atom to which they are attached independently form a 4- to 8-membered heterocyclic ring wherein 1 or 2 of the ring carbon atoms independently may be optionally replaced by —O—, —S—, —S(=O)$_2$—, —NH—, —N(alkyl)-, —N(C(=O)—R$^{9a}$)—, or —N(S(=O)$_2$—R$^{9a}$)—;

each $R^{19}$ is independently H, alkyl, aryl, OH, or —O-alkyl;

W is a single bond, —O—, —S—, —CH$_2$—, —CF$_2$—, alkylidene, —CH(halogen)-, —CH(OH)—, or —CH(O-alkyl)-, provided that when W is —O— or —S—, then n≧2 and each $R^7$ and $R^8$ is independently H or alkyl;

X is a single bond, —CH=CH—, —O—, or —N(R$^{21}$)—, provided that when X is —O—, G$^2$ is other than —C(=N—CN)—N(R$^{18e}$)(R$^{18f}$); and provided that when X is —O— or —N(R$^{21}$)—, then R$^8$ is H or alkyl; and provided that when G$^2$ is —C(=CHNO$_2$)—N(R$^{18c}$)(R$^{18d}$), then X is —N(R$^{21}$)—; and provided that when G$^2$ is heterocycloalkyl or heteroaryl and attached to X through a ring heteroarom, then X is a single bond;

each $R^{15a}$, $R^{15b}$, $R^{16a}$, $R^{16b}$, $R^{17}$, and $R^{21}$ is independently H or alkyl; or $R^{17}$ and $R^{18c}$, taken together with the atoms through which they are connected form a 4- to 8-membered heterocyclic ring wherein 1 or 2 of the ring carbon atoms independently may be optionally replaced by —O—, —S—, —S(=O)—, —S(=O)$_2$—, —NH—, —N(alkyl)-, —N(C(=O)—R$^{9a}$)—, or —N(S(=O)$_2$—R$^{9a}$)—; or R$^{18c}$ and R$^{21}$, taken together with the atoms through which they are connected form a 4- to 8-membered heterocyclic ring wherein 1 or 2 of the ring carbon atoms independently may be optionally replaced by —O—, —S—, —S(=O)—, —S(=O)$_2$—, —NH—, —N(alkyl)-, —N(C(=O)—R$^{9a}$)—, or —N(S(=O)$_2$-alkyl)-;

m and n are each independently an integer from 1 to 5;

each p is independently an integer from 0 to 5; and each r is independently an integer from 0 to 4;

with the proviso that:

at least one of A, B, D, and E is C—[C(R$^{15a}$)(R$^{16a}$)]$_p$—N(R$^{17}$)-G$^1$ or C—[C(R$^{15b}$)(R$^{16b}$)]$_p$—OC(=O)—N(R$^{18a}$)(R$^{18b}$);

or a pharmaceutically acceptable salt thereof.

In some preferred embodiments, at least one of A, B, D, and E is independently C—[C(R$^{15a}$)(R$^{16a}$)]$_p$—N(R$^{17}$)-G$^1$.

In certain preferred embodiments, R$^1$, R$^2$, R$^3$ and R$^4$ are each independently H, —OR$^{9a}$, —N(R$^{10}$)(R$^{11}$), —C(=O)N(R$^{12}$)(R$^{13}$), —C(=O)—OR$^{9b}$, —OP(=O)(OR$^{9c}$)(OR$^{9d}$), —CN; or

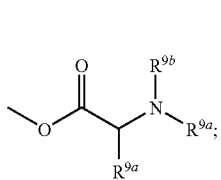

more preferably H, —OR$^{9a}$, —N(R$^{10}$)(R$^{11}$), —C(=O)N(R$^{12}$)(R$^{13}$), —C(=O)—OR$^{9b}$, —OP(=O)(OR$^{9c}$)(OR$^{9d}$), or —CN; still more preferably H, —N(R$^{10}$)(R$^{11}$), or —OR$^{9a}$, yet still more preferably H or —OR$^{9a}$. In some other preferred embodiments, at least two of R$^1$, R$^2$, R$^3$ and R$^4$ are H, more preferably three of R$^1$, R$^2$, R$^3$ and R$^4$ are H. In other preferred embodiments, R$^3$ and R$^4$ are each independently H or alkyl. Alternatively preferred, R$^1$, R$^2$, R$^3$ and R$^4$ are each independently-N(R$^{10}$)(R$^{11}$) or —OR$^{9a}$.

In preferred embodiments, R$^5$ and R$^6$ are each independently H or alkyl, more preferably H or C$_1$-C$_3$ alkyl, more preferably still H or methyl. In some more preferred embodiments, R$^5$ and R$^6$ taken together with the carbon atom to which they are attached form a 3- to 8-membered carbocyclic ring, wherein 1 to 3, more preferably 1, even more preferably none, of the ring carbon atoms independently may be optionally replaced by —O—, —S—, —S(=O)—, —S(=O)$_2$—, or —N(R$^{9e}$)—. In some other more preferred embodiments, R$^5$ and R$^6$ taken together with the carbon atom to which they are attached form a 3- to 6-membered carbocyclic ring, wherein 1, more preferably none, of the ring carbon atoms independently may be optionally replaced by —O—, —S—, —S(=O)—, —S(=O)$_2$—, or —N(R$^{9e}$)—. In other more preferred embodiments, R$^5$ and R$^6$ are both alkyl, more preferably still C$_1$-C$_3$ alkyl, even more preferably methyl.

In some preferred embodiments, each R$^7$ and R$^8$ is independently H or alkyl; more preferably still H or methyl; yet more preferably H.

In certain preferred embodiments, A, B, D, and E are each independently CR$^{14a}$, C—[C(R$^{15a}$)(R$^{16a}$)]$_p$—N(R$^{17}$)-G$^1$, or C—[C(R$^{15b}$)(R$^{16b}$)]$_p$—OC(=O)—N(R$^{18a}$)(R$^{18b}$); more preferably each independently CR$^{14a}$ or C—[C(R$^{15a}$)(R$^{16a}$)]$_p$—N(R$^{17}$)-G$^1$. In some alternatively preferred embodiments, one of A, B, D, and E is C—[C(R$^{15a}$)(R$^{16a}$)]$_p$—N(R$^{17}$)-G$^1$ or C—[C(R$^{15b}$)(R$^{16b}$)]$_p$—OC(=O)—N(R$^{18a}$)(R$^{18b}$), more preferably C—[C(R$^{15a}$)(R$^{16a}$)]$_p$—N(R$^{17}$)-G$^1$. In certain other preferred embodiments, one of A and D is C—[C(R$^{15a}$)(R$^{16a}$)]$_p$—N(R$^{17}$)-G$^1$, or C—[C(R$^{15b}$)(R$^{16b}$)]$_p$—OC(=O)—N(R$^{18a}$)(R$^{18b}$); more preferably CR$^{14a}$ or C—[C(R$^{15a}$)(R$^{16a}$)]$_p$—N(R$^{17}$)-G$^1$. In some other preferred embodiments, one of B and E is C—[C(R$^{15a}$)(R$^{16a}$)]$_p$—N(R$^{17}$)-G$^1$, or C—[C(R$^{15b}$)(R$^{16b}$)]$_p$—OC(=O)—N(R$^{18a}$)(R$^{18b}$); more preferably CR$^{14a}$ or C—[C(R$^{15a}$)(R$^{16a}$)]$_p$—N(R$^{17}$)-G$^1$. In yet other preferred embodiments, two or three of A, B, D, and E are each independently CR$^{14a}$. In yet other preferred embodiments, when A, B, D, and E are each other than C—CN, C—(CH$_2$)$_r$—OH, or C—(CH$_2$)$_r$—O-alkyl, then at least one of R$^1$, R$^2$, R$^3$ and R$^4$ is independently —OR$^{9a}$, —N(R$^{10}$)(R$^{11}$), —C(=O)N(R$^{12}$)(R$^{13}$), —C(=O)—OR$^{9b}$, —OP(=O)(OR$^{9c}$)(OR$^{9d}$), —CN, or

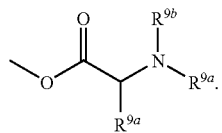

In some more preferred embodiments when A or B is other than C—CN, C—(CH$_2$)$_r$—OH, or C—(CH$_2$)$_r$—O-alkyl, then at least one, more preferably one, of R$^1$, R$^2$, R$^3$ and R$^4$ is independently —OR$^{9a}$, —N(R$^{10}$)(R$^{11}$), —C(=O)N(R$^{12}$)(R$^{13}$), —C(=O)—OR$^{9b}$, —OP(=O)(OR$^{9c}$)(OR$^{9d}$), or —CN.

In some preferred embodiments, J is CR$^{14b}$.

In other preferred embodiments, each G$^1$ is independently —S(=O)$_2$R$^{19}$, —S(=O)$_2$N(R$^{21a}$)(R$^{21b}$), —C(=O)-heterocycloalkyl, —C(=O)-heteroaryl, or —C(=O)—N(R$^{18c}$)(R$^{18d}$); still more preferably —S(=O)$_2$R$^{19}$, —C(=O)-heterocycloalkyl, —C(=O)-heteroaryl, —C(=O)—N(R$^{18c}$)(R$^{18d}$); yet more preferably —S(=O)$_2$R$^{19}$, —C(=O)-heterocycloalkyl, or —C(=O)—N(R$^{18c}$)(R$^{18d}$). In some preferred embodiments, G$^1$ is —C(=O)-heterocycloalkyl, more preferably wherein the heterocycloalkyl is tetrahydrofuran, morpholine, or pyrrolidinone, each optionally substituted. In other preferred embodiments, G$^1$ is —C(=O)-heteroaryl, more preferably wherein the heteroaryl is furan, oxazolyl, pyridinyl, pyridinyl-N-oxide, pyrazinyl, pyrrolyl, or thiadiazolyl, each optionally substituted. In other preferred embodiments, G$^1$ is —C(=O)-heteroaryl or —C(=O)—N(R$^{18c}$)(R$^{18d}$), more preferably —C(=O)—N(R$^{18c}$)(R$^{18d}$). In still other preferred embodiments, each G$^1$ is independently —S(=O)$_2$R$^{19}$, —S(=O)$_2$N(R$^{20a}$)(R$^{20b}$), —C(=O)-heterocycloalkyl, —C(=O)-heteroaryl, —C(=O)—N(R$^{18c}$)(R$^{18d}$), or —C(=CHNO$_2$)—N(R$^{18c}$)(R$^{18d}$);

In certain preferred embodiments, G$^2$ is alkyl, —C(=O)-heterocycloalkyl, —C(=O)—N(R$^{18c}$)(R$^{18d}$), —C(=HNO$_2$)—N(R$^{18c}$)(R$^{18d}$), or —C(=N—CN)—N(R$^{18e}$)(R$^{18f}$); more preferably —C(=O)-heterocycloalkyl or —C(=O)—N(R$^{18c}$)(R$^{18d}$); more preferably still N-carbonylmorpholino. In other preferred embodiments, G$^2$ is —S(=O)$_2$R$^{19}$, —C(=O)-heterocycloalkyl, —C(=O)-heteroaryl, or —C(=O)—N(R$^{18c}$)(R$^{18d}$). In yet other preferred embodiments, G$^2$ is alkyl or —C(=O)—N(R$^{18c}$)(R$^{18d}$), more preferably —C(=O)—N(R$^{18c}$)(R$^{18d}$). In other preferred embodiments, G$^2$ is alkyl, acyl, or —C(=O)—N(R$^{18c}$)(R$^{18d}$). In certain preferred embodiments, wherein G$^2$ is acyl, the alkyl of said acyl is preferably C$_1$-C$_6$ alkyl, more preferably tert-butyl or isopropyl, each optionally substituted, preferably with amino. In certain preferred embodiments, wherein G$^2$ is alkyl, it is more preferably C$_1$-C$_6$ alkyl, more preferably 2,2-dimethyl-prop-1-yl. In still other preferred embodiments, G$^2$ is —S(=O)$_2$R$^{19}$, —S(=O)$_2$N(R$^{20a}$)(R$^{20b}$), —C(=O)—N(R$^{18c}$)(R$^{18d}$), or —C(=N—CN)—N(R$^{18e}$)(R$^{18f}$).

In other preferred embodiments, R$^{9a}$ is H.

In some preferred embodiments, R$^{9b}$ is H or C$_1$-C$_3$ alkyl, more preferably H or ethyl, more preferably still ethyl.

In yet other preferred embodiments, each R$^{10}$, R$^{11}$, R$^{12}$, and R$^{13}$ is independently H, alkyl; more preferably H or C$_1$-C$_6$ alkyl. yet more preferably H or C$_1$-C$_3$ alkyl, even more preferably H or methyl.

In certain preferred embodiments, each R$^{14a}$ and R$^{14b}$ is independently H, alkyl, —CN, —(CH$_2$)$_r$—OH, or —(CH$_2$)$_r$—O-alkyl; still more preferably H or alkyl, yet more preferably H. In other preferred embodiments, at least one of R$^{14a}$ and R$^{14b}$ is independently —(CH$_2$)$_r$—OH or —(CH$_2$)$_r$—O-alkyl.

In some preferred embodiments, each R$^{18a}$, R$^{18b}$, R$^{18c}$, R$^{18d}$, R$^{18e}$, R$^{18f}$, R$^{20a}$, and R$^{20b}$ is independently H, alkyl, or aryl, more preferably H or alkyl, yet more preferably H or lower alkyl, or each R$^{18a}$ and R$^{18b}$ or R$^{18c}$ and R$^{18d}$ or R$^{20a}$ and R$^{20b}$, taken together with the nitrogen atom to which they are attached independently form a 4- to 8-membered heterocyclic ring wherein 1 or 2 of the ring carbon atoms independently may be optionally replaced by —O—, —S—, —S(=O)—, —S(=O)$_2$—, —NH—, or —N(alkyl)-. In some more preferred embodiments, each R$^{18a}$, R$^{18b}$, R$^{18c}$, R$^{18d}$, R$^{18e}$, R$^{18f}$, R$^{20a}$, and R$^{20b}$ is independently H or lower alkyl; yet more preferably wherein at least one of R$^{18a}$, R$^{18b}$, R$^{18c}$, R$^{18d}$, R$^{18e}$, R$^{18f}$, R$^{20a}$, and R$^{20b}$ is H. In some even more preferred embodiments, at least one of R$^{18c}$ and R$^{18d}$ is H. In other preferred embodiments, one of R$^{18c}$ and R$^{18d}$ is alkyl, preferably lower alkyl optionally substituted with —C(=O)—OR$^{9b}$. In other preferred embodiments, one of R$^{18c}$ and R$^{18d}$ is H and the other is alkyl, preferably C$_1$-C$_3$ alkyl. In other preferred embodiments, at least one of R$^{17}$ and R$^{18c}$ is H.

In other preferred embodiments, one of R$^{18c}$ and R$^{18d}$ is aryl, more preferably optionally substituted phenyl, yet more preferably phenyl substituted with at least one substituent selected from the group consisting of methoxy, dialkylamino, and cyano; even more preferably the aryl is selected from the group consisting of meta-alkoxyphenyl, meta-dialkylaminophenyl, meta-cyanophenyl, para-alkoxyphenyl, para-dialkylaminophenyl, and para-cyanophenyl. Yet more preferably the meta-alkoxyphenyl and para-alkoxyphenyl are meta-methoxyphenyl and para-methoxyphenyl.

In still other preferred embodiments, each R is independently H or alkyl; even more preferably H or lower alkyl; yet more preferably H or C$_1$-C$_3$ alkyl; still more preferably ethyl or methyl.

In certain preferred embodiments, W is a single bond, —O—, —S—, —CH$_2$—, —CF$_2$—, alkylidene, or —CH(O-alkyl); more preferably a single bond, —O—, —CH$_2$—, or alkylidene; even more preferably a single bond, —O— or —CH$_2$—, yet more preferably —O— or —CH$_2$—.

In some preferred embodiments, X is a single bond, —CH=CH—, or —N(R$^{21}$)—, more preferably a single bond or —N(R$^{21}$)—.

In other preferred embodiments, each R$^{15a}$, R$^{15b}$, R$^{16a}$, R$^{16b}$, R$^{17}$, and R$^{21}$ is independently H or lower alkyl; more preferably H or methyl. In some preferred embodiments, at least one of R$^{17}$ and R$^{21}$ is H, more preferably both are H. In some preferred embodiments, at least one of R$^{15a}$, R$^{16a}$, and R$^{21}$ is H, more preferably each is H. In some preferred embodiments, at least one of R$^{17}$ and R$^{18c}$ is H.

In some preferred embodiments, R$^{18c}$ and R$^{21}$, taken together with the atoms through which they are connected form a 4- to 8-membered heterocyclic ring wherein 1 or 2 of the ring carbon atoms independently may be optionally replaced by —O—, —S—, —S(=O)—, —S(=O)$_2$—, —NH—, —N(alkyl)-, —N(C(=O)—R$^{9a}$)—, or —N(S(=O)$_2$-alkyl)-; more preferably optionally replaced by —O—, —S(=O)$_2$—, —NH—, —N(alkyl)-, —N(C(=O)—R$^{9a}$)—, or —N(S(=O)$_2$-alkyl)-; even more preferably optionally replaced by —O—, —S(=O)$_2$—, —NH—, —N(alkyl)-, or —N(S(=O)$_2$-alkyl)-; yet more preferably still by —O—, —N(alkyl)-, or —N(S(=O)$_2$-alkyl)-.

In some other preferred embodiments, R$^{17}$ and R$^{18c}$, taken together with the atoms through which they are connected form a 4- to 8-membered heterocyclic ring wherein 1 or 2 of the ring carbon atoms independently may be optionally replaced by —O—, —S—, —S(=O)—, —S(=O)$_2$—, —NH—, —N(alkyl)-, —N(C(=O)—R$^{9a}$)—, or —N(S(=O)$_2$-alkyl)-; even more preferably wherein 1 or 2 of the ring carbon atoms may be optionally replaced by —O—, —S(=O)—, —S(=O)$_2$—, —NH—, or —N(alkyl)-.

In certain preferred embodiments, m and n are each independently an integer from 1 to 4; more preferably 1 to 3. In certain preferred embodiments, m is 1. In certain other preferred embodiments, n is 1 or 2, more preferably 2.

In other preferred embodiments, each p is independently an integer from 0 to 4; more preferably 0 to 3; more preferably still 0 to 2; and even more preferably 1 or 2; more preferably still 1.

In some preferred embodiments, each r is independently an integer from 0 to 3; more preferably 1 to 3; more preferably still 1 or 2.

In certain preferred embodiments, the compounds of formula I have the structure IIa or IIb:

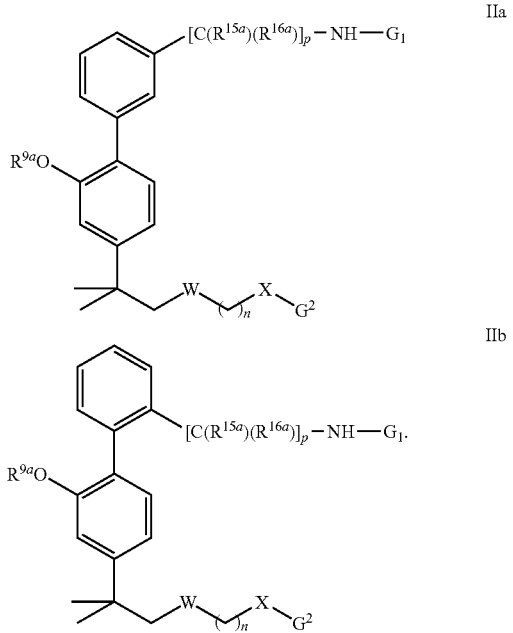

In other preferred embodiments, the compounds of formula I are selected from the group consisting of:

1-[4'-(1,1-dimethylheptyl)-2'-hydroxybiphenyl-2-yl]-3-ethyl-urea;
N-[4'-(1,1-dimethylheptyl)-2'-hydroxybiphenyl-2-yl]-methanesulfonamide;
N-[4'-(1,1-dimethylheptyl)-2'-hydroxybiphenyl-3-yl]-methanesulfonamide;
6-(2-hydroxy-3'-methanesulfonylaminobiphenyl-4-yl)-6-methyl-heptanoic acid methyl ester;
1-[4'-(1,1-dimethylheptyl)-2'-hydroxybiphenyl-3-ylmethyl]-3-ethyl-urea;
1-[4'-(1,1-dimethylheptyl)-2'-hydroxybiphenyl-2-ylmethyl]-3-ethyl-urea;
1-{2-[4'-(1,1-dimethylheptyl)-2'-hydroxybiphenyl-2-yl]-ethyl}-3-ethyl-urea;
N-[4'-(1,1-dimethylheptyl)-2'-hydroxy-biphenyl-3-ylmethyl]methanesulfonamide;
N-[4'-(1,1-dimethylheptyl)-2'-hydroxy-biphenyl-2-ylmethyl]-methanesulfonamide;
N-{2-[4'-(1,1-dimethylheptyl)-2'-hydroxybiphenyl-2-yl]-ethyl}-methanesulfonamide;
1-{4'-[1,1-dimethyl-2-(3-morpholin-4-yl-3-oxo-propoxy)-ethyl]-2'-hydroxybiphenyl-3-ylmethyl}-3-ethyl-urea;
1-[4'-(2-butoxy-1,1-dimethylethyl)-2'-hydroxybiphenyl-2-ylmethyl]-3-ethyl-urea;
1-[4'-(2-butoxy-1,1-dimethylethyl)-2'-hydroxybiphenyl-2-ylmethyl]-3-propyl-urea;
1-[4'-(2-butoxy-1,1-dimethylethyl)-2'-hydroxybiphenyl-3-ylmethyl]-3-ethyl-urea;
1-[4'-(2-butoxy-1,1-dimethylethyl)-2'-hydroxybiphenyl-3-ylmethyl]-3-propyl-urea;
1-ethyl-3-{2'-hydroxy-4'-[2-(2-methoxyethoxy)-1,1-dimethylethyl]-biphenyl-2-ylmethyl}-urea;
1-ethyl-3-{2'-hydroxy-4'-[2-(2-methoxyethoxy)-1,1-dimethylethyl]-biphenyl-3-ylmethyl}-urea;
1-[4'-(1,1-dimethyl-6-morpholin-4-yl-6-oxo-hexyl)-2'-hydroxybiphenyl-2-ylmethyl]-3-ethyl-urea;
1-[4'-(1,1-dimethyl-6-morpholin-4-yl-6-oxo-hex-4-enyl)-2'-hydroxybiphenyl-2-yl-methyl]-3-ethyl-urea;
1-[4'-(1,1-dimethyl-6-morpholin-4-yl-6-oxo-hexyl)-2'-hydroxybiphenyl-3-yl-methyl]-3-ethyl-urea;
1-[4'-(1,1-dimethyl-6-morpholin-4-yl-6-oxo-hexyl)-2'-hydroxybiphenyl-2-yl-methyl]-3-methyl-urea;
1-[4'-(1,1-dimethyl-6-morpholin-4-yl-6-oxo-hexyl)-2'-hydroxybiphenyl-2-yl-methyl]-3-isopropyl-urea;
1-[4'-(1,1-dimethyl-6-morpholin-4-yl-6-oxo-hexyl)-2'-hydroxybiphenyl-2-yl-methyl]-3-(4-methoxyphenyl)-urea;
{3-[4'-(1,1-dimethyl-6-morpholin-4-yl-6-oxo-hexyl)-2'-hydroxybiphenyl-2-ylmethyl]-ureido}-acetic acid ethyl ester;
1-(4-dimethylaminophenyl)-3-[4'-(1,1-dimethyl-6-morpholin-4-yl-6-oxo-hexyl)-2'-hydroxybiphenyl-2-ylmethyl]-urea;
1-(3-cyanophenyl)-3-[4'-(1,1-dimethyl-6-morpholin-4-yl-6-oxo-hexyl)-2'-hydroxybiphenyl-2-ylmethyl]-urea;
1-[4'-(1,1-dimethyl-6-morpholin-4-yl-6-oxo-hexyl)-2'-hydroxybiphenyl-2-ylmethyl]-3-(3-methoxyphenyl)-urea;
1-[4'-(1,1-dimethyl-6-morpholin-4-yl-6-oxo-hexyl)-2'-hydroxybiphenyl-3-ylmethyl]-3-methyl-urea;
1-[4'-(1,1-dimethyl-6-morpholin-4-yl-6-oxo-hexyl)-2'-hydroxybiphenyl-3-ylmethyl]-3-isopropyl-urea;
1-[4'-(1,1-dimethyl-6-morpholin-4-yl-6-oxo-hexyl)-2'-hydroxybiphenyl-3-ylmethyl]-3-(4-methoxyphenyl)-urea;
{3-[4'-(1,1-dimethyl-6-morpholin-4-yl-6-oxo-hexyl)-2'-hydroxybiphenyl-3-ylmethyl]-ureido}-acetic acid ethyl ester;
1-(4-dimethylaminophenyl)-3-['-(1,1-dimethyl-6-morpholin-4-yl-6-oxo-hexyl)-2'-hydroxybiphenyl-3-ylmethyl]-urea;
1-(3-cyanophenyl)-3-[4'-(1,1-dimethyl-6-morpholin-4-yl-6-oxo-hexyl)-2'-hydroxybiphenyl-3-ylmethyl]-urea;
1-[4'-(1,1-dimethyl-6-morpholin-4-yl-6-oxo-hexyl)-2'-hydroxybiphenyl-3-ylmethyl]-3-(3-methoxyphenyl)-urea;
N-(4-{3'-[(3-ethylureido)-methyl]-2-hydroxybiphenyl-4-yl}-4-methylpentyl)-2,2-dimethylpropionamide;
1-(4-{2'-[(3-ethylureido)-methyl]-2-hydroxybiphenyl-4-yl}-4-methylpentyl)-3-isopropylurea;
1-(4-{3'-[(3-ethylureido)-methyl]-2-hydroxybiphenyl-4-yl}-4-methylpentyl)-3-isopropylurea;
ethylcarbamic acid 4-{3'-[(3-ethylureido)-methyl]-2-hydroxybiphenyl-4-yl}-4-methylpentyl ester;
ethylcarbamic acid 4-{2'-[(3-ethylureido)-methyl]-2-hydroxybiphenyl-4-yl}-4-methylpentyl ester;
morpholine-4-carboxylic acid(4-{3'-[(3-ethylureido)-methyl]-2-hydroxybiphenyl-4-yl}-4-methylpentyl)-amide;

tetrahydrofuran-2-carboxylic acid[4'-(1,1-dimethyl-6-morpholin-4-yl-6-oxo-hexyl)-2'-hydroxybiphenyl-3-ylmethyl]-amide;

furan-2-carboxylic acid[4'-(1,1-dimethyl-6-morpholin-4-yl-6-oxo-hexyl)-2'-hydroxybiphenyl-3-ylmethyl]-amide;

furan-3-carboxylic acid[4'-(1,1-dimethyl-6-morpholin-4-yl-6-oxo-hexyl)-2'-hydroxybiphenyl-3-ylmethyl]-amide;

isoxazole-5-carboxylic acid[4'-(1,1-dimethyl-6-morpholin-4-yl-6-oxo-hexyl)-2'-hydroxybiphenyl-3-ylmethyl]-amide;

2,5-dimethylfuran-3-carboxylic acid[4'-(1,1-dimethyl-6-morpholin-4-yl-6-oxo-hexyl)-2'-hydroxybiphenyl-3-ylmethyl]-amide;

N-[4'-(1,1-dimethyl-6-morpholin-4-yl-6-oxo-hexyl)-2'-hydroxybiphenyl-3-ylmethyl]-nicotinamide;

pyrazine-2-carboxylic acid[4'-(1,1-dimethyl-6-morpholin-4-yl-6-oxo-hexyl)-2'-hydroxybiphenyl-3-ylmethyl]-amide;

1-methyl-1H-pyrrole-2-carboxylic acid[4'-(1,1-dimethyl-6-morpholin-4-yl-6-oxo-hexyl)-2'-hydroxybiphenyl-3-ylmethyl]-amide;

5-methylisoxazole-3-carboxylic acid[4'-(1,1-dimethyl-6-morpholin-4-yl-6-oxo-hexyl)-2'-hydroxybiphenyl-3-ylmethyl]-amide;

thiophene-3-carboxylic acid[4'-(1,1-dimethyl-6-morpholin-4-yl-6-oxo-hexyl)-2'-hydroxybiphenyl-3-ylmethyl]-amide;

5-oxo-pyrrolidine-2-carboxylic acid[4'-(1,1-dimethyl-6-morpholin-4-yl-6-oxo-hexyl)-2'-hydroxybiphenyl-3-ylmethyl]-amide;

[1,2,3]-thiadiazole-4-carboxylic acid[4'-(1,1-dimethyl-6-morpholin-4-yl-6-oxo-hexyl)-2'-hydroxybiphenyl-3-ylmethyl]-amide;

5-methylpyrazine-2-carboxylic acid[4'-(1,1-dimethyl-6-morpholin-4-yl-6-oxo-hexyl)-2'-hydroxybiphenyl-3-ylmethyl]-amide;

N-[4'-(1,1-dimethyl-6-morpholin-4-yl-6-oxo-hexyl)-2'-hydroxybiphenyl-3-ylmethyl]-1-hydroxyisonicotinamide N-oxide;

1,5-dimethyl-1H-pyrazole-3-carboxylic acid[4'-(1,1-dimethyl-6-morpholin-4-yl-6-oxo-hexyl)-2'-hydroxybiphenyl-3-ylmethyl]-amide;

tetrahydrofuran-2-carboxylic acid[4'-(1,1-dimethyl-6-morpholin-4-yl-6-oxo-hexyl)-2'-hydroxybiphenyl-2-ylmethyl]-amide furan-2-carboxylic acid[4'-(1,1-dimethyl-6-morpholin-4-yl-6-oxo-hexyl)-2'-hydroxybiphenyl-2-ylmethyl]-amide;

furan-3-carboxylic acid[4'-(1,1-dimethyl-6-morpholin-4-yl-6-oxo-hexyl)-2'-hydroxybiphenyl-2-ylmethyl]-amide;

isoxazole-5-carboxylic acid[4'-(1,1-dimethyl-6-morpholin-4-yl-6-oxo-hexyl)-2'-hydroxybiphenyl-2-ylmethyl]-amide;

2,5-dimethylfuran-3-carboxylic acid[4'-(1,1-dimethyl-6-morpholin-4-yl-6-oxo-hexyl)-2'-hydroxybiphenyl-2-ylmethyl]-amide;

N-[4'-(1,1-dimethyl-6-morpholin-4-yl-6-oxo-hexyl)-2'-hydroxybiphenyl-2-ylmethyl]-nicotinamide;

pyrazine-2-carboxylic acid[4'-(1,1-dimethyl-6-morpholin-4-yl-6-oxo-hexyl)-2'-hydroxybiphenyl-2-ylmethyl]-amide;

1-methyl-1H-pyrrole-2-carboxylic acid[4'-(1,1-dimethyl-6-morpholin-4-yl-6-oxo-hexyl)-2'-hydroxybiphenyl-2-ylmethyl]-amide;

5-methylisoxazole-3-carboxylic acid[4'-(1,1-dimethyl-6-morpholin-4-yl-6-oxo-hexyl)-2'-hydroxybiphenyl-2-ylmethyl]-amide;

thiophene-3-carboxylic acid[4'-(1,1-dimethyl-6-morpholin-4-yl-6-oxo-hexyl)-2'-hydroxybiphenyl-2-ylmethyl]-amide;

5-oxopyrrolidine-2-carboxylic acid[4'-(1,1-dimethyl-6-morpholin-4-yl-6-oxo-hexyl)-2'-hydroxybiphenyl-2-ylmethyl]-amide;

[1,2,3]-thiadiazole-4-carboxylic acid[4'-(1,1-dimethyl-6-morpholin-4-yl-6-oxo-hexyl)-2'40 -hydroxybiphenyl-2-ylmethyl]-amide;

5-methylpyrazine-2-carboxylic acid[4'-(1,1-dimethyl-6-morpholin-4-yl-6-oxo-hexyl)-2'-hydroxybiphenyl-2-ylmethyl]-amide;

tetrahydrofuran-2-carboxylic acid[4'-(1,1-dimethyl-6-morpholin-4-yl-6-oxo-hexyl)-2'-hydroxybiphenyl-3-ylmethyl]-amide;

furan-2-carboxylic acid[4'-(1,1-dimethyl-6-morpholin-4-yl-6-oxo-hexyl)-2'-hydroxybiphenyl-3-ylmethyl]-amide;

4'-(1,1-dimethyl-6-morpholin-4-yl-6-oxo-hexyl)-2'-hydroxybiphenyl-3-ylmethyl]-methanesulfonamide;

4'-(1,1-dimethyl-6-morpholin-4-yl-6-oxo-hexyl)-2'-hydroxybiphenyl-2-ylmethyl]-methanesulfonamide;

2-amino-N-(4-(3'-((3-ethylureido)methyl)-2-hydroxybiphenyl-4-yl)-4-methylpentyl)-2-methylpropanamide;

N-(4-(3'-((3-ethylureido)-methyl)-2-hydroxybiphenyl-4-yl)-4-methylpentyl)-nicotinamide;

1-ethyl-3-((2'-methoxy-4'-(2-methyl-7-morpholino-7-oxoheptan-2-yl)-biphenyl-3-yl)methyl)urea;

N-(4-(3'-((3-ethylureido)-methyl)-2-methoxybiphenyl-4-yl)-4-methylpentyl)-pivalamide;

1-ethyl-3-((2'-hydroxy-4'-(2-methyl-7-morpholinoheptan-2-yl)-biphenyl-3-yl)methyl)-urea;

1-ethyl-3-((2'-hydroxy-4'-(2-methyl-5-(neopentylamino)-pentan-2-yl)biphenyl-3-yl)-methyl)urea; and pharmaceutically acceptable salts thereof.

In still other preferred embodiments, the compounds of formula I are selected from the group consisting of:

1-{4'-[1,1-dimethyl-2-(3-morpholin-4-yl-3-oxo-propoxy)-ethyl]-2'-hydroxy-biphenyl-3-yl-methyl}-3-ethyl-urea;

N-(4-{3'-[(3-ethyl-ureido)-methyl]-2-hydroxy-biphenyl-4-yl}-4-methyl-pentyl)-2,2-dimethyl-propionamide;

morpholine-4-carboxylic acid(4-{3'-[(3-ethyl-ureido)-methyl]-2-hydroxy-biphenyl-4-yl}-4-methyl-pentyl)-amide;

1-[4'-(1,1-dimethyl-6-morpholin-4-yl-6-oxo-hexyl)-2'-hydroxy-biphenyl-3-ylmethyl]-3-methyl-urea;

1-[4'-(1,1-dimethyl-6-morpholin-4-yl-6-oxo-hexyl)-2'-hydroxy-biphenyl-3-yl-methyl]-3-ethyl-urea;

1-[4'-(1,1-dimethyl-6-morpholin-4-yl-6-oxo-hexyl)-2'-hydroxy-biphenyl-3-yl-methyl]-3-isopropyl-urea;

1-(4-{3'-[(3-ethyl-ureido)-methyl]-2-hydroxy-biphenyl-4-yl}-4-methyl-pentyl)-3-isopropyl-urea;

1-[4'-(1,1-dimethyl-6-morpholin-4-yl-6-oxo-hexyl)-2'-hydroxy-biphenyl-2-yl-methyl]-3-methyl-urea;

1-[4'-(1,1-dimethyl-6-morpholin-4-yl-6-oxo-hexyl)-2'-hydroxy-biphenyl-2-ylmethyl]-3-ethyl-urea;

1-[4'-(1,1-dimethyl-6-morpholin-4-yl-6-oxo-hex-4-enyl)-2'-hydroxy-biphenyl-2-yl-methyl]-3-ethyl-urea;

1-[4'-(1,1-dimethyl-6-morpholin-4-yl-6-oxo-hexyl)-2'-hydroxy-biphenyl-2-yl-methyl]-3-isopropyl-urea;

tetrahydrofuran-2-carboxylic acid[4'-(1,1-dimethyl-6-morpholin-4-yl-6-oxo-hexyl)-2'-hydroxy-biphenyl-3-yl-methyl]-amide;

N-[4'-(1-dimethyl-6-morpholin-4-yl-6-oxo-hexyl)-2'-hydroxy-biphenyl-3-ylmethyl]-methanesulfonamide;

1-[4'-(2-butoxy-1,1-dimethyl-ethyl)-2'-hydroxy-biphenyl-2-ylmethyl]-3-ethyl-urea;

1-[4'-(2-butoxy-1,1-dimethyl-ethyl)-2'-hydroxy-biphenyl-2-ylmethyl]-3-propyl-urea;
1-[4'-(2-butoxy-1,1-dimethyl-ethyl)-2'-hydroxy-biphenyl-3-ylmethyl]-3-ethyl-urea;
1-[4'-(2-butoxy-1,1-dimethyl-ethyl)-2'-hydroxy-biphenyl-3-ylmethyl]-3-propyl-urea;
1-ethyl-3-{2'-hydroxy-4'-[2-(2-methoxy-ethoy)-1,1-dimethyl-ethyl]-biphenyl-2-ylmethyl}-urea;
1-ethyl-3-{2'-hydroxy-4'-[2-(2-methoxy-ethoxy)-1,1-dimethyl-ethyl]-biphenyl-3-ylmethyl}-urea;
1-[4'-(1,1-dimethyl-heptyl)-2'-hydroxy-biphenyl-3-yl-methyl]-3-ethyl-urea;
1-(4-{2'-[(3-ethyl-ureido)-methyl]-2-hydroxy-biphenyl-4-yl}-4-methyl-pentyl)-3-isopropyl-urea;
ethylcarbamic acid 4-{3'-[(3-ethyl-ureido)-methyl]-2-hydroxy-biphenyl-4-yl}-4-methyl-pentyl ester;
ethylcarbamic acid 4-{2'-[(3-ethyl-ureido)-methyl]-2-hydroxy-biphenyl-4-yl}-4-methyl-pentyl ester;
1-[4'-(1,1-dimethyl-6-morpholin-4-yl-6-oxo-hexyl)-2'-hydroxy-biphenyl-2-yl-methyl]-3-(4-methoxy-phenyl)-urea;
{3-[4'-(1,1-dimethyl-6-morpholin-4-yl-6-oxo-hexyl)-2'-hydroxy-biphenyl-2-yl-methyl]-ureido}-acetic acid ethyl ester;
1-(4-dimethylamino-phenyl)-3-[4'-(1,1-dimethyl-6-morpholin-4-yl-6-oxo-hexyl)-2'-hydroxy-bi-phenyl-2-yl-methyl]-urea;
1-(3-cyano-phenyl)-3-[4'-(1,1-dimethyl-6-morpholin-4-yl-6-oxo-hexyl)-2'-hydroxy-biphenyl-2-yl-methyl]-urea;
1-[4'-(1,1-dimethyl-6-morpholin-4-yl-6-oxo-hexyl)-2'-hydroxy-biphenyl-2-yl-methyl]3-(3-me-thoxy-phenyl)-urea;
1-[4'-(1,1-dimethyl-6-morpholin-4-yl-6-oxo-hexyl)-2'-hydroxy-biphenyl-3-yl-methyl]-3-(3-methoxy-phenyl)-urea;
{3-[4'-(1,1-dimethyl-6-morpholin-4-yl-6-oxo-hexyl)-2'-hydroxy-biphenyl-3-yl-methyl]-ureido}-acetic acid ethyl ester;
1-(4-dimethylamino-phenyl)-3-[4'-(1,1-dimethyl-6-morpholin-4-yl-6-oxo-hexyl)-2'-hydroxy-biphenyl-3-yl-methyl]-urea;
1-(3-cyano-phenyl)-3-[4'-(1,1-dimethyl-6-morpholin-4-yl-6-oxo-hexyl)-2'-hydroxy-biphenyl-3-yl-methyl]-urea;
1-[4'-(1,1-dimethyl-6-morpholin-4-yl-6-oxo-hexyl)-2'-hydroxy-biphenyl-3-ylmethyl]-3-(3-methoxy-phenyl)-urea; and
pharmaceutically acceptable salts thereof.

More preferably still, the compound of formula I is selected from the group consisting of:
1-{4'-[1,1-dimethyl-2-(3-morpholin-4-yl-3-oxo-propoxy)-ethyl]-2'-hydroxy-biphenyl-3-yl-methyl}-3-ethyl-urea;
N-(4-{3'-[(3-ethyl-ureido)-methyl]-2-hydroxy-biphenyl-4-yl}-4-methyl-pentyl)-2,2-dimethyl-propionamide;
morpholine-4-carboxylic acid(4-{3'-[(3-ethyl-ureido)-methyl]-2-hydroxy-biphenyl-4-yl}-4-methyl-pentyl)-amide;
1-[4'-(1,1-dimethyl-6-morpholin-4-yl-6-oxo-hexyl)-2'-hydroxy-biphenyl-3-ylmethyl]-3-methyl-urea;
1-[4'-(1,1-dimethyl-6-morpholin-4-yl-6-oxo-hexyl)-2'-hydroxy-biphenyl-3-yl-methyl]-3-ethyl-urea;
1-[4'-(1,1-dimethyl-6-morpholin-4-yl-6-oxo-hexyl)-2'-hydroxy-biphenyl-3-yl-methyl]-3-isopropyl-urea;
1-(4-{3'-[(3-ethyl-ureido)-methyl]-2-hydroxy-biphenyl-4-yl}-4-methyl-pentyl)-3-isopropyl-urea;
1-[4'-(1,1-dimethyl-6-morpholin-4-yl-6-oxo-hexyl)-2'-hydroxy-biphenyl-2-yl-methyl]-3-methyl-urea;
1-[4'-(1,1-dimethyl-6-morpholin-4-yl-6-oxo-hexyl)-2'-hydroxy-biphenyl-2-ylmethyl]-3-ethyl-urea;
1-[4'-(1,1-dimethyl-6-morpholin-4-yl-6-oxo-hex-4-enyl)-2'-hydroxy-biphenyl-2-yl-methyl]-3-ethyl-urea;
1-[4'-(1,1-dimethyl-6-morpholin-4-yl-6-oxo-hexyl)-2'-hydroxy-biphenyl-2-yl-methyl]-3-isopropyl-urea; p tetrahydro-furan-2-carboxylic acid[4'-(1,1-dimethyl-6-morpholin-4-yl-6-oxo-hexyl)-2'-hydroxy-biphenyl-3-yl-methyl]-amide;
N-[4'-(1,1-dimethyl-6-morpholin-4-yl-6-oxo-hexyl)-2'-hydroxy-biphenyl-3-ylmethyl]-methanesulfonamide;
1-[4'-(2-butoxy-1,1-dimethyl-ethyl)-2'-hydroxy-biphenyl-2-ylmethyl]-3-ethyl-urea;
1-[4'-(2-butoxy-1,1-dimethyl-ethyl)-2'-hydroxy-biphenyl-2-ylmethyl]-3-propyl-urea;
1-[4'-(2-butoxy-1,1-dimethyl-ethyl)-2'-hydroxy-biphenyl-3-ylmethyl]-3-ethyl-urea;
1-[4'-(2-butoxy-1,1-dimethyl-ethyl)-2'-hydroxy-biphenyl-3-ylmethyl]-3-propyl-urea;
1-ethyl-3-{2'-hydroxy-4'-[2-(2-methoxy-ethoxy)-1,1-dimethyl-ethyl]-biphenyl-2-ylmethyl}-urea;
1-ethyl-3-{2'-hydroxy-4'-[2-(2-methoxy-ethoxy)-1,1-dimethyl-ethyl]-biphenyl-3-ylmethyl}-urea; and
pharmaceutically acceptable salts thereof.

Even more preferably, the compound of formula I is selected from the group consisting of:
1-{4'-[1,1-dimethyl-2-(3-morpholin-4-yl-3-oxo-propoxy)-ethyl]-2'-hydroxy-biphenyl-3-yl-methyl}-3-ethyl-urea;
N-(4-{3'-[(3-ethyl-ureido)-methyl]-2-hydroxy-biphenyl-4-yl}-4-methyl-pentyl)-2,2-dimethyl-propionamide;
morpholine-4-carboxylic acid(4-{3'-[(3-ethyl-ureido)-methyl]-2-hydroxy-biphenyl-4-yl}-4-methyl-pentyl)-amide;
1-[4'-(1,1-dimethyl-6-morpholin-4-yl-6-oxo-hexyl)-2'-hydroxy-biphenyl-3-ylmethyl]-3-methyl-urea;
1-[4'-(1,1-dimethyl-6-morpholin-4-yl-6-oxo-hexyl)-2'-hydroxy-biphenyl-3-yl-methyl]-3-ethyl-urea;
1-[4'-(1,1-dimethyl-6-morpholin-4-yl-6-oxo-hexyl)-2'-hydroxy-biphenyl-3-yl-methyl]-3-isopropyl-urea;
1-(4-{3'-[(3-ethyl-ureido)-methyl]-2-hydroxy-biphenyl-4-yl}-4-methyl-pentyl)-3-isopropyl-urea;
1-[4'-(1,1-dimethyl-6-morpholin-4-yl-6-oxo-hexyl)-2'-hydroxy-biphenyl-2-yl-methyl]-3-methyl-urea;
1-[4'-(1,1-dimethyl-6-morpholin-4-yl-6-oxo-hexyl)-2'-hydroxy-biphenyl-2-ylmethyl]-3-ethyl-urea;
1-[4'-(1,1-dimethyl-6-morpholin-4-yl-6-oxo-hex-4-enyl)-2'-hydroxy-biphenyl-2-yl-methyl]-3-ethyl-urea;
1-[4'-(1,1-dimethyl-6-morpholin-4-yl-6-oxo-hexyl)-2'-hydroxy-biphenyl-2-yl-methyl]-3-isopropyl-urea;
tetrahydrofuran-2-carboxylic acid[4'-(1,1-dimethyl-6-morpholin-4-yl-6-oxo-hexyl)-2'-hydroxy-biphenyl-3-yl-methyl]-amide;
N-[4'-(1,1-dimethyl-6-morpholin-4-yl-6-oxo-hexyl)-2'-hydroxy-biphenyl-3-ylmethyl]-methanesulfonamide; and
pharmaceutically acceptable salts thereof.

Yet more preferably, the compound of formula I is selected from the group consisting of:
1-{4'-[1,1-dimethyl-2-(3-morpholin-4-yl-3-oxo-propoxy)-ethyl]-2'-hydroxy-biphenyl-3-yl-methyl}-3-ethyl-urea;
N-(4-{3'-[(3-ethyl-ureido)-methyl]-2-hydroxy-biphenyl-4-yl}-4-methyl-pentyl)-2,2-dimethyl-propionamide;
morpholine-4-carboxylic acid(4-{3'-[(3-ethyl-ureido)-methyl]-2-hydroxy-biphenyl-4-yl}-4-methyl-pentyl)-amide;
1-[4'-(1,1-dimethyl-6-morpholin-4-yl-6-oxo-hexyl)-2'-hydroxy-biphenyl-3-ylmethyl]-3-methyl-urea;

1-[4'-(1,1-dimethyl-6-morpholin-4-yl-6-oxo-hexyl)-2'-hydroxy-biphenyl-3-yl-methyl]-3-ethyl-urea;

1-[4'-(1,1-dimethyl-6-morpholin-4-yl-6-oxo-hexyl)-2'-hydroxy-biphenyl-3-yl-methyl]-3-isopropyl-urea; and
pharmaceutically acceptable salts thereof.

The compounds employed in the methods of the present invention may exist in prodrug form. As used herein, "prodrug" is intended to include any covalently bonded carriers which release the active parent drug, for example, as according to Formula I or other formulas or compounds employed in the methods of the present invention in vivo when such prodrug is administered to a mammalian subject. Since prodrugs are known to enhance numerous desirable qualities of pharmaceuticals (e.g., solubility, bioavailability, manufacturing, etc.) the compounds employed in the present methods may, if desired, be delivered in prodrug form. Thus, the present invention contemplates methods of delivering prodrugs. Prodrugs of the compounds employed in the present invention, for example Formula I, may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, carbocyclic, aryl, and alkylaryl esters such as methyl, ethyl, propyl, iso-propyl, butyl, isobutyl, sec-butyl, tert-butyl, cyclopropyl, phenyl, benzyl, and phenethyl esters, and the like.

The compounds are preferably combined with a pharmaceutical carrier selected on the basis of the chosen route of administration and standard pharmaceutical practice as described, for example, in *Remington's Pharmaceutical Sciences* (Mack Pub. Co., Easton, Pa., 1980), the disclosure of which is hereby incorporated herein by reference, in its entirety.

Although the compounds of the present invention may be administered as the pure chemicals, it is preferable to present the active ingredient as a pharmaceutical composition. The invention thus further provides a pharmaceutical composition comprising one or more of the cannabinoid receptor modulator compounds of the present invention, together with one or more pharmaceutically acceptable carriers therefore and, optionally, other therapeutic and/or prophylactic ingredients. The carrier(s) must be acceptable in the sense of being compatible with the other ingredients of the composition and not deleterious to the recipient thereof.

In accordance with certain embodiments of the present invention, the compositions of the invention may further comprise at least one cannabinoid. A variety of cannabinoids are available that may be suitable for use in the present methods and compositions. Generally speaking, it is only necessary that the cannabinoid provide the desired effect (for example, pain alleviation), and be capable of being incorporated into the present combination products and methods (discussed in detail below). In preferred embodiments, the present methods and compositions may involve a cannabinoid that is selected from $\Delta^9$-tetrahydrocannabinol and cannabidiol, and mixtures thereof.

Alternatively, in accordance with certain embodiments of the present invention, the compositions of the invention may further comprise at least one opioid. A wide variety of opioids are available that may be suitable for use in the present methods and compositions. Generally speaking, it is only necessary that the opioid provide the desired effect (for example, pain alleviation), and be capable of being incorporated into the present combination products and methods (discussed in detail below). In preferred embodiments, the present methods and compositions may involve an opioid that is selected from alfentanil, buprenorphine, butorphanol, codeine, dezocine, dihydrocodeine, fentanyl, hydrocodone, hydromorphone, levorphanol, loperamide, meperidine (pethidine), methadone, morphine, nalbuphine, oxycodone, oxymorphone, pentazocine, propiram, propoxyphene, sufentanil and/or tramadol. More preferably, the opioid is selected from morphine, codeine, oxycodone, hydrocodone, dihydrocodeine, propoxyphene, fentanyl, tramadol, and mixtures thereof.

Alternatively, in accordance with certain other embodiments of the present invention, the compositions of the invention may further comprise at least one analgesic, such as for example, COX2 inhibitors, aspirin, acetaminophen, ibuprofen, naproxen, and the like, and mixtures thereof. Generally speaking, it is only necessary that the analgesic provide the desired effect (for example, pain alleviation), and be capable of being incorporated into the present combination products and methods (discussed in detail below).

Alternatively, in accordance with still other embodiments of the present invention, the compositions of the invention may further comprise at least one therapeutic agent selected from the group consisting of anti seizure agents, such as for example, carbamazepine, gabapentin, lamotrigine, and phenytoin, anti-depressants such as, for example, amitryptiline, NMDA receptor antagonists, ion channel antagonists, nicotinic receptor agonists, and antiParkinson's agents, such as for example, Deprenyl, Amantadine, Levodopa, and Carbidopa. Generally speaking, it is only necessary that the anti seizure agent, anti-depressant, NMDA receptor antagonist, ion channel antagonist, nicotinic receptor agonist, or antiParkinson's agent provide the desired effect (for example, inhibition of seizures, alleviation of depression, and the like), and be capable of being incorporated into the present combination products and methods (discussed in detail below).

The compounds of the invention may be administered in an effective amount by any of the conventional techniques well-established in the medical field. The compounds employed in the methods of the present invention including, for example, the compounds of Formula I, IIa, or IIb, may be administered by any means that results in the contact of the active agents with the agents' site or site(s) of action in the body of a patient. The compounds may be administered by any conventional means available for use in conjunction with pharmaceuticals, either as individual therapeutic agents or in a combination of therapeutic agents. For example, they may be administered as the sole active agents in a pharmaceutical composition, or they can be used in combination with other therapeutically active ingredients.

Compounds of the present invention can be administered to a mammalian host in a variety of forms adapted to the chosen route of administration, e.g., orally or parenterally. Parenteral administration in this respect includes administration by the following routes: intravenous, intramuscular, subcutaneous, intraocular, intrasynovial, transepithelial including transdermal, ophthalmic, sublingual and buccal; topically including ophthalmic, dermal, ocular, rectal and nasal inhalation via insufflation, aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. The amount of active compound(s) in such therapeutically useful compositions is preferably such that a suitable dosage will be obtained. Preferred compositions or preparations according to the present invention may be prepared so that an oral dosage unit form contains from about 0.1 to about 1000 mg of active compound.

The tablets, troches, pills, capsules and the like may also contain one or more of the following: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl- and propyl-parabens as preservatives, a dye and flavoring, such as cherry or orange flavor. Of course, any material used in preparing any dosage unit form is preferably pharmaceutically pure and substantially non-toxic in the amounts employed. In addition, the active compound may be incorporated into sustained-release preparations and formulations.

The active compound may also be administered parenterally or intraperitoneally. Solutions of the active compounds as free bases or pharmacologically acceptable salts can be prepared in water suitably mixed with a surfactant, such as hydroxypropylcellulose. A dispersion can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compounds in the required amounts, in the appropriate solvent, with various of the other ingredients enumerated above, as required, followed by filtered sterilization. Generally, dispersions may be prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation may include vacuum drying and the freeze drying technique that yields a powder of the active ingredient, plus any additional desired ingredient from the previously sterile-filtered solution thereof.

The therapeutic compounds of this invention may be administered to a patient alone or in combination with a pharmaceutically acceptable carrier. As noted above, the relative proportions of active ingredient and carrier may be determined, for example, by the solubility and chemical nature of the compounds, chosen route of administration and standard pharmaceutical practice.

The dosage of the compounds of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. Generally speaking, oral administration may require higher dosages.

The combination products of this invention, such as pharmaceutical compositions comprising cannabinoids and/or opioids in combination with the compounds of Formula I, IIa, or IIb, may be in any dosage form, such as those described herein, and can also be administered in various ways, as described herein. In a preferred embodiment, the combination products of the invention are formulated together, in a single dosage form (that is, combined together in one capsule, tablet, powder, or liquid, etc.). When the combination products are not formulated together in a single dosage form, the cannabinoid and/or opioid compounds and the compounds of Formula I, IIa, or IIb, may be administered at the same time (that is, together), or in any order. When not administered at the same time, preferably the administration of a cannabinoid and/or opioid and the compounds of Formula I, IIa, or IIb, occurs less than about one hour apart, more preferably less than about 30 minutes apart, even more preferably less than about 15 minutes apart, and still more preferably less than about 5 minutes apart. Preferably, administration of the combination products of the invention is oral, although other routes of administration, as described above, are contemplated to be within the scope of the present invention. Although it is preferable that the cannabinoids and/or opioids and the compounds of Formula I, IIa, or IIb, are both administered in the same fashion (that is, for example, both orally), if desired, they may each be administered in different fashions (that is, for example, one component of the combination product may be administered orally, and another component may be administered intravenously). The dosage of the combination products of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired.

Although the proper dosage of the combination products of this invention will be readily ascertainable by one skilled in the art, once armed with the present disclosure, by way of general guidance, where a cannabinoid and/or opioid compound is combined with the compounds of Formula I, IIa, or IIb, for example, typically a daily dosage may range from about 0.01 to about 100 milligrams of the cannabinoid and/or opioid (and all combinations and subcombinations of ranges therein) and about 0.001 to about 100 milligrams of the compounds of Formula I, IIa, or IIb, (and all combinations and subcombinations of ranges therein), per kilogram of patient body weight. Preferably, the a daily dosage may be about 0.1 to about 10 milligrams of the cannabinoid and/or opioid and about 0.01 to about 10 milligrams of the compounds of Formula I, IIa, or IIb per kilogram of patient body weight. Even more preferably, the daily dosage may be about 1.0 milligrams of the cannabinoid and/or opioid and about 0.1 milligrams of the compounds of Formula I, IIa, or IIb per kilogram of patient body weight. With regard to a typical dosage form of this type of combination product, such as a tablet, the cannabinoid compounds (e.g. $\Delta^9$-tetrahydrocannabinol or cannabidiol) and/or the opioid compounds (e.g., morphine) and generally may be present in an amount of about 15 to about 200 milligrams, and the compounds of Formula I, IIa, or IIb in an amount of about 0.1 to about 4 milligrams.

Particularly when provided as a single dosage form, the potential exists for a chemical interaction between the combined active ingredients (for example, a cannabinoid and the compounds of Formula I, IIa, or IIb). For this reason, the preferred dosage forms of the combination products of this invention are formulated such that although the active ingredients are combined in a single dosage form, the physical contact between the active ingredients is minimized (that is, reduced).

In order to minimize contact, one embodiment of this invention where the product is orally administered provides for a combination product wherein one active ingredient is enteric coated. By enteric coating one or more of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material that effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropylmethylcellulose (HPMC) or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time by the same manner, will be readily apparent to those skilled in the art, once armed with the present disclosure.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The dose may also be provided by controlled release of the compound, by techniques well known to those in the art.

Pharmaceutical kits useful in, for example, the treatment of pain, which comprise a therapeutically effective amount of a cannabinoid and/or opioid along with a therapeutically effective amount of a phenyl compound of the invention, in one or more sterile containers, are also within the ambit of the present invention. Sterilization of the container may be carried out using conventional sterilization methodology well known to those skilled in the art. The sterile containers of materials may comprise separate containers, or one or more multi-part containers, as exemplified by the UNIVIAL™ two-part container (available from Abbott Labs, Chicago, Ill.), as desired. The opioid or cannabinoid compound and the compound of Formula I, IIa, or IIb may be separate, or combined into a single dosage form as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

The compounds of the present invention may be used in methods to bind cannabinoid receptors, more preferably CB1 or CB2 cannabinoid receptors. Such binding may be accomplished by contacting the receptor with an effective amount of a compound of formula I, IIa, or IIb. The cannabinoid receptors may be located in the central nervous system or located peripherally to the central nervous system or in both locations. Preferably, the contacting step conducted in an aqueous medium, preferably at physiologically relevant ionic strength, pH, and the like.

In certain preferred embodiments, the compounds, pharmaceutical compositions and methods of the present invention may involve a peripheral cannabinoid receptor agonist compound. The term "peripheral" designates that the compound acts primarily on physiological systems and components external to the central nervous system. In preferred form, the peripheral receptor agonist compounds employed in the methods of the present invention exhibit high levels of activity with respect to peripheral nerve tissue, while exhibiting reduced, and preferably substantially no CNS activity. The phrase "substantially no CNS activity," as used herein, means that less than about 20% of the pharmacological activity of the compounds employed in the present methods is exhibited in the CNS, preferably less than about 15%, more preferably less than about 10%, even more preferably less than about 5%, and most preferably 0%, of the pharmacological activity of the compounds employed in the present methods is exhibited in the CNS.

Furthermore, it is preferred in certain embodiments of the invention where the compound is administered to agonize the peripheral cannabinoid receptors does not substantially cross the blood-brain barrier and thereby reduces the classical central side effects as observed for blood-brain penetrating cannabinoid agonists such as $\Delta^9$-tetrahydrocannabinol ($\Delta^9$-THC). The central side effects of blood brain penetrating cannabinoid agonists limits their clinical utility, such as their use in the relief of pain. The phrase "does not substantially cross," as used herein, means that less than about 30% by weight of the compound employed in the present methods crosses the blood-brain barrier, preferably less than about 15% by weight, more preferably less than about 10% by weight, even more preferable less than about 5% by weight and most preferably 0% by weight of the compound crosses the blood-brain barrier. Selected compounds can be evaluated for CNS penetration by determining plasma and brain levels following i.v. administration.

In preferred embodiments, the compounds of the present invention may exhibit activity toward cannabinoid receptors, including binding thereto. Preferably, the present compounds are agonists toward cannabinoid receptors. Thus, in certain embodiments, the invention is directed, in part, to methods of binding cannabinoid receptors in a patient in need thereof, comprising the step of administering to said patient a composition comprising an effective amount of a compound of the present invention, preferably a compound of formula I. In preferred form, cannabinoid receptors which may be bound by the present compounds are CB1 and/or CB2 cannabinoid receptors. In certain more preferred embodiments, the cannabinoid receptors so bound are located in the central nervous system. In other more preferred embodiments, cannabinoid receptors so bound are located peripherally to the central nervous system. Also in some preferred embodiments, the present compounds may selectively bind the CB2 cannabinoid receptors relative to the CB1 receptors. Alternatively, the present compounds may selectively bind the CB1 cannabinoid receptors relative to the CB2 receptors. Also in preferred form, the present compounds do not substantially cross the blood-brain barrier.

Due to the activity of compounds of the present invention towards cannabinoid receptors, the present invention further contemplates their use in the treatment or prevention of diseases which are associated with cannabinoid receptors. Preferably, the present compounds may be useful in the treatment or prevention of a disease or disorder selected from the group consisting of pain, a gastrointestinal disorder, a genitourinary disorder, inflammatory disorders, glaucoma, an auto-immune disease, an ischemic condition, an immune-related disorder, and a neurodegenerative disease.

In embodiments involving the treatment or prevention of pain, the pain may be inflammatory pain, neuropathic pain, visceral pain, surgical pain, including pain which occurs during surgery or pain which occurs after surgery (i.e., postsurgical pain), or cancer related pain. In certain more preferred embodiments, the present pain ameliorating methods may further comprise the administration to the patient of at least on opioid in the form of combination products and/or combination therapy. Suitable opioids include, for example, alfentanil, buprenorphine, butorphanol, codeine, dezocine, dihydrocodeine, fentanyl, hydrocodone, hydromorphone, levorphanol, loperamide, meperidine (pethidine), methadone, morphine, nalbuphine, oxycodone, oxymorphone, pentazocine, propiram, propoxyphene, sufentanil or tramadol, and mixtures thereof. In embodiments involving the treatment or prevention of neuropathic pain, the present methods may further comprise administering to the patient codeine, carbamazepine, gabapentin, lamotrigine, phenytoin, amitryptiline, an NMDA receptor antagonist, an ion channel antagonist, or a nicotinic receptor agonist, or a mixture thereof, in the form of combination products and/or combination therapy.

Gastrointestinal disorders which may be treated with the present compounds and methods include, for example, nausea, vomiting, loss of appetite, cachexia, diarrhoea, inflammatory bowel disease, or irritable bowel syndrome.

Genitourinary disorders which may be treated with the present compounds and methods include, for example, bladder dysfunction or nephritis.

Auto-immune diseases which may be treated with the present compounds and methods include, for example, multiple sclerosis, rheumatoid arthritis, psoriasis, Crohn's disease, systemic lupus erythematosus, myasthenia gravis, *diabetes mellitus* type I, osteoporosis, or a combination thereof.

Ischemic conditions which may be treated with the present compounds and methods include, for example, renal ischemia, cerebral stroke, cerebral ischemia, or a combination thereof.

Immune-related disorders which may be treated with the present compounds and methods include, for example is asthma, chronic pulmonary obstructive disorder, emphysema, bronchitis, allergy, tissue rejection in organ transplants, celiac disease, Sjögren's syndrome, or a combination thereof.

Neurodegenerative diseases which may be treated with the present compounds and methods include, for example, Parkinson's disease, Alzheimer's disease, Huntington's disease, amyotrophic lateral sclerosis, or a combination thereof. In certain preferred embodiments, these methods may further comprise the administration to the patient of deprenyl, amantadine, levodopa, or carbidopa, in the form of combination products and/or combination therapy.

Ischemic or reperfusion effect which may be treated with the present compounds and methods include, for example, arrhythmia or hypertension.

In other preferred embodiments, the invention is directed, in part, to methods of inducing apoptosis in malignant cells, comprising the step of contacting said cells with an effective amount of a compound of the invention. In certain more preferred embodiments, apoptosis occurs in vitro. In other more preferred embodiments, apoptosis occurs in vivo.

In still other preferred embodiments, the invention is directed to methods for modulating appetite, comprising the step of administering to a patient in need thereof, an effective amount of a cannabinoid receptor agonist compound. In certain of these embodiments the modulation comprises stimulating appetite.

Methods of Preparation

Non-limiting compounds 1-78 in the examples have been prepared according to the general synthetic methodology in Schemes 1-9 outlined to prepare compounds of the present invention.

Commercially available (3-benzyloxy-phenyl)-acetonitrile (I) was converted to 2-(3-benzyloxy-phenyl)-2-methylpropionitrile (II) using methyl bromide gas in NaOH/DMSO, followed by a reduction with DIBAL-H yielding 2-(3-benzyloxy-phenyl)-2-methylpropionaldehyde (III). Further reduction of III with NaBH$_4$ afforded 2-(3-benzyloxy-phenyl)-2-methyl-propan-1-ol (IV). Wittig reactions of III with pentyl-triphenylphosphonium bromide, trimethyl-4-phosphonocrotonate, and trimethyl phosphonoacetate, produced 1-(1,1-dimethyl-hept-2-enyl)-3-phenethyl-benzene (V), 6-(3-benzyloxy-phenyl)-6-methyl-hepta-2,4-dienoic acid methyl ester (VIa), and 4-(3-benzyloxy-phenyl)-4-methyl-pent-2-enoic acid methyl ester (VIb) respectively (Scheme 1).

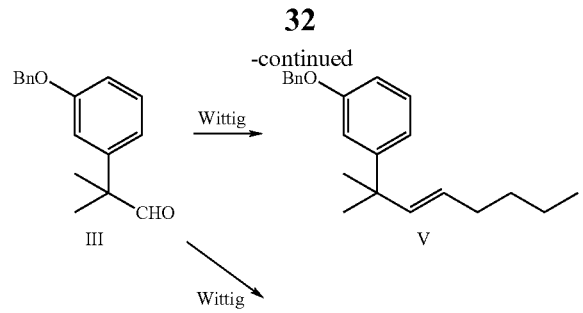

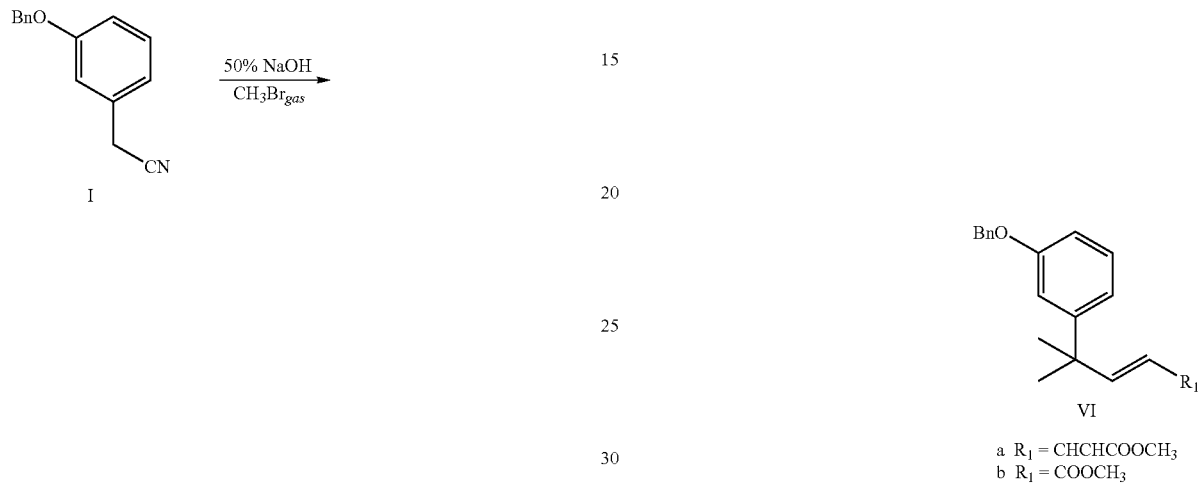

Wittig products V, VIa, and VIb were deprotected and brominated to afford free bromo-phenols VIIa-VIIc (Scheme 2).

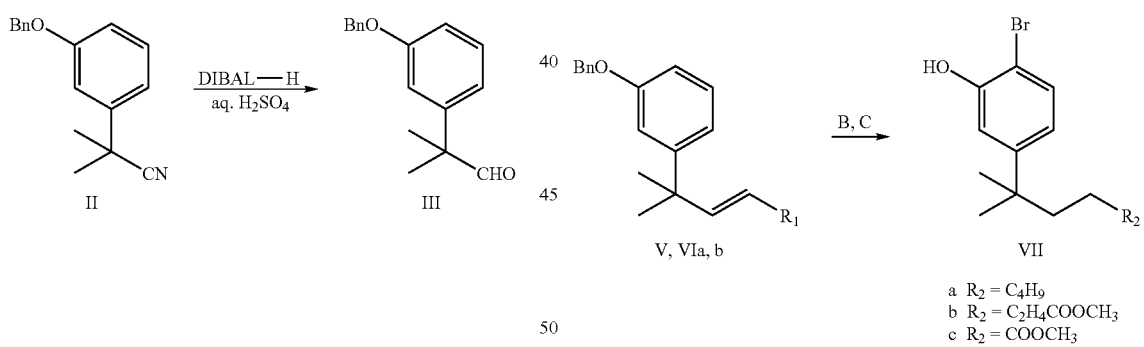

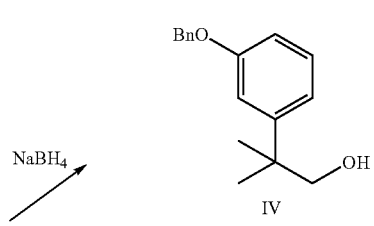

2-(3-Benzyloxy-phenyl)-2-methyl-propan-1-ol (IV) was alkylated with 1-bromobutane and 2-methoxyethyl bromide to yield ether derivatives IXa and IXb. Alkylation of IV with allyl bromide followed by reaction of intermediate IXc with 9-BBN (J. Chen et al. *J. Organomet. Chem.* 1978, 156(1), 213) and subsequent Jones oxidation (J. L. Adad et al. *J. Org. Chem.* 2000, 65, 8582) afforded acid IXe, which was converted to the acid chloride IXf and coupled to morpholine to yield amide IXg. Deprotection of IXa, IXb, and IXg, followed by bromination with Br$_2$ in CCl$_4$ produced bromo-phenols Xa-Xc (Scheme 3).

Scheme 3:

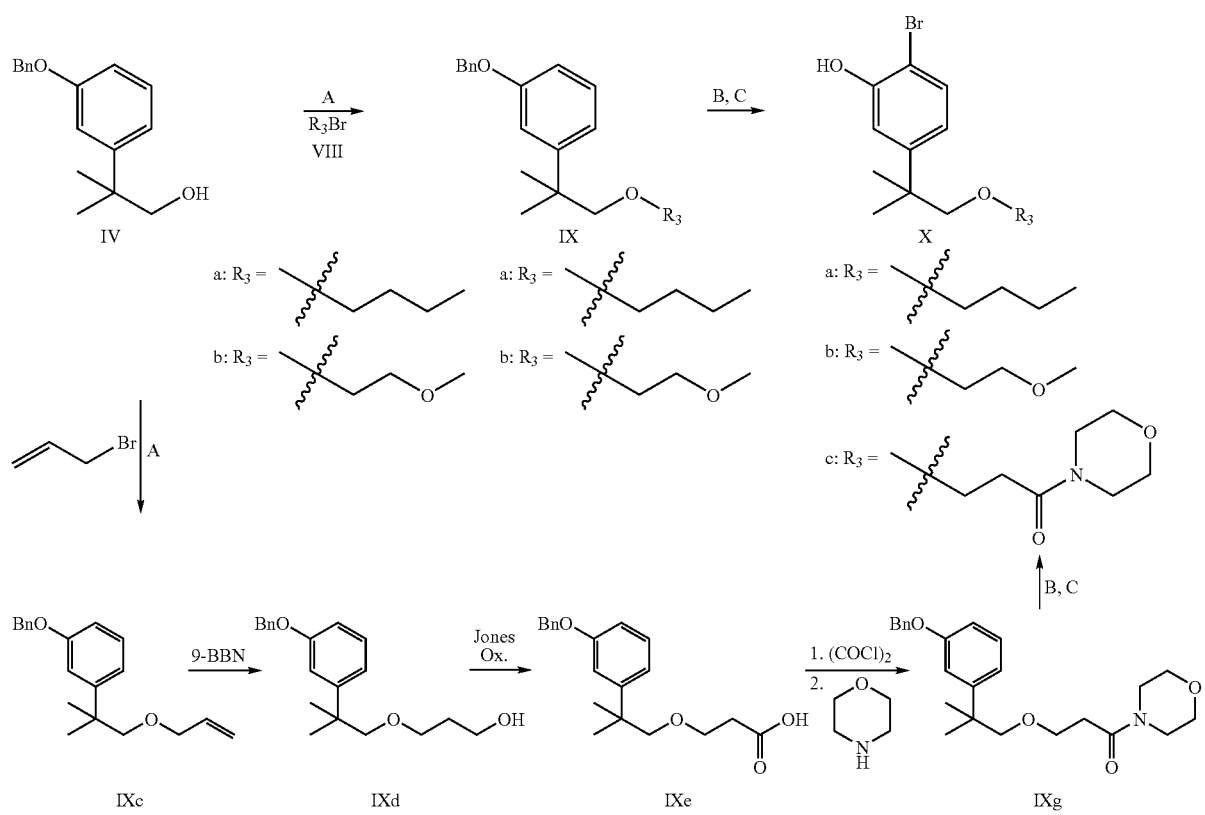

Wittig product VIa was hydrolyzed, converted to the acid chloride and coupled to morpholine to give amide XI. Deprotection followed by bromination with $Br_2$ in $CCl_4$ yielded bromo-phenol XII (Scheme 4).

Scheme 4:

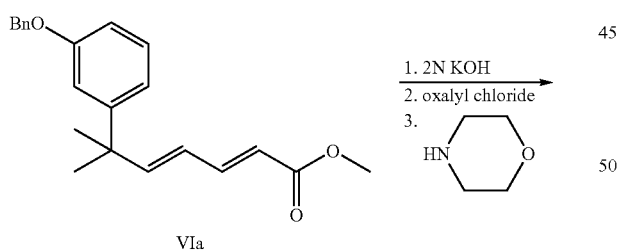

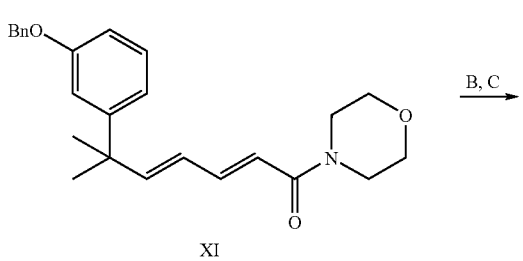

Bromo-phenols VIIa, VIb, Xa-Xc and XII were coupled to bromo-Wang resin using standard alkylation conditions (General Procedure A). Biphenyls XV were obtained via Suzuki coupling of resin bound bromo-phenols XIII with several boronates XIVa-XIVe under standard conditions. Compound 1 was obtained from XVa via cleavage from resin with TFA/dichloromethane. The resin bound amines XVb and XVc were treated with methanesulfonyl chloride, the resin bound phthalimides XVId and XVIe were cleaved with hydrazine and the resulting amines XVII were coupled with various isocyanates XVIII to yield ureas, with heterocyclic carboxylic acids XX to yield amides, and with sulfonyl chlorides XXII to yield sulfonamides. Final products XIX (compounds 5-7 and 11-34), XXI (compounds 41-70) and XXIII (compounds 2-4, 8-10, 71, 72) were obtained via cleavage from resin with TFA/dichloromethane (Scheme 5).

Scheme 5:
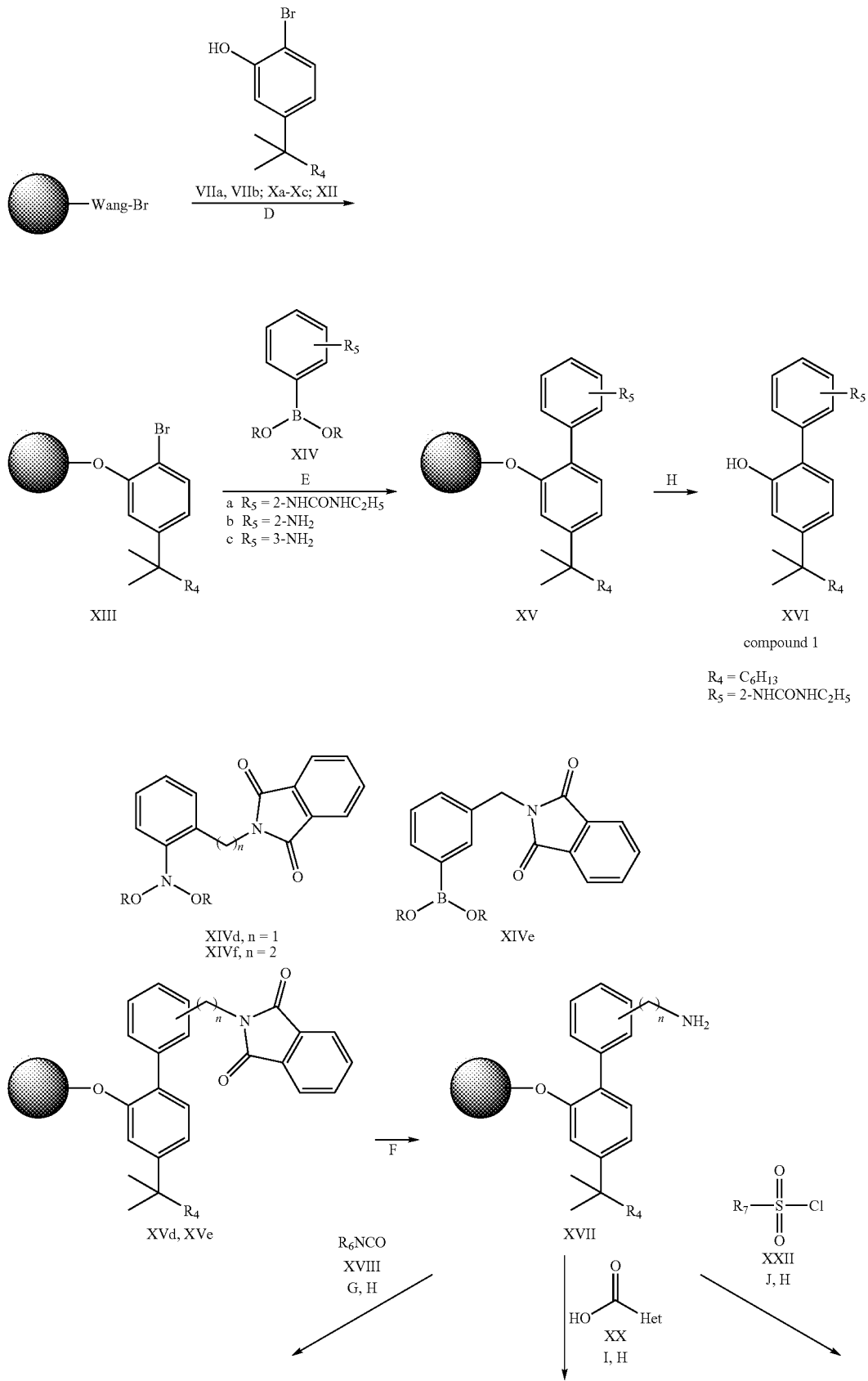

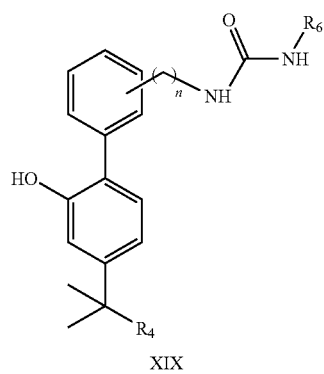
XIX
compound 5-7, 11-34
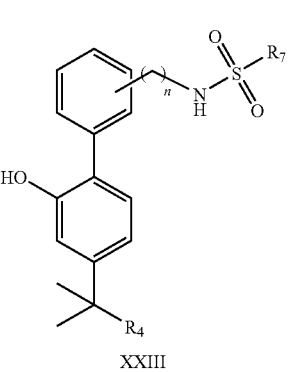
XXI
compound 41-70
XXIII
compound 2-4, 8-10, 71, 72
with R₄ equal to:
cmpds 2, 3, 5-10: 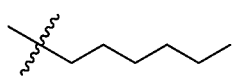
cmpds 11: 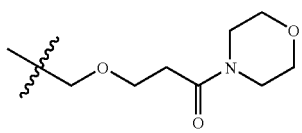
cmpd 4: 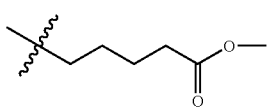
cmpds 18, 20-34, 41-72: 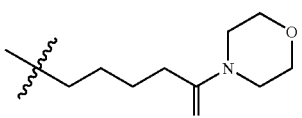
cmpds 12-14: 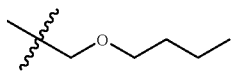
cmpd 19: 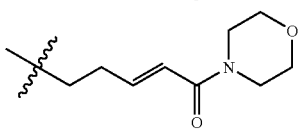
cmpds 16-17: 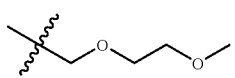
Isocyanates R₆NCO XVIII:
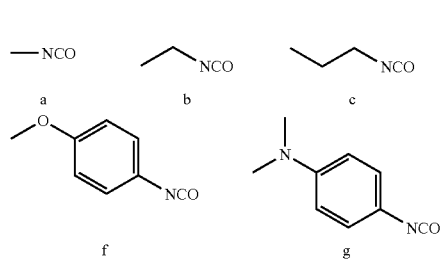
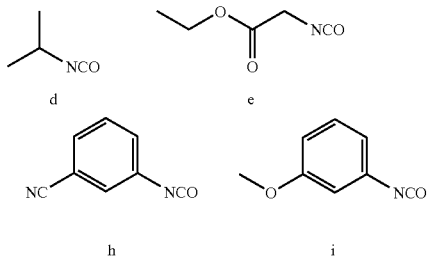
Carboxylic Acids Het-COOH XX:
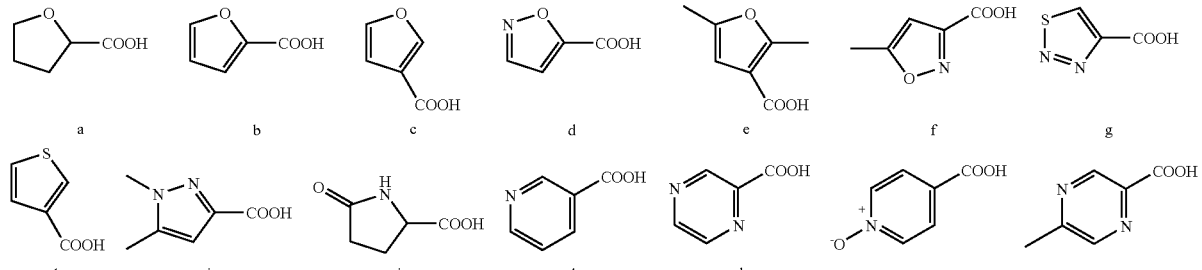
Sulfonamide R₇SO₂Cl XXII:
Methanesulfonyl chloride Phenol VIIc was coupled to bromo-Wang resin using standard alkylation conditions (Scheme 6).
Scheme 6:
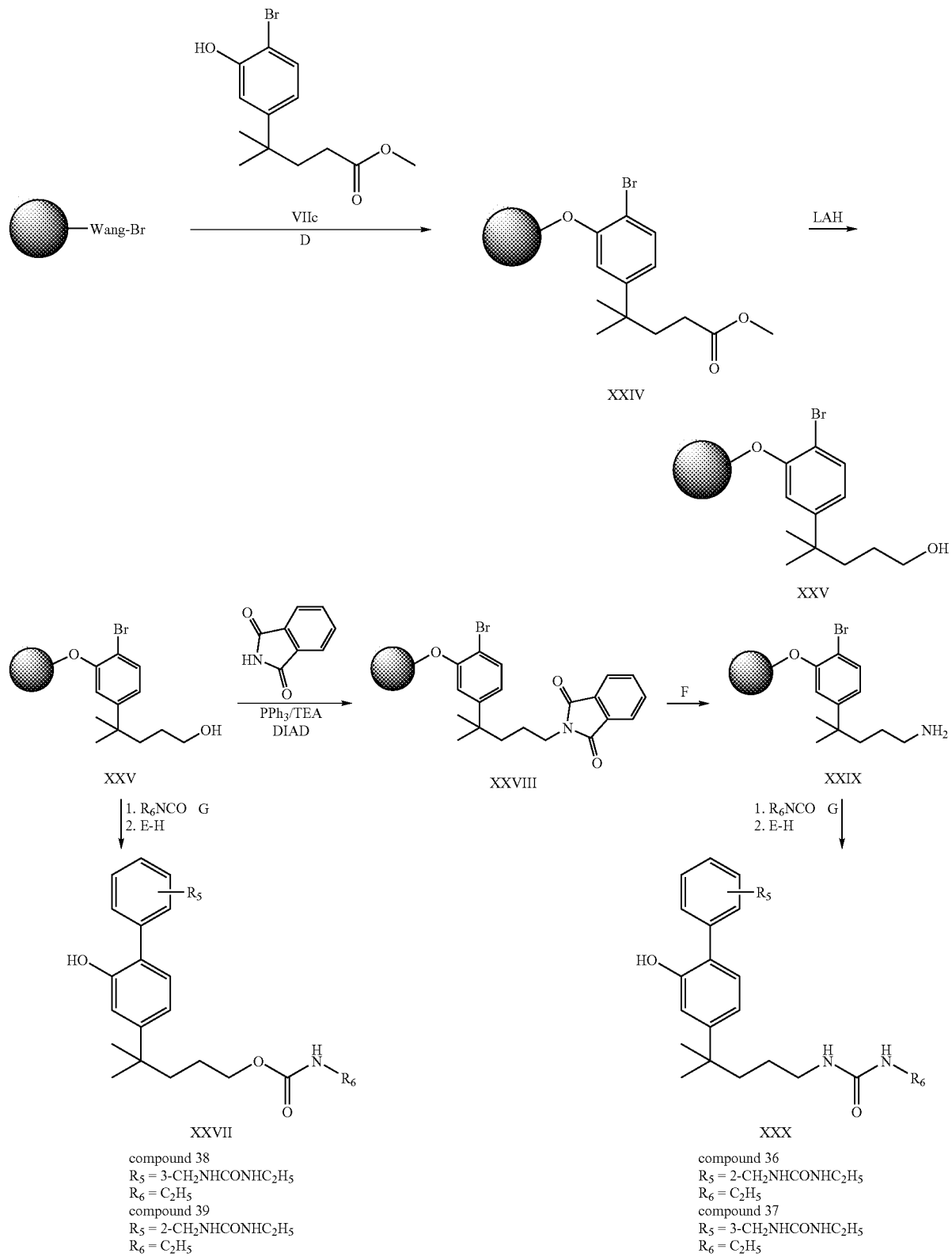

The resultant resin bound ester XXIV was reduced to alcohol XXV with LAH in tetrahydrofuran. The resulting alcohol XXV was converted to amine XXIX via Mitsunobu coupling to phthalimide XXVIII followed by hydrazine cleavage of XXVIII. Intermediate resin bound amine XXIX was reacted with isocyanates to yield ureas. Suzuki coupling with boronate XIV (analog to scheme 5), phthalimide cleavage, transformation to the urea, followed by TFA cleavage from resin afforded final compounds XXX (compounds 36 and 37). Reaction of alcohol XXV with isocyanates followed by Suzuki coupling, urea formation and cleavage from resin resulted in urethanes XXVII (Scheme 6) (compounds 38 and 39). Reaction of resin bound amine XXIX with a range of carboxylic acids using PyBrop as coupling agent, followed by Suzuki coupling, phthalimide cleavage, urea formation, and cleavage from resin resulted in reversed amide XXXII (compound 35, Scheme 7). Reaction of resin bound amine XXIX with morpholine carbonyl chloride followed by Suzuki coupling, urea formation and cleavage from resin afforded substituted urea XXXIII (compound 40, Scheme 7).

Scheme 7:

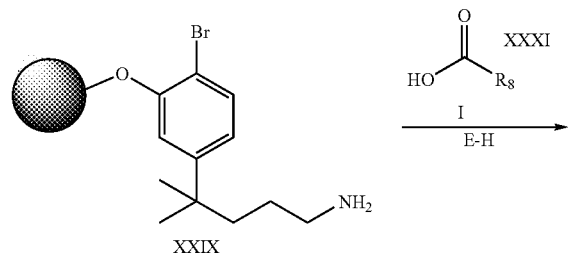

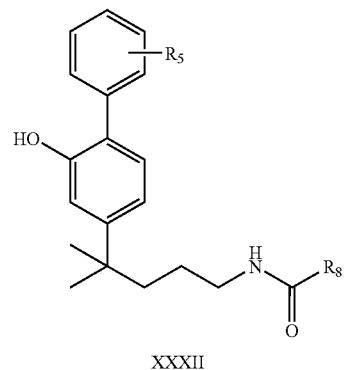

XXXII
compound 35
$R_5 = 3\text{-}CH_2NHCONHC_2H_5$
$R_8 = C(CH_3)_3$

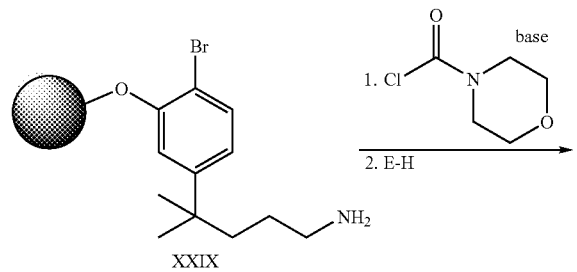

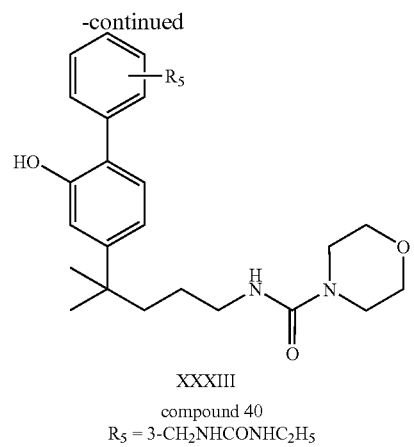

XXXIII
compound 40
$R_5 = 3\text{-}CH_2NHCONHC_2H_5$

Aldehyde III was condensed with 2-cyanoacetic acid to form nitrile XXXIV. A reduction with Raney-Nickel yielded amine XXXV which was converted to trifluoroacetamide XXXVIa using ethyl trifluoroacetate and triethylamine. Hydrogenation (General Procedure B) and bromination (General Procedure C) afforded intermediate XXXVII. Protection of the phenol with MOM-chloride followed by basic hydrolysis yielded amine XXXVIIIb. Amide coupling with acids XXXI to XXXIX was accomplished using O-(benzotriazol-1-yl)-1,1,3,3-tetramethyluronium tetrafluoroborate (TBTU) and DIEA in acetonitrile. Compound 73 was obtained from a TBTU coupling with 2-(tert-butoxycarbonylamino)-2-methylpropanoic acid, followed by a Suzuki coupling with 1-ethyl-3-(3-(4,4,5,5-tetramethyl-1,3,2-dioxaborolan-2-yl)benzyl) urea XIVg and subsequent deprotection with 4N HCl in dioxane. Compound 74 was obtained from a TBTU coupling with nicotinic acid, followed by a Suzuki coupling with 1-ethyl-3-(3-(4,4,5,5-tetramethyl-1,3,2-dioxaborolan-2-yl) benzyl)urea XIVg and subsequent deprotection with 4N HCl in dioxane (Scheme 8).

Scheme 8:

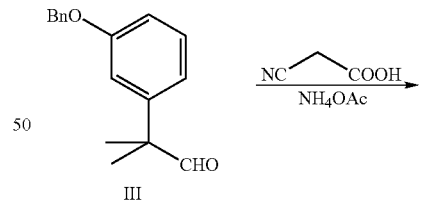

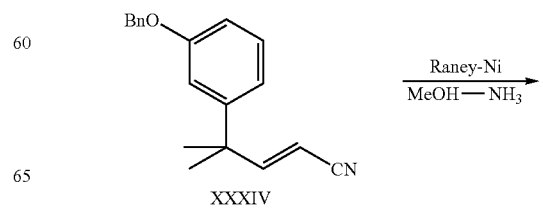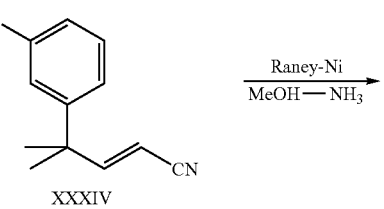

-continued
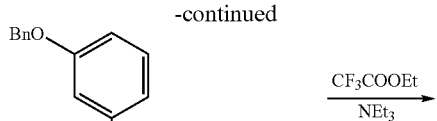
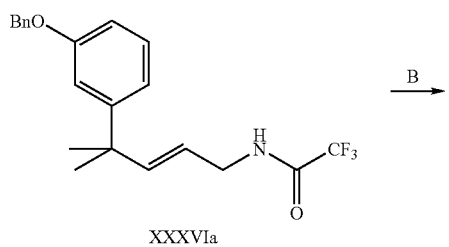
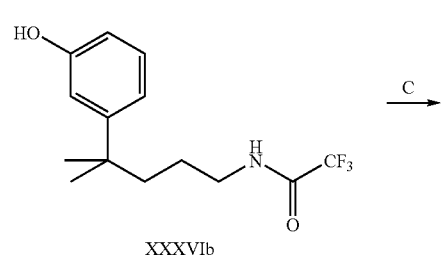
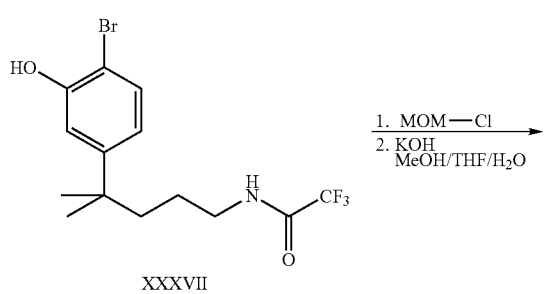
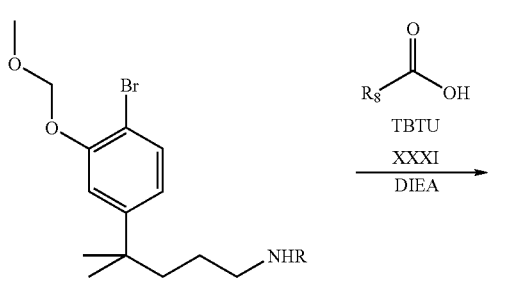
a: R = COCF₃
b: R = H
-continued
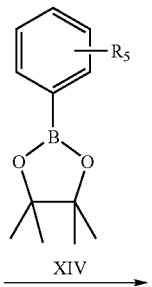
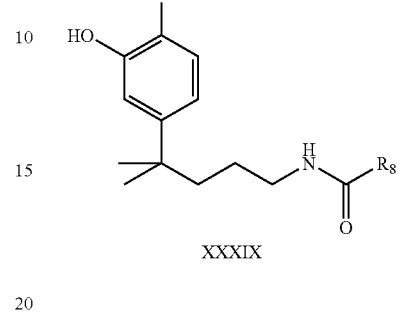
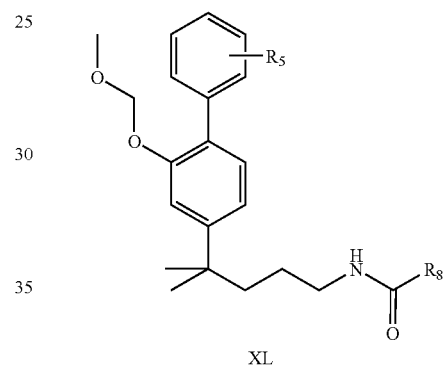
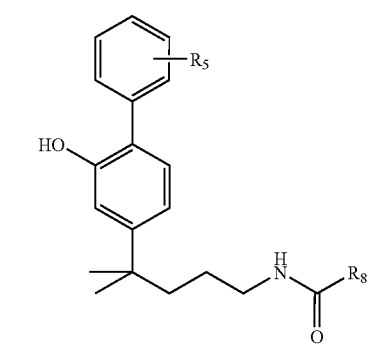
compound 73
R₅ = 3-CH₂NHCONHC₂H₅
R₈ = C(CH₃)₂CH₂NH₂* HCl
compound 74
R₅ = 3-CH₂NHCONHC₂H₅
R₈ = 3-pyridyl* HCl
Compounds 75 and 76 were obtained through methylation of compounds 20 and 35 with methyl iodide in acetonitrile. An LAH-reduction of compounds 20 and 35 yielded amines 77 and 78 respectively (Scheme 9).

Scheme 9:

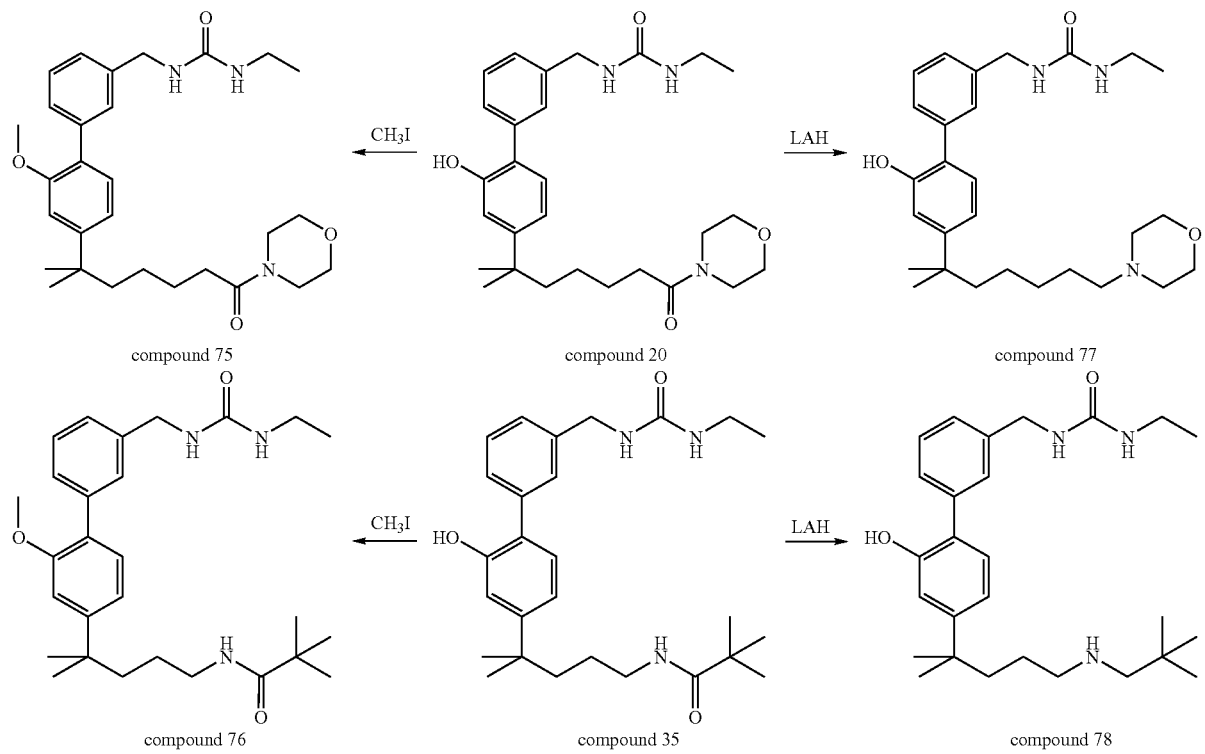

Other features of the invention will become apparent in the course of the following descriptions of exemplary embodiments which are given for illustration of the invention and are not intended to be limiting thereof. The present invention will now be illustrated by reference to the following specific, non-limiting examples. Those skilled in the art of organic synthesis may be aware of still other synthetic routes to the invention compounds. The reagents and intermediates used herein are either commercially available or prepared according to standard literature procedures, unless otherwise described.

EXERIMENTAL PROCEDURES

Materials: All chemicals were reagent grade and unless otherwise specified purchased from Sigma-Aldrich and used without further purification. All reactions, unless otherwise noted, are carried out at atmospheric pressure, room temperature, and in the presence of an air atmosphere. The bold letters over or under reaction arrows in Schemes 1-7 refer to general procedures herein described. LC-MS data were obtained using a Thermo-Finnigan Surveyor HPLC and a Thermo-Finnigan AQA MS using positive or negative electrospray ionization. Program (positive) Solvent A: 10 mM ammonium acetate, pH 4.5, 1% acetonitrile; solvent B: acetonitrile; column: Michrom Bioresources Magic C18 Macro Bullet, detector: PDA λ=220-300 nm. Gradient: 96% A-100% B in 3.2 minutes, hold 100% B for 0.4 minutes. Program (negative) 1 mM ammonium acetate, pH 4.5, 1% acetonitrile; solvent B: acetonitrile; column: Michrom Bioresources Magic C18 Macro Bullet, detector: PDA λ=220-300 nm. Gradient: 96% A-100% B in 3.2 minutes, hold 100% B for 0.4 minutes.

Example 1

Preparation of 2-(3-(Benzyloxy)phenyl)-2-methylpropanenitrile (II)

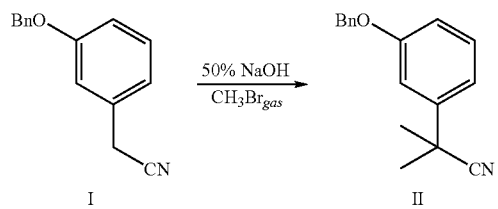

A solution of commercially available nitrile I (83.9 g, 0.38 mol) in DMSO (57 mL) and 50% NaOH solution (120 mL) were simultaneously added to DMSO (425 mL) previously saturated for one hour with bromomethane gas. Bromomethane was continuously bubbled through the reaction mixture during the addition and then for a further 1.5 hours with ice-cooling to maintain the temperature at 50° C. or less. The reaction mixture was added to a 600 mL H$_2$O-600 g ice mixture and then extracted with Et$_2$O (3×800 mL), the ethereal layers were washed with water (1 L) and brine (1 L), dried and concentrated under reduced pressure to give a yellow oil.

The yellow oil was cooled in a dry-ice acetone bath until it solidified and then left to stand at room temperature overnight to afford II as a light yellow crystalline solid (93.59 g, 98%). M+1=252.

Example 2

Preparation of 2-(3-(benzyloxy)phenyl)-2-methylpropanal (III)

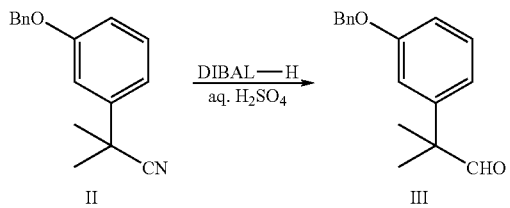

Diisobutylaluminum hydride (300 mL, 0.3 mol of a 1.0 M solution in hexanes) was added dropwise to a cooled (15° C., ice-bath) solution of nitrile II (59.9 g, 0.24 mol) in anhydrous tetrahydrofuran (250 mL). The reaction temperature was maintained at 15-18° C. during the addition. The reaction was then allowed to warm to room temperature and stirred for an additional 2 hours. The reaction was hydrolyzed by addition of a cold solution of conc. $H_2SO_4$ (35.5 mL) in water (117.5 mL) with the temperature maintained at <30° C. The resultant mixture was stirred for a further 2 hours, then filtered, and the filtrate extracted with diethyl ether (2×250 mL), washed with water (300 mL), brine (300 mL), dried and concentrated under reduced pressure to give crude aldehyde III as a light-yellow oil (59.82 g, 98%) which was used without further purification. M+1=255.

Example 3

Preparation of 2-(3-Benzyloxy-phenyl)-2-methyl-propan-1-ol (IV)

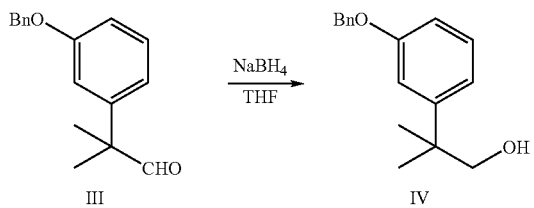

Reduction of III was carried out under standard conditions using $NaBH_4$ in tetrahydrofuran as described by Chaikin and Brown (*J. Am. Chem. Soc.* 1949, 71, 122) to generate IV quantitatively. M+1=257

Example 4

Preparation of (2E, 4E)-Methyl 6-(3-(benzyloxy) phenyl)-6-methylhepta-2,4-dienoate (VIa)

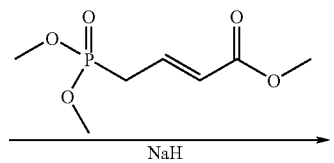

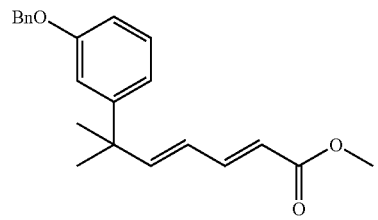

A solution of 4-(dimethoxy-phosphoryl)-but-2-enoic acid methyl ester (27.06 g, 0.13 mol) in anhydrous tetrahydrofuran (92 mL) was added dropwise to a cooled (0° C.), stirred suspension of sodium hydride (5.60 g, 0.14 mol) in anhydrous tetrahydrofuran (110 mL). The resultant red reaction mixture was allowed to stir at room temperature for 50 min then cooled to 0° C. A solution of aldehyde III (27.98 g, 0.11 mol) in dry tetrahydrofuran (75 mL) was added dropwise over a 5-10 min period. The reaction mixture was allowed to stir at room temperature overnight, then poured into a 300 mL ice: 2N HCl (300 mL) mixture. The organic layer was separated, the aqueous layer was extracted with dichloromethane (2×250 mL) and the combined organic extracts were washed with brine (350 mL), dried and concentrated under reduced pressure. The crude product was purified by flash chromatography (eluting first with 10% ethyl acetate/hexane then 20% ethyl acetate/hexane) to yield the α,β-unsaturated ester VIa as a light yellow oil (37.0 g, 80%). M+1=337.

Example 5

Preparation of (2E, 4E)-6-(3-(benzyloxy)-phenyl)-6-methylhepta-2,4-dienoic acid (VIc)

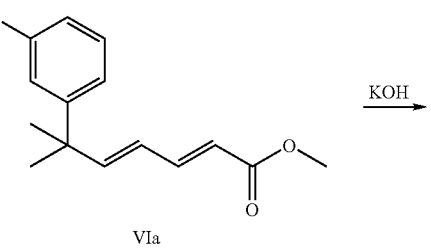

-continued

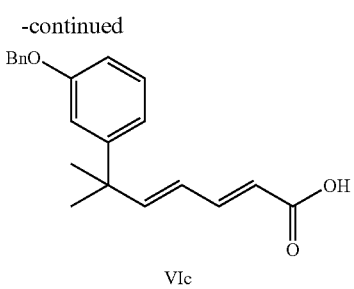

VIc

2N KOH solution (30 mL) was added to a solution of the α,β-unsaturated ester VIa (19.33 g, 57.5 mmol) in methanol (5 mL) and the resultant reaction mixture was heated under reflux overnight. After TLC indicated all the ester had been hydrolyzed, the reaction mixture was concentrated under reduced pressure to remove the methanol and then acidified to pH 1 with concentrated HCl. The acid was extracted with ethyl acetate (100 mL), washed with brine (50 mL), dried and concentrated under reduced pressure to give crude acid VIc as a light-yellow oil (18.54 g, 100%), which was used without further purification. M−1=321.

Example 6

Preparation of (2E, 4E)-6-(3-(Benzyloxy)phenyl)-6-methylhepta-2,4-dienoyl chloride (VId)

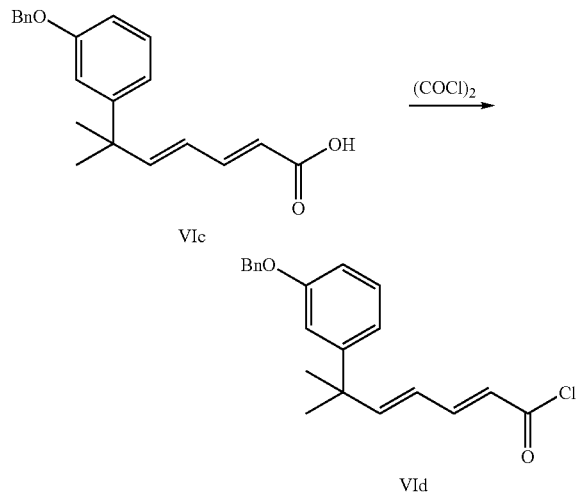

Oxalyl chloride (4.6 mL, 52.7 mmol, 1.2 equiv) was added dropwise to a solution of acid VIc (14.09 g, 43.7 mmol) in anhydrous dichloromethane (40 mL), followed by the addition of 2 drops of anhydrous dimethylformamide. The resultant reaction mixture was then heated under reflux for 1 hour, after which the crude acid chloride was concentrated under reduced pressure to give acid chloride VId quantitatively as a light-yellow liquid, which was used in the next step without further purification. M+1=341.

Example 7

Preparation of 3-[2-(3-Benzyloxy-phenyl)-2-methyl-propoxyl-propionyl chloride (IXf)

3-[2-(3-Benzyloxy-phenyl)-2-methylpropoxy]-propionic acid IXe (prepared from allyl ether IXc (see general procedure A) through reaction with 9-BBN (J. Chen et al. *J. Organomet. Chem.* 1978, 156(1), 213) and subsequent Jones oxidation (J. L. Adad et al. *J. Org. Chem.* 2000, 65, 8582)) was converted to acid chloride IXf quantitatively according to the same procedure as described in Example 6 for the preparation of intermediate IVd. M+1=347.

Example 8

Preparation of (2E, 4E)-6-(3-(Benzyloxy)phenyl)-6-methyl-1-morpholinohepta-2,4-dien-1-one (XI)

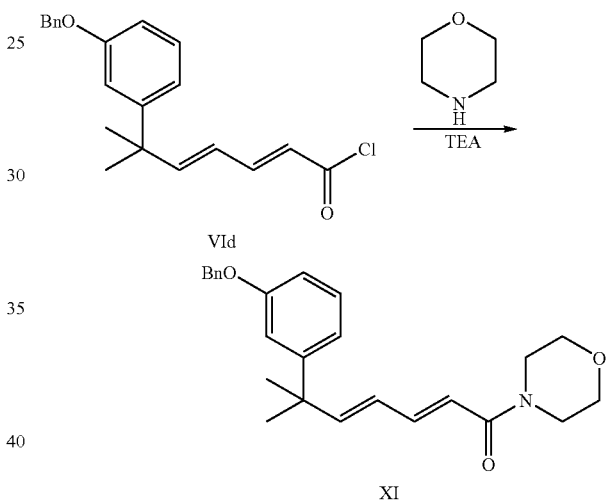

Triethylamine (9.1 mL, 65.3 mmol, 1.5 equiv) was added dropwise to a cooled (0° C.) solution of acid chloride VId (14.90 g, 43.7 mmol) in anhydrous tetrahydrofuran (40 mL), followed by the dropwise addition of morpholine (4.2 mL, 48.2 mmol, 1.1 equiv). The resultant reaction mixture was allowed to stir at room temperature for 3 hours, then diluted with ethyl acetate (50 mL), washed with water (50 mL), sat. NaHCO$_3$ solution (2×50 mL), 1N HCl solution (2×50 mL), and brine (75 mL), dried and concentrated under reduced pressure. The crude morpholino amide was purified by flash chromatography (eluting with 60% ethyl acetate/hexanes then 80% ethyl acetate/hexanes) to give amide XI as a colorless oil (16.25 g, 95%). M+1=392.

Example 9

Preparation of 3-12-(3-Benzyloxy-phenyl)-2-methyl-propoxyl-1-morpholin-4-yl-propan-1-one (IX)

3-[2-(3-Benzyloxy-phenyl)-2-methyl-propoxy]-1-morpholin-4-yl-propan-1-one IXg was prepared from acid chloride IXf according to the same procedure as described for amide XI (Example 8). M+1=398.

Example 10

Preparation of 6-(3-Hydroxyphenyl)-6-methyl-1-morpholinoheptan-1-one (Xa)

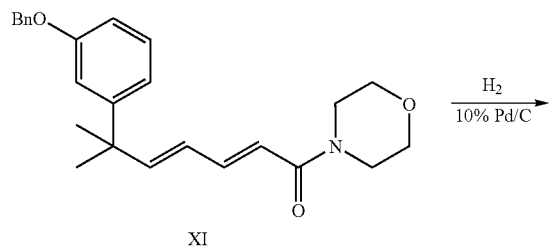

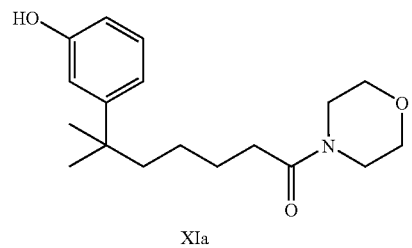

A solution of α,β-unsaturated amide XI (12.96 g, 33.1 mmol) in ethanol (100 mL) was hydrogenated with 3 g of 10% Pd/C on the Parr hydrogenator overnight at 60 psig $H_2$. After TLC indicated that the reaction had gone to completion, the reaction was evacuated and filtered through a plug of silica and washed with ethyl acetate. The crude phenol was concentrated in vacuo and purified by flash chromatography (50% ethyl acetate/Hexane to 70% ethyl acetate/Hexane then finally eluting with 90% ethyl acetate/Hexane) to give phenol XIa as a white crystalline solid (9.44 g, 93%). M+1=306.

Example 11

Preparation of 6-(4-Bromo-3-hydroxyphenyl)-6-methyl-1-morpholin-4-yl-heptan-1-one (XII)

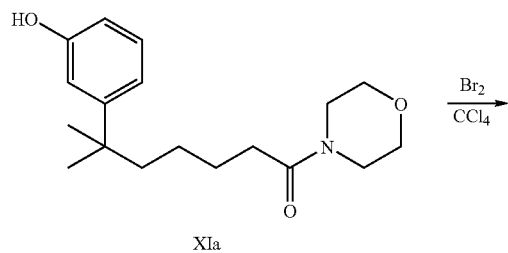

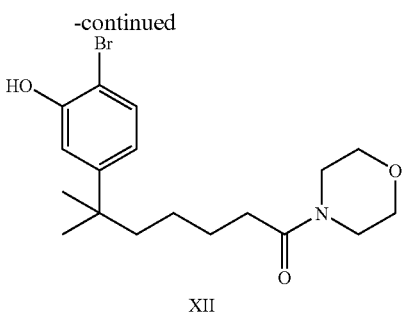

Bromination of 9 g XIa was carried out in 200 mL carbon tetrachloride and 50 mL dichloromethane using 0.95 equivalents of bromine to give 7.73 g XII as a white solid (68%) after workup (see General Procedure C). M+1=385.

General Procedures for Solution Phase Reactions:

A. Alkylation

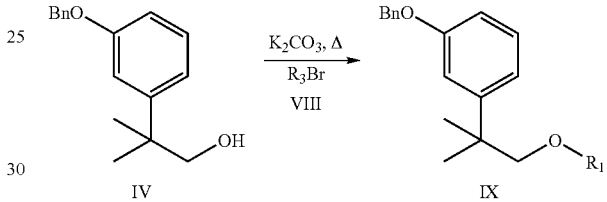

Protected phenol IV (Example 3, 1 equiv) was dissolved in dimethylformamide (100 mL), $K_2CO_3$ (4 equiv) and the corresponding alkyl or allyl bromide (2 equiv) were added, and the mixture was heated for 4-8 hours at 70-90° C. The solution was decanted, the crude mixture was concentrated under reduced pressure, and the residue purified by flash chromatography (ethyl acetate/hexane).

Compounds generated following this procedure:
1-Benzyloxy-3-(2-butoxy-1,1-dimethyl-ethyl)-benzene IXa,
1-benzyloxy-3-[2-(2-methoxy-ethoxy)-1,1-dimethyl-ethyl]-benzene IXb,
1-(2-allyloxy-1,1-dimethyl-ethyl)-3-benzyloxy-benzene IXc.

B. Deprotection with $H_2$

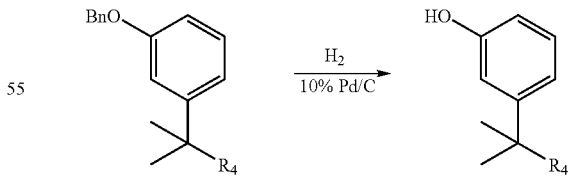

A solution of protected intermediate phenol from General Procedure A (1 equiv) in ethanol (100 mL) was hydrogenated with 10% Pd/C on the Parr hydrogenator overnight at 60 psig $H_2$. The reaction was evacuated and filtered through a plug of silica and washed with ethyl acetate. The crude phenol was concentrated in vacuo and purified by flash chromatography (ethyl acetate/Hexane) with yields ranging from 68-91%.

R4 =

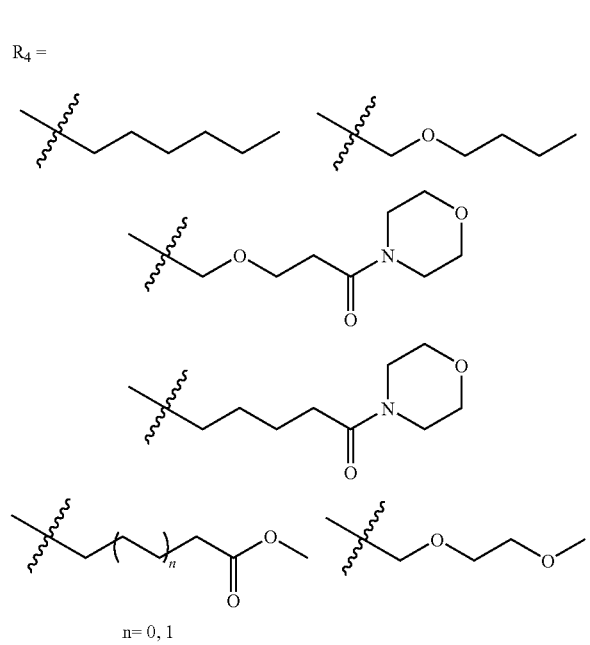

n= 0, 1

C. Bromination

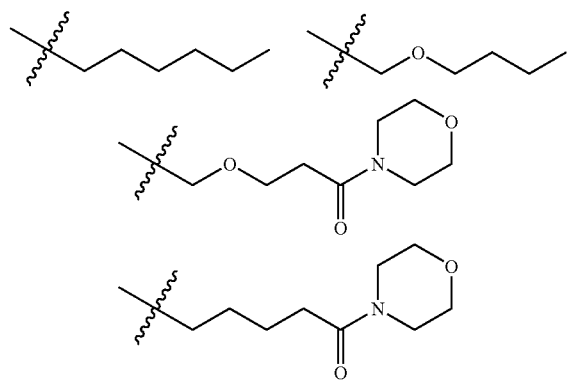

Intermediate phenol (1 equiv) from General Procedure B was dissolved in carbon tetrachloride (80 mL) and bromine (0.95 equiv) in carbon tetrachloride (20 mL) was added dropwise. The mixture was stirred at room temperature for 4 hours. The crude mixture was concentrated in vacuo and purified by flash chromatography (ethyl acetate/hexane) yielding 51-89% of desired bromination products.

R4 =

n= 0, 1

General Procedures for Solid Phase Reactions:

D. Resin Loading

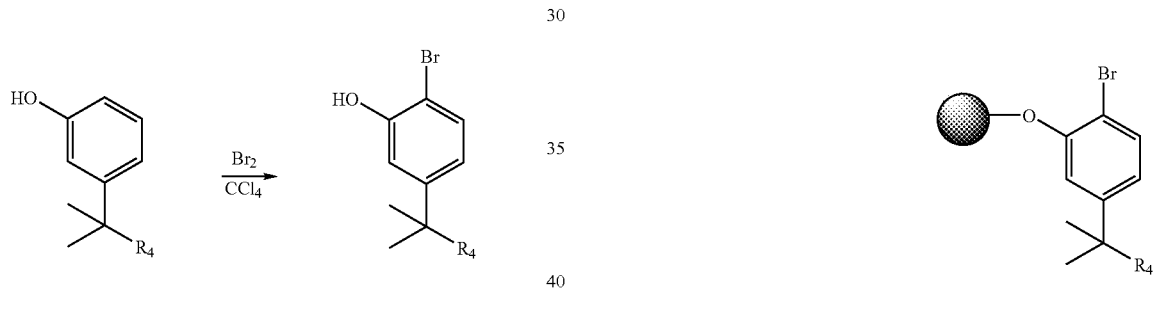

XIII

PL-Bromo-Wang resin (1 g, 1.3 mmol/g, 150-300 μm, batch MIR/12/238) was washed twice with dichloromethane, suspended in 10 mL dimethylformamide and K$_2$CO$_3$ (4-10 equiv) was added followed by phenol VIa, VIb, VIc, Xa, Xb, Xc or XII (2-4 equiv). The mixture was heated 12-16 hours at 70° C. Then the resin was filtered, washed with dimethylformamide, dichloromethane, methanol/H$_2$O, methanol/dichloromethane, dichloromethane and used for the subsequent Suzuki coupling step.

E. Suzuki Coupling

XIII

-continued

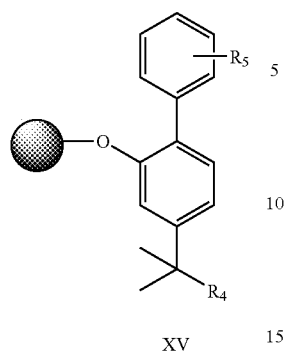

XV

Resin bound intermediate XIII was suspended in dimethylformamide, boronate XIV (3-5 equiv) was added followed by the catalyst Pd(PPh$_3$)$_4$ (10-20 mol %) and base Cs$_2$CO$_3$ (10 equiv). The mixture was heated to 95° C. for 24 hours. Then resin XV was filtered, washed with dimethylformamide, dichloromethane, methanol/H$_2$O, methanol/dichloromethane, dichloromethane and used for the subsequent step.

R$_4$ =

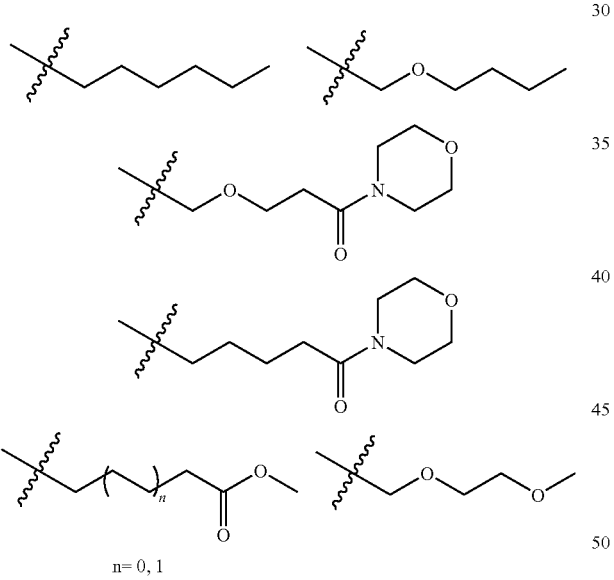

n = 0, 1

Boronates and boronic acids XIV used:

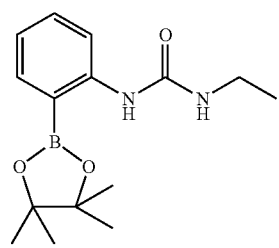

XIVa

-continued

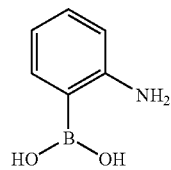

XIVb

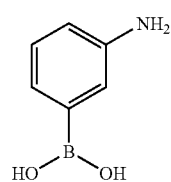

XIVc

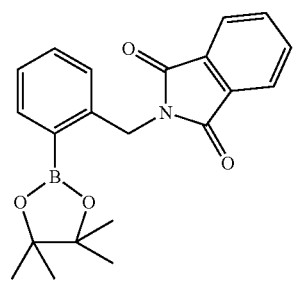

XIVd

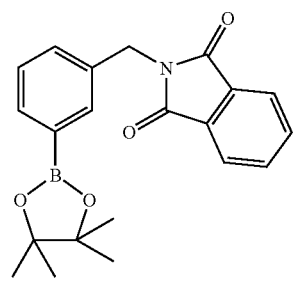

XIVe

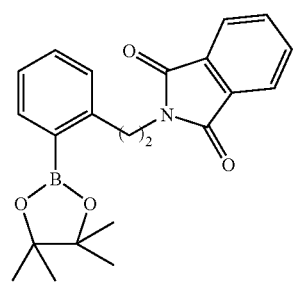

XIVf

F. Phthalimide Cleavage

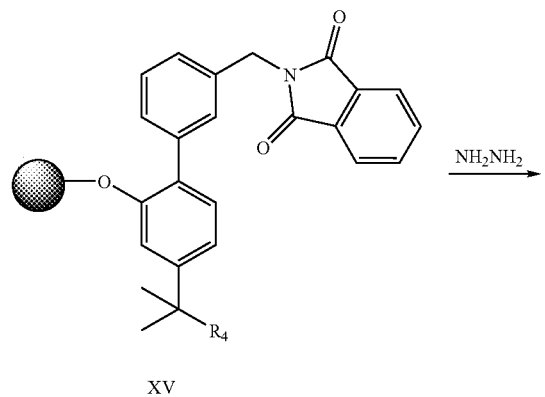

XV

G. Urea Formation

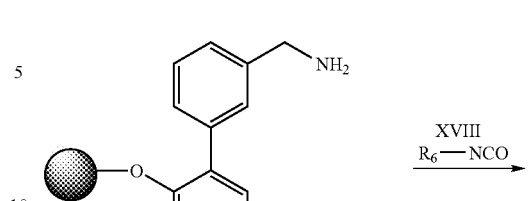

XVII

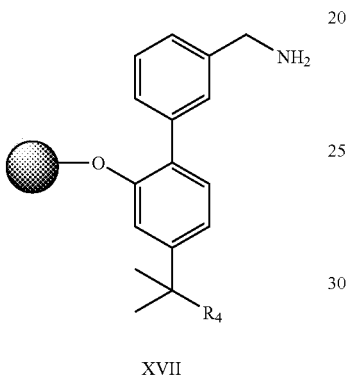

XVII

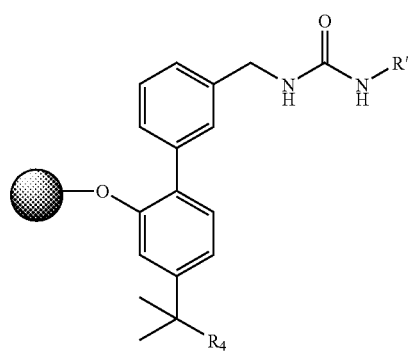

XIX

Resin bound Suzuki product XVd, XVe or XVf was washed with dry tetrahydrofuran. Deprotection was carried out with fresh 0.5M-1.0M solution of hydrazine in tetrahydrofuran for 24 hours at room temperature. Product resin XVII was filtered, washed with tetrahydrofuran, dichloromethane, methanol/dichloromethane, dichloromethane and used for the subsequent step.

Resin bound amine XVII was suspended in dichloromethane and the corresponding isocyanate XVIII (20 equiv) was added slowly. The mixture was shaken overnight. Product resin XIX was filtered, washed with dichloromethane, methanol/dichloromethane, dichloromethane several times and used in the subsequent step.

Isocyanates $R_6$NCO XVIII:

$R_4 =$

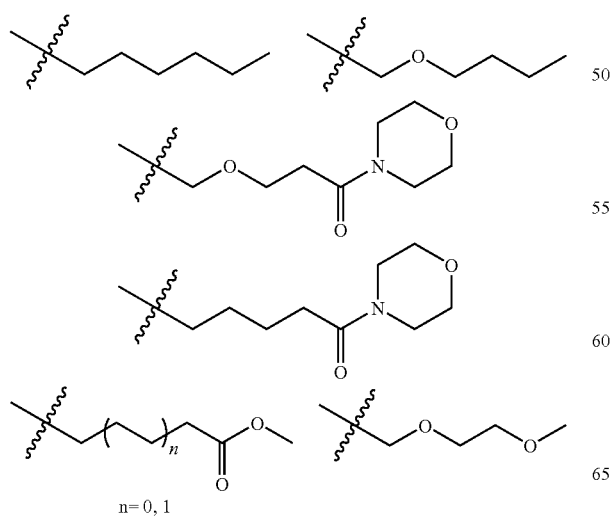

n = 0, 1

-continued

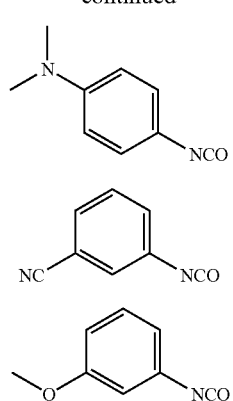

H. Cleavage from Resin

Resin containing final product was suspended in TFA/dichloromethane (1:1) for 2 hours at room temperature, then filtered, washed once with dichloromethane. The combined filtrates were evaporated. Crude purities of the final compounds prepared were between 75-95%. Further purification was carried out using flash chromatography or preparative HPLC.

I. Amide Formation

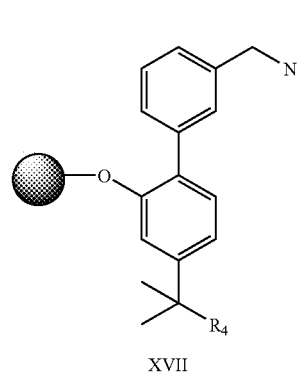
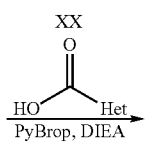

XVII

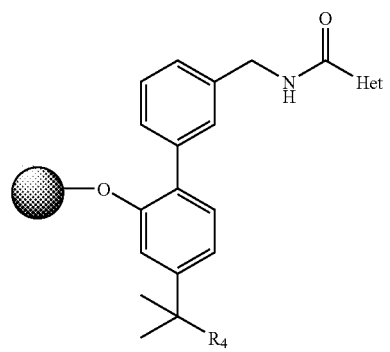

XXI

Resin bound amine XVII was suspended in dichloromethane followed by DIEA (8 equiv), heterocyclic carboxylic acid XX (4 equiv) and PyBrop (4 equiv). The mixture was shaken overnight. Product resin XXI was filtered, washed with dichloromethane, methanol/dichloromethane, dichloromethane several times and used in the subsequent step.

Carboxylic Acids Het-COOH XX:

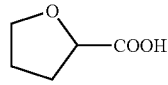  a

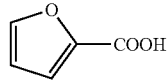  b

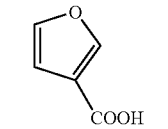  c

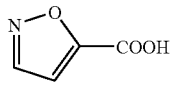  d

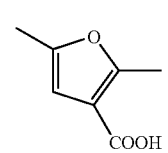  e

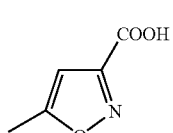  f

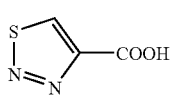  g

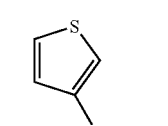  h

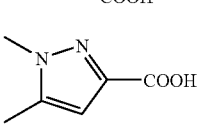  i

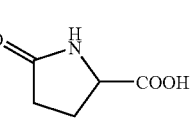  j

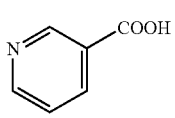  k

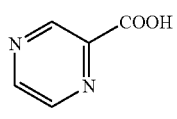  l

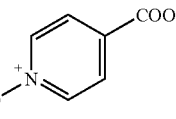  m

-continued

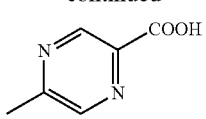

J. Sulfonamide Formation

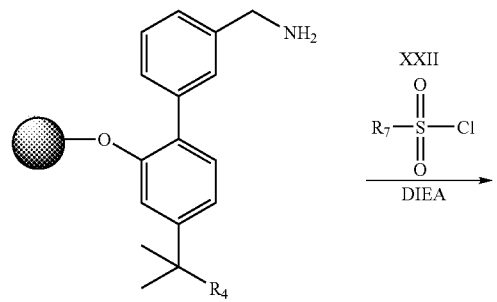

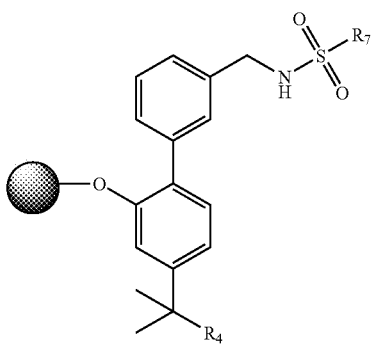

Resin bound amine XVII was suspended in dichloromethane followed by DIEA (8 equiv). The sulfonyl chloride XXII (4 equiv) was added slowly. The mixture was shaken overnight. Product resin XXIII was filtered, washed with dichloromethane, methanol/dichloromethane, dichloromethane several times and used in the subsequent step.

Sulfonamide $R_7SO_2Cl$ XXII:

Methanesulfonyl chloride

Example 12

Preparation of 1-[4'-(1,1-Dimethyl-heptyl)-2'-hydroxy-biphenyl-2-yl]-3-ethyl-urea (1)

Bromo-phenol VIIa (11.3 g, 37.92 mmol, 3 equiv.) in 150 mL dimethylformamide was bound to resin (9.72 g, 12.64 mmol) following General Procedure D using 10.5 g $K_2CO_3$ (75.84 mmol, 6 equiv.) as base. 200 mg (0.26 mmol) of the produced resin bound intermediate VIII was used for the Suzuki coupling according to General Procedure E with boronate XIVa (see Scheme 5, 0.75 g, 2.6 mmol, 10 equiv.) $Cs_2CO_3$ (1.27 g, 3.9 mmol, 15 equiv.) and $Pd(PPh_3)_4$ (0.06 g, 20 mol %) in 5 mL dimethylformamide. Final compound was cleaved from resin following General Procedure H and purified by flash chromatography (hexanes/ethyl acetate 3:2) yielding 29 mg solid (29%) with M+1=383.

Example 13

Preparation of N-[4'-(1,1-Dimethyl-heptyl)-2'-hydroxy-biphenyl-2-yl]-methane sulfonamide (2)

The resin bound intermediate from bromo-phenol VIIa (obtained via General Procedure D, 200 mg, 0.26 mmol) was used for the Suzuki coupling according to General Procedure E with boronate XIVb, followed by sulfonamide formation according to General Procedure J with methanesulfonyl chloride. Step J was repeated to ensure complete conversion, then the final Compound 2 was formed by cleavage from resin according to General Procedure H and purified by preparative HPLC (gradient $H_2O$/acetonitrile 10-100%). Yield 7 mg (6.9%), M+1=390.

Example 14

Preparation of N-[4'-(1,1-Dimethyl-heptyl)-2'-hydroxy-biphenyl-3-yl]-methane sulfonamide (3)

Compound 3 was obtained from bromophenol VIIa, via reaction of resin bound intermediate XIII with boronate XIVc and methanesulfonyl chloride using General Procedures D, E, J and H as described in Example 13 for the preparation of compound 2. Yield 3 mg (3%), M+1=390.

Example 15

Preparation of 6-(2-Hydroxy-3'-methanesulfonylamino-biphenyl-4-yl)-6-methyl-heptanoic acid methyl ester (4)

Compound 4 was obtained from the resin bound bromophenol of VIIb, via reaction of resin bound intermediate XIII with boronate XIVc and methanesulfonyl chloride using General Procedures D, E, J and H as described in Example 14 for the preparation of Compound 3. Yield 44 mg (40%), M+1=420.

Example 16

Preparation of 1-[4'-(1,1-Dimethyl-heptyl)-2'-hydroxy-biphenyl-3-ylmethyl]-3-ethyl-urea (5)

The resin bound intermediate XIII of Bromo-phenol VIIa ((200 mg, 0.26 mmol), obtained according to General Procedure D and Example 1) was used for the Suzuki coupling (General Procedure E) with boronate XIVe (see Scheme 5, 0.72 g, 1.3 mmol, 5 equiv.) $Cs_2CO_3$ (0.85 g, 2.6 mmol, 10 equiv.) and $Pd(PPh_3)_4$ (20 mol%) in 5 mL dimethylformamide, followed by General Procedures F (10 mL 1N $NH_2NH_2$ in tetrahydrofuran), G (10 mL dichloromethane, 0.5 mL EtNCO) and H (5 mL TFA/5 mL dichloromethane). The final product 5 was purified by flash chromatography (1% methanol to 5% methanol in ethyl acetate). Yield 12 mg (11.6%). M+1=397.

Example 17

Preparation of 1-[4'-(1,1-Dimethyl-heptyl)-2'-hydroxy-biphenyl-2-ylme-thyl]-3-ethyl-urea (6)

Compound 6 was obtained from Bromo-phenol VIIa, via reaction of resin bound intermediate XIII with boronate XIVd, and ethyl isocyanate using General Procedures D-H as described in Example 16 for the preparation of Compound 5. Yield 25 mg (24 %). M+1=397

Example 18

Preparation of 1-12-[4'-(1,1-Dimethyl-heptyl)-2'-hydroxy-biphenyl-2-yl]-ethyl}-3-ethyl-urea (7)

Compound 7 was obtained from Bromo-phenol VIIa, via reaction of resin bound intermediate XIII with boronate XIVf (n=2), and ethyl isocyanate using General Procedures D-H as described in Example 16 for the preparation of Compound 5. Yield 15 mg (14%). M+1=411.

Example 19

Preparation of N-[4'-(1,1-Dimethyl-heptyl)-2'-hydroxy-biphenyl-3-ylmethyl]-methane sulfonamide (8)

Compound 8 was obtained from Bromo-phenol VIIa, via reaction of resin bound intermediate XIII with boronate XIVe and methanesulfonyl chloride using General Procedures D, E, F, J and H as described in Example 13 for the preparation of Compound 2. Yield 14 mg (13 %). M+1=404.

Example 20

Preparation of N-[4'-(1,1-Dimethyl-heptyl)-2'-hydroxy-biphenyl-2-ylmethyl]-methane sulfonamide (9)

Compound 9 was obtained from Bromo-phenol VIIa, via reaction of resin bound intermediate XIII with boronate XIVd and methanesulfonyl chloride using General Procedures D, E, F, J, and H as described in Example 13 for the preparation of Compound 2. Yield 30 mg (28.6 %). M+1=404.

Example 21

Preparation of N-{2-[4'-(1,1-Dimethyl-heptyl)-2'-hydroxy-biphenyl-2-yl]-ethyl}-methane sulfonamide (10)

Compound 10 was obtained from Bromo-phenol VIIa, via reaction of resin bound intermediate XIII with boronate XIVd (n=2) and methanesulfonyl chloride using General Procedures D, E, F, J, and H as described in Example 13 for the preparation of Compound 2. Yield 16 mg (14.7 %). M+1=418.

Example 22

Preparation of 1-[4'-[1,1-Dimethyl-2-(3-morpholin-4-yl-3-oxo-propoxy)-ethyl]-2'-hydroxy-bi-phenyl-3-yl-methyl}-3-ethyl-urea (11)

Bromo-phenol Xc (1.5 g, 3.9 mmol, 2.2 equiv.) in 15 mL dimethylformamide was bound to resin (1.36 g, 1.77 mmol) following General Procedures D using 1.47 g $K_2CO_3$ (10.62 mmol, 6 equiv.) as base. Suzuki coupling was carried out according to General Procedure E with boronate XIVe (see Scheme 5, 2.57 g, 7.08 mmol, 4 equiv.) $Cs_2CO_3$ (5.77 g, 17.7 mmol, 10 equiv.), $Pd(PPh_3)_4$ (0.41 g, 20 mol %) in 20 mL dimethylformamide, followed by General Procedures F (10 mL 1N $NH_2NH_2$ in tetrahydrofuran), G (10 mL dichloromethane, 0.5 mL EtNCO) and H (5 mL TFA/5 mL dichloromethane). The final product 11 was purified by flash chromatography (1% methanol to 5% methanol in ethyl acetate). Overall Yield 117 mg (6%). M+1=484.

Example 23

Preparation of 1-[4'-(2-Butoxy-1,1-dimethyl-ethyl)-2'-hydroxy-biphenyl-2-ylmethyl]-3-ethyl-urea (12)

Compound 12 was obtained from Bromo-phenol Xa, via reaction of resin bound intermediate XIII with boronate XIVd, and ethyl isocyanate using General Procedures D-H as described in Example 22 for the preparation of Compound 11. Yield 206 mg (13%). M+1=399.

Example 24

Preparation of 1-[4'-(2-Butoxy-1,1-dimethyl-ethyl)-2'-hydroxy-biphenyl-2-ylmethyl]-3-propyl-urea (13)

Compound 13 was obtained from Bromo-phenol Xa, via reaction of resin bound intermediate XIII with boronate XIVd, and n-propyl isocyanate using General Procedures D-H as described in Example 22 for the preparation of Compound 11. Yield 185 mg (11%). M+1=413.

Example 25

Preparation of 1-[4'-(2-Butoxy-1,1-dimethyl-ethyl)-2'-hydroxy-biphenyl-3-ylmethyl]-3-ethyl-urea (14)

Compound 14 was obtained from Bromo-phenol Xa, via reaction of resin bound intermediate XIII with boronate XIVe, and ethyl isocyanate using General Procedures D-H as described in Example 22 for the preparation of Compound 11. Yield 152 mg (9.8%). M+1=399.

Example 26

Preparation of 1-[4'-(2-Butoxy-1,1-dimethyl-ethyl)-2'-hydroxy-biphenyl-3-ylmethyl]-3-propyl-urea (15)

Compound 15 was obtained from Bromo-phenol Xa, via reaction of resin bound intermediate XIII with XIVe, and n-propyl isocyanate using General Procedures D-H as described in Example 22 for the preparation of Compound 11. Yield 178 mg (11%). M+1=413.

Example 27

Preparation of 1-Ethyl-3-{2'-hydroxy-4'-[2-(2-methoxy-ethoxy)-1,1-dimethyl-ethyl]-biphenyl-2-ylmethyl}-urea (16)

Compound 16 was obtained from Bromo-phenol Xb, via reaction of resin bound intermediate XIII with boronate XIVd, and ethyl isocyanate using General Procedures D-H as described in Example 22 for the preparation of Compound 11. Yield 119 mg (7.6%). M+1=401.

Example 28

Preparation of 1-Ethyl-3-{2'-hydroxy-4'-[2-(2-methoxy-ethoxy)-1,1-dimethyl-ethyl]-biphenyl-3-ylmethyl}-urea (17)

Compound 17 was obtained from Bromo-phenol Xb, via reaction of resin bound intermediate XIII with boronate XIVe, and ethyl isocyanate using General Procedures D-H as described in Example 22 for the preparation of Compound 11. Yield 394 mg (25%). M+1=401.

Example 29

Preparation of 1-[4'-(1,1-Dimethyl-6-morpholin-4-yl-6-oxo-hexyl)-2'-hydroxy-biphenyl-2-ylmethyl]-3-ethyl-urea (18)

Compound 18 was obtained from Bromo-phenol XII, via reaction of resin bound intermediate XIII with boronate XIVd, and ethyl isocyanate using General Procedures D-H as described in Example 22 for the preparation of Compound 11. Yield 234 mg (12.5%). M+1=482.

Example 30

Preparation of 1-[4'-(1,1-Dimethyl-6-morpholin-4-yl-6-oxo-hex-4-enyl)-2'-hydroxy-biphenyl-2-yl-methyl]-3-ethyl-urea (19)

Compound 19 was obtained as a minor product when Compound 18 was purified. It was formed from incompletely hydrogenated precursor XI carried through steps C-H. Yield 4 mg (0.2%). M+1=480.

Example 31

Preparation of 1-[4'-(1,1-Dimethyl-6-morpholin-4-yl-6-oxo-hexyl)-2'-hydroxy-biphenyl-3-yl-methyl]-3-ethyl-urea (20)

Compound 20 was obtained from Bromo-phenol XII, via reaction of resin bound intermediate XIII with boronate XIVe, and ethyl isocyanate using General Procedures D-H as described in Example 22 for the preparation of Compound 11. Yield 791 mg (42%). M+1=482

Example 32

Preparation of Compounds 21-34

Compounds 21-34 were part of a parallel set prepared in library plate format according to General Procedure K, outlined below.

K. General Procedure for Plate Preparation—Ureas XIX

Resin bound deprotected biarylphenol XVII (prepared from Bromo-phenol XII, boronates XIVd and XIVe, following general procedures D-F) were distributed into a 96 well filterplate, 10 mg of resin (0.013 mmol) per well.

Resins XVII Used:

compounds 21-27

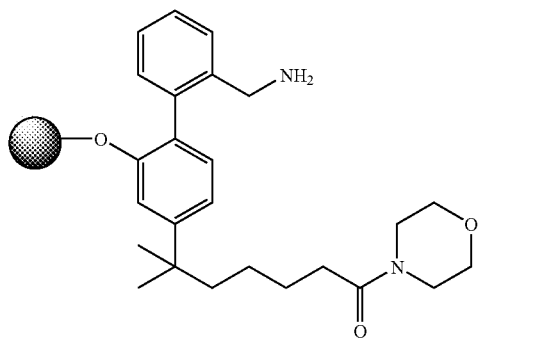

compounds 28-34

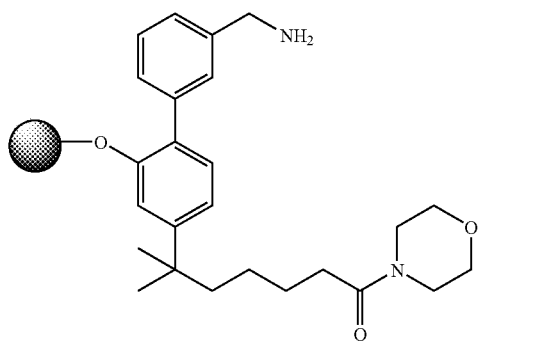

To the resin 400 µl of dichloromethane was added, followed by 0.25 mmol (19 equiv) of isocyanate XVIII a, XVIIId -XVIIIi. The plate was shaken at room temperature for 24 hours, then drained and washed with dichloromethane, methanol/dichloromethane, dimethylformamide, methanol/dichloromethane and dichloromethane. The compounds were cleaved with TPA/dichloromethane (600 µl, 1:1) into a 96 deep well plate and submitted for testing without further purification. (Mass spec results obtained are shown in Table 4).

Isocyanates $R_6NCO$ XVIII:

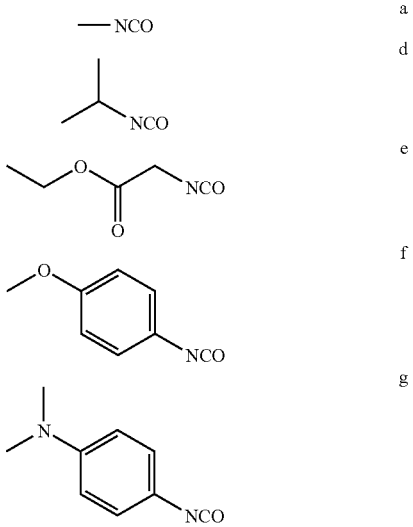

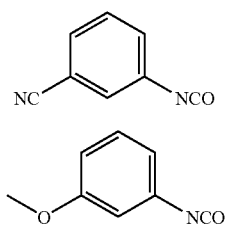

Example 33

Preparation of N-(4-{3'-[(3-Ethyl-ureido)-methyl]-2-hydroxy-biphenyl-4-yl}-4-methyl-pentyl)-2,2-dimethyl-propionamide (35)

Bromo-phenol XII (Scheme 4, 5.29 g, 17.55 mmol, 3 equiv.) in 50 mL dimethylformamide was bound to resin (4.5 g, 5.85 mmol) following General Procedure D using 7.28 g $K_2CO_3$ (52.65 mmol, 9 equiv.) as base to form intermediate XXIV.

Ester Reduction

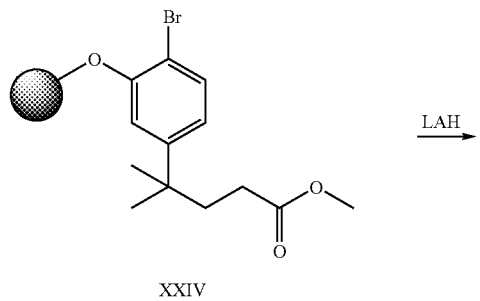

XXIV

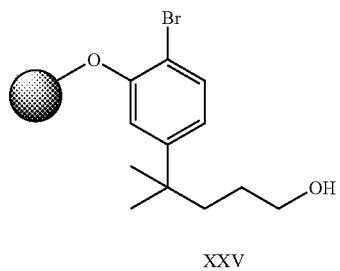

XXV

Resin bound ester XXIV (4.5 g, 5.85 mmol) was washed with dry tetrahydrofuran twice, suspended in 50 mL dry tetrahydrofuran under $N_2$ and cooled to 0° C. Slowly, LAH (1N in tetrahydrofuran, 50 mL) was added and the mixture kept cold for 1 hour. Resin XXV was filtered carefully, then washed with dry tetrahydrofuran (3×), tetrahydrofuran/methanol (3×), tetrahydrofuran (3×), dichloromethane (3×) and used in the subsequent step.

Mitsunobu Coupling

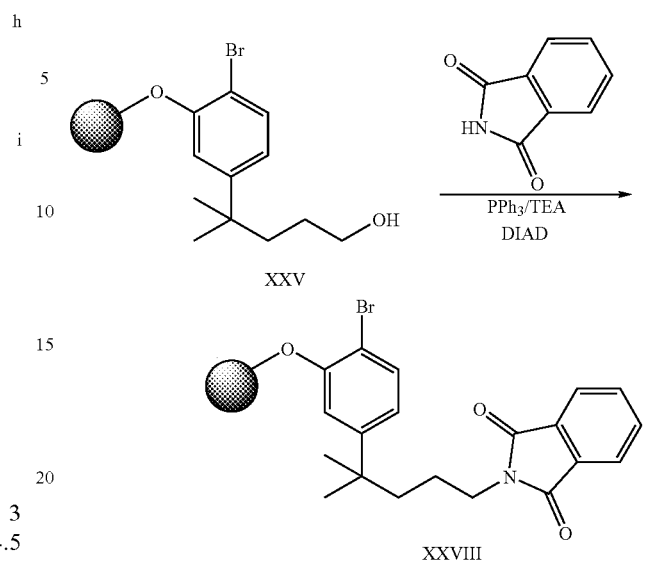

XXVIII

A solution of 8.61 g phthalimide (58.5 mmol, 10 equiv), 7.67 g triphenylphosphine (29.25 mmol, 5 equiv) and 4.3 mL TEA (29.25 mmol, 5 equiv) in 100 mL dry tetrahydrofuran was added to resin bound XXV and shaken for 10 minutes. A solution of 5.76 mL (58.5 mmol, 10 equiv) DIAD in 20 mL dry tetrahydrofuran was added dropwise. The mixture was shaken overnight at room temperature. Resin XXVIII was filtered, washed with tetrahydrofuran, dichloromethane, methanol/dichloromethane and dichloromethane several times and used in the subsequent step.

The phthalimide group of Resin XXVIII was removed following General Procedure F using $NH_2NH_2$ (1M in tetrahydrofuran, 50 mL) to give amine resin XXIX.

Amide Formation

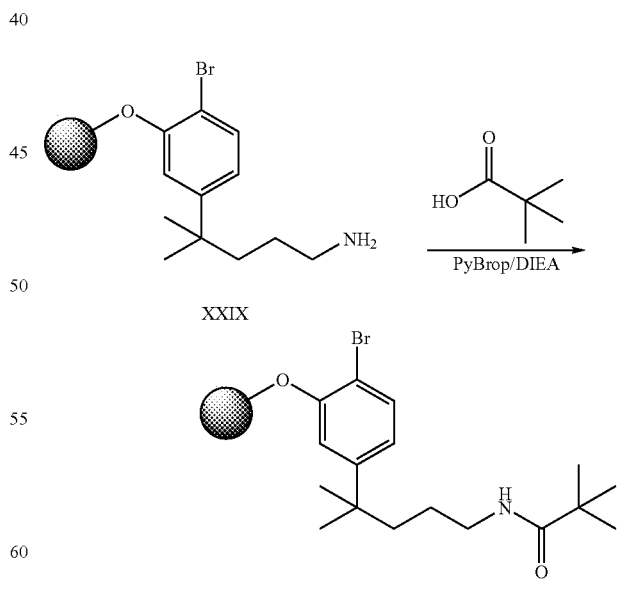

XXIX

XXXIV

Resin bound amine XXIX (1.5 g, 1.95 mmol) was suspended in 15 mL dry dichloromethane, 2.72 mL (15.6 mmol, 8 equiv.) DIEA was added followed by 0.8 g (7.8 mmol, 4 equiv.) of pivalic acid and 3.64 g (7.8 mmol, 4 equiv.) of PyBrop. The mixture was shaken overnight at room temperature. Amido resin XXXIV was filtered, washed with dichloromethane, dimethylformamide, methanol/dichloromethane and dichloromethane several times and used in the subsequent Suzuki coupling step. The Suzuki coupling with boronate XIVe, phthalimide cleavage, urea formation with ethyl isocyanate and resin cleavage steps were carried out similarly using General Procedures D-H as described in Example 22 for the preparation of Compound 11. Purification by flash chromatography provided Compound 35 as white solid (183 mg, 21 % yield). M+1=454.

Example 34

Preparation of 1-(4-{2'-[(3-Ethyl-ureido)-methyl]-2-hydroxy-biphenyl-4-yl}-4-methyl-pentyl)-3-isopropyl-urea (36)

Resin bound amine XXIX (1.5 g, 1.95 mmol, obtained as described in Example 33) was suspended in 15 mL dry dichloromethane and isopropyl isocyanate (1.68 mL, 20 mmol, ~10 equiv.) was added. The mixture was shaken overnight at room temperature. The resin was filtered, washed with dichloromethane, dimethylformamide, methanol/dichloromethane and dichloromethane several times and used in the Suzuki coupling step. The Suzuki coupling with boronate XIVd, phthalimide cleavage, urea formation with isopropyl isocyanate and resin cleavage steps were carried out according to General Procedures E-H similarly to the reactions described in Example 22 for the preparation of Compound 11. Purification by flash chromatography provided Compound 36 as white powder (14 mg, 1.6 % yield). M+1=455.

Example 35

Preparation of 1-(4-{3'-[(3-Ethyl-ureido)-methyl]-2-hydroxy-biphenyl-4-yl}-4-methyl-pentyl)-3-isopropyl-urea (37)

Compound 37 was obtained from Bromo-phenol XXIX, via reaction of resin bound intermediate XIII with boronate XIVe, and ethyl isocyanate using General Procedures D-H as described in Example 34 for the preparation of Compound 36. (21 mg, 3 % yield). M+1=455

Compounds 38 and 39 were isolated as minor products while Examples 36 and 37 were purified. Compounds 38 and 39 were formed from unconverted resin bound alcohol XXV (Mitsunobu reaction to XXVIII was not complete, see scheme 6) with ethyl isocyanate and carried through steps E-H as described in Example 34 for the preparation of Compound 36.

Example 38

Preparation of Morpholine-4-carboxylic acid(4-{3'-[(3-ethyl-ureido)-methyl]-2-hydroxy-biphenyl-4-yl}-4-methyl-pentyl)-amide (40)

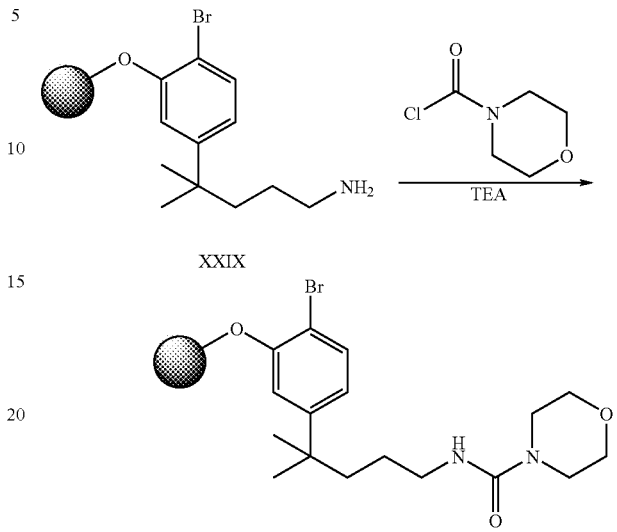

Resin bound amine XXIX (1.5 g, 1.95 mmol, obtained as described in Example 33) was suspended in 15 mL dry dimethylformamide, 4.07 mL (29 mmol, 15 equiv.). TEA was added and the mixture cooled down to 0° C. 4-Morpholinylcarbonyl chloride (1.75 g, 11.7 mmol, 6 mmol) was added slowly and the mixture shaken overnight at room temperature. Resin XXIVb was filtered, washed with dichloromethane, dimethylformamide, methanol/dichloromethane and dichloromethane several times and used in the Suzuki coupling step. The Suzuki coupling with boronate XIVe, phthalimide cleavage, urea formation and resin cleavage steps were carried out similarly using General Procedures D-H as described in Example 22 for the preparation of Compound 11. Purification by flash chromatography provided Compound 40 as off-white solid (92 mg, 10 % yield). M+1=483.

Example 39
Preparation of Compounds 41-70

Compounds 41-70 were part of a parallel set prepared in library plate format according to General Procedure L, outlined below.

L. General Procedure for Plate Preparation—Amide Formation XXI:

Resin bound deprotected biarylphenol XVII (prepared from intermediate XII, boronates XIVd and XIVe, following general procedures D-F) was distributed into a 96 well plate, 10 mg of resin (0.013 mmol) per well.

compounds 42-55

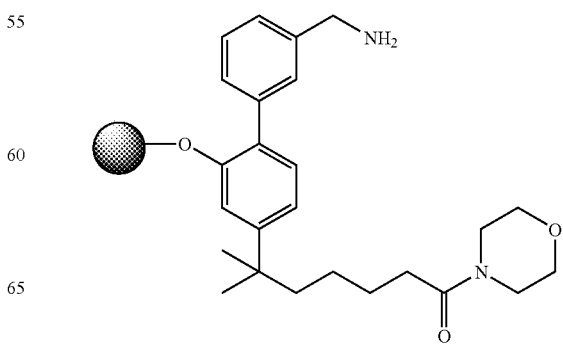

compounds 56-70

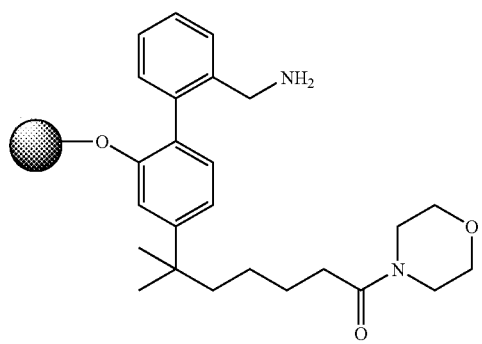

To the resin 400 µl of dichloromethane was added, followed by 100 µl of DIEA, followed by 0.13 mmol (10 equiv) of heterocyclic carboxylic acid XXa-XXn was added followed by 61 mg (0.13 mmol, 10 equiv) of PyBrop. The plate was shaken at room temperature for 24 hours, then drained and washed with dichloromethane, methanol/dichloromethane, dimethylformamide, methanol/dichloromethane and dichloromethane. The compounds were cleaved with TFA/dichloromethane (600 µl, 1:1) into a 96 deep well plate and submitted for testing without further purification. (Mass spec results obtained are shown in Table 4).

a
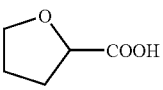

b
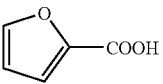

c
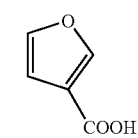

d
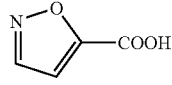

e
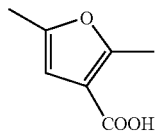

f
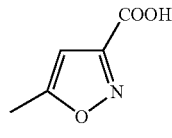

g
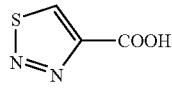

h
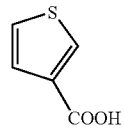

i
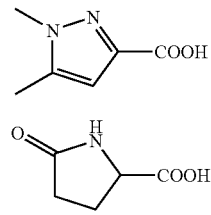

j
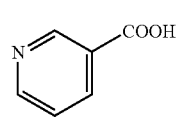

k
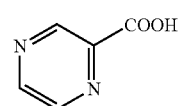

l
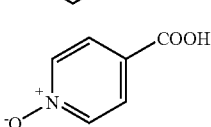

m
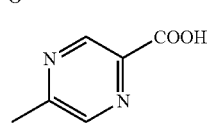

n
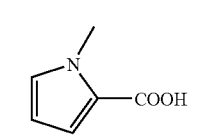

o

Carboxylic Acids Het-COOH XX:

Example 40

Preparation of 4'-(1,1-dimethyl-6-morpholin-4-yl-6-oxo-hexyl)-2'-hydroxy-biphenyl-3-ylmethyl]-methane sulfonamide (71)

Compound 71 was obtained from Bromo-phenyl XII, via reaction of resin bound intermediate XIII with boronate XIVe and methanesulfonyl chloride using General Procedures D, E, F, J and H as described in Example 14 for the preparation of Compound 2. Yield 17 mg (13%). M+1=489.

Example 41

Preparation of 4'-(1,1-dimethyl-6-morpholin-4-yl-6-oxo-hexyl)-2'-hydroxy-biphenyl-2-ylmethyl]-methane sulfonamide (72)

Example 72 was obtained from Bromo-phenyl XII, via reaction of resin bound intermediate XIII with boronate XIVd and methanesulfonyl chloride using General Procedures D, E, F, J, and H as described in Example 14 for the preparation of Compound 2. Yield 2.2 mg (2%). M+1=489.

Example 42

Preparation of (E)-4-(3-(benzyloxy)phenyl)-4-methylpent-2-ene nitrile (XXXIV)

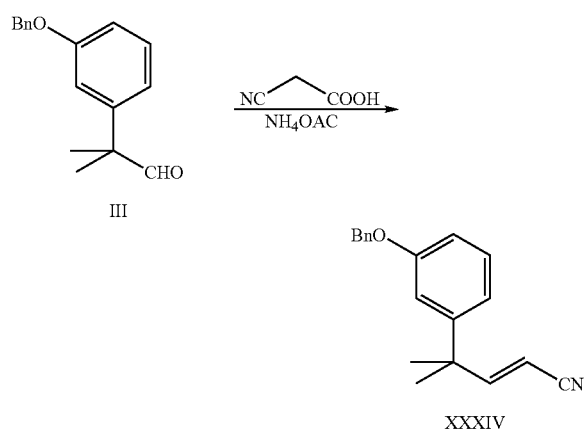

To a solution of benzyloxy aldehyde III (320 g, 1.26 mol) in toluene (1.2 L) was added pyridine (600 mL), ammonium acetate (15 g, 0.19 mol) and cyanoacetic acid (200 g, 2.35 mol) and the mixture was refluxed for 72 hours. The reaction was diluted with ethyl acetate (3.5 L), washed with water (2 L) and washed with 1N HCl (until pH of the water layer becomes acidic), washed with brine (1 L) and the organic layer was dried and concentrated under reduced pressure to yield 317 g (91 %) cyanide XXXIV. M+1=278

Example 43

Preparation of (E)-4-(3-(benzyloxy)phenyl)-4-methylpent-2-en-1-amine (XXXV)

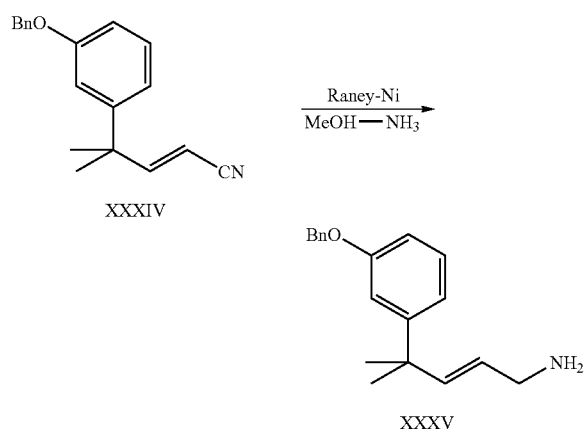

Nitrile derivative XXXIV (120 g, 0.43 mol), Raney Ni (30 mL) and ammonia in methanol (750 mL) were placed in a hydrogenator, 15 psi pressure of $H_2$ gas was applied at 60° C. for 12 h. Reaction mass was filtered and the filtrate was concentrated under reduced pressure to give 110 g crude amine XXXV (92%). M+1=282

Example 44

Preparation of N-(4-(3-(benzyloxy)phenyl)-4-methylpentyl)-2,2,2-tri-fluoro acetamide (XXXVIa)

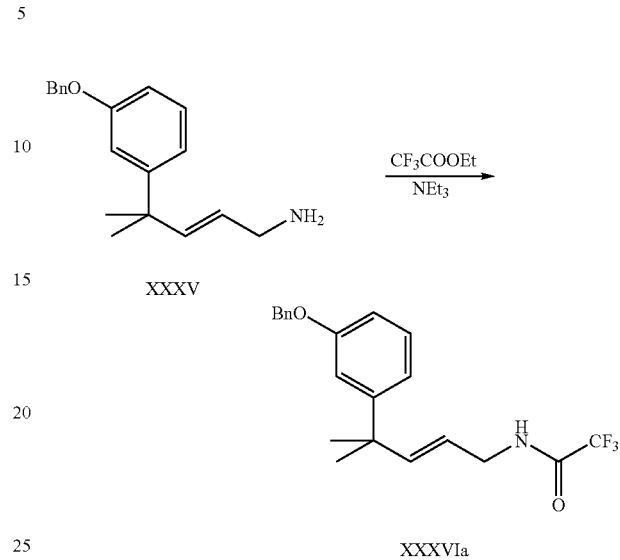

To a stirred solution of amine XXXV (196 g, 0.69 mol) in acetonitrile (1.5 L) at 0° C., was added triethylamine, followed by drop wise addition of $CF_3COOEt$ (117 g) during 60 min time. Reaction was stirred for 1 hour at room temperature. Acetonitrile was distilled off. Water was added to the crude residue and extracted with ethyl acetate(3×500 mL). The combined organic layers were washed with brine (500 mL), dried and concentrated to give 250 g of crude amide XXXVIa. M+1=378

Example 45

Preparation of 2,2,2-trifluoro-N-(4-(3-hydroxyphenyl)-4-methyl-pentyl)-acetamide (XXXVIb)

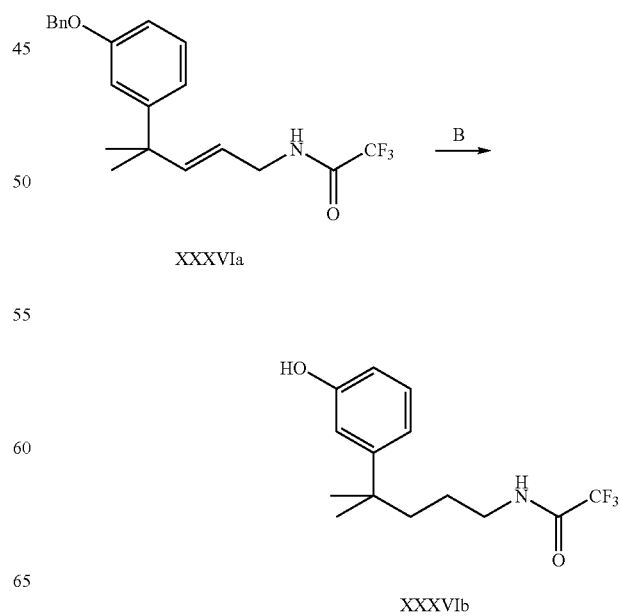

Compound XXXVIb was obtained from XXXVIa using General Procedure B. Yield 94%. M+1=290

Example 46

Preparation of 2,2,2-trifluoro-N-(4-(3-hydroxyphenyl)-4-methyl-pentyl)-acetamide (XXXVII)

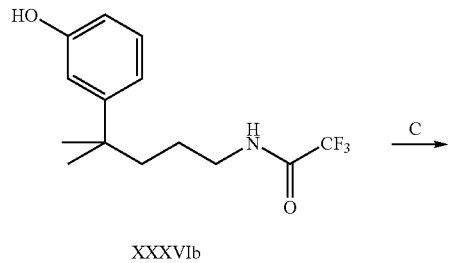

XXXVIb

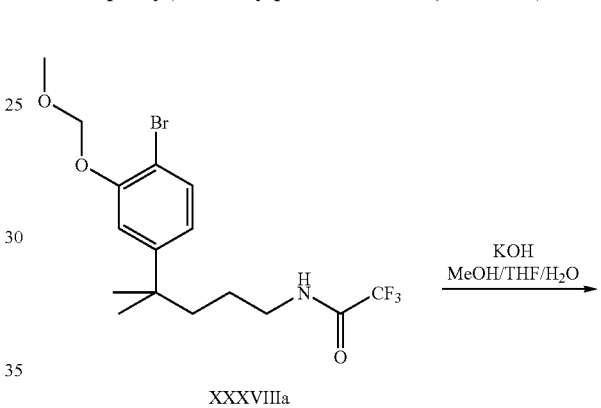

XXXVII

Compound XXXVII was obtained from XXXVII using General Procedure C. Yield 63%. M+1=368

Example 47

Preparation of N-(4-(4-bromo-3-(methoxymethoxy)-phenyl)-4-methylpentyl)-2,2,2-trifluoroacetamide (XXXVIIIa)

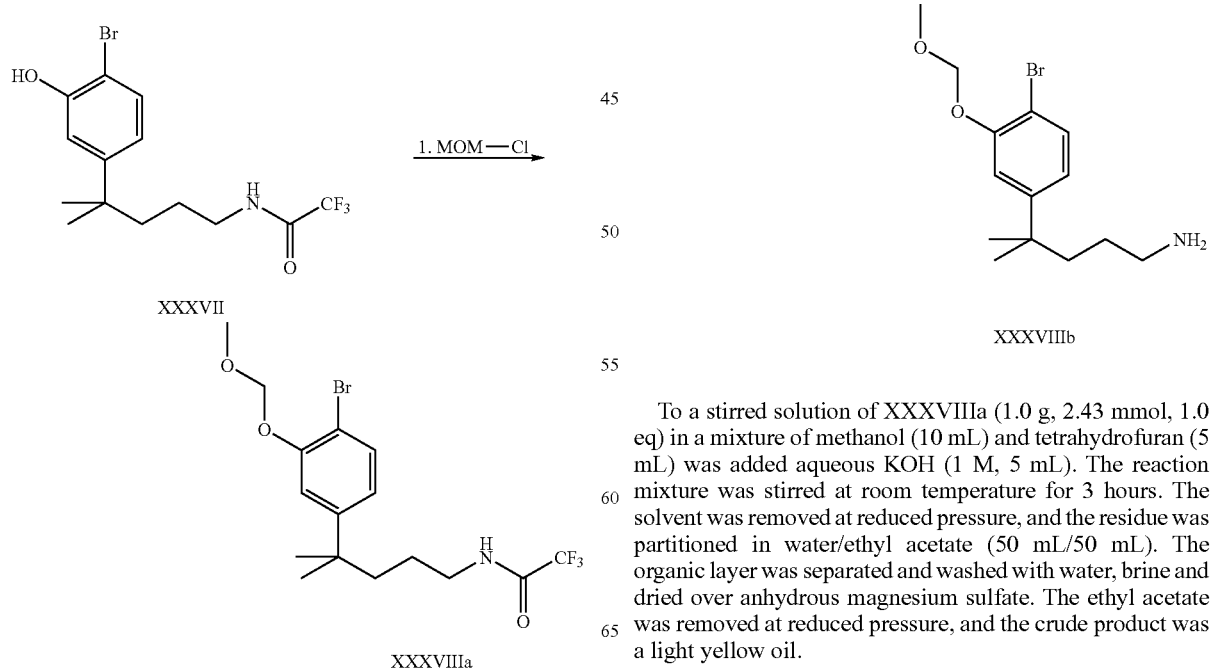

To a solution of XXXVII (10.0 g, 27.3 mmol, 1.0 eq) and diisopylethylamine (14.2 mL, 81.8 mmol, 3.0 eq) in dichloromethane (150 mL) at 0° C. was added chloromethylmethyl ether (4.2 mL, 54.5 mmol, 2.0 eq) slowly under a nitrogen atmosphere. The mixture was slowly warmed up to room temperature and stirred for 2.5 hours. LC/MS indicated a quantitative conversion. Water (150 mL) was added and the organic layer was separated and washed with 1N HCl, brine and dried over anhydrous magnesium sulfate. Dichloromethane was removed at reduced pressure, and the crude product XXXVIIIa was a white solid.

Yield: 99.8%, 98% pure. M+H$_2$O=429 $^1$H NMR (400 MHz, CDCl$_3$) δ 7.45 (d, J=8.5, 1H), 7.07 (d, J=2.2, 1H), 6.84 (dd, J=8.6, 2.2, 1H), 6.19 (bs, 1H), 5.23 (s, 2H), 3.53 (s, 3H), 3.26 (q, J=6.9, 2H), 1.61 (m, 2H), 1.29 (s, 6H)

Example 48

Preparation of 4-(4-bromo-3-(methoxymethoxy)phenyl)-4-methylpentan-1-amine (XXXVIIb)

To a stirred solution of XXXVIIIa (1.0 g, 2.43 mmol, 1.0 eq) in a mixture of methanol (10 mL) and tetrahydrofuran (5 mL) was added aqueous KOH (1 M, 5 mL). The reaction mixture was stirred at room temperature for 3 hours. The solvent was removed at reduced pressure, and the residue was partitioned in water/ethyl acetate (50 mL/50 mL). The organic layer was separated and washed with water, brine and dried over anhydrous magnesium sulfate. The ethyl acetate was removed at reduced pressure, and the crude product was a light yellow oil.

Yield: 99%, 98% pure. M+1=316

Example 49

Preparation of tert-butyl 1-(4-(4-bromo-3-(methoxymethoxy)phenyl)-4-methylpentyl-amino)-2-methyl-1-oxopropan-2-ylcarbamate (XXXIXa)

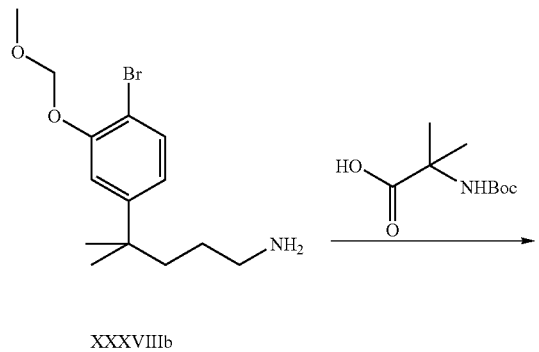

To a mixture of XXXVIIIb (0.76 g, 2.43 mmol, 1.0 eq), TBTU (bromo-tris-pyrrolidino-phosphonium hexafluorophosphate, 1.17 g, 3.65 mmol, 1.5 eq) and 2-(tert-butoxycarbonylamino)-2-methylpropanoic acid (0.74 g, 3.65 mmol, 1.5 eq) in acetonitrile (20 mL) was added diisopylethylamine (1.3 mL, 7.29 mmol, 3.0 eq) at 0° C. The reaction mixture was stirred at room temperature for 16 hours. Ethyl acetate (50 mL) and water (50 mL) were added, and the organic layer was separated and washed with 1 N HCl, brine and dried over anhydrous magnesium sulfate. The ethyl acetate was removed at reduced pressure, and the product was purified by column chromatography (ethyl acetate/Hexane, 30/70-50/50). Product XXXIXa was obtained as slightly colored oil. Yield: 86.8%, 98% pure. M+1=501

$^1$H NMR (400 MHz, CDCl$_3$) δ 7.43 (d, J=8.7, 1H), 7.09 (d, J=2.0, 1H), 6.85 (dd, J=8.4, 2.1, 1H), 6.38 (bs, 1H), 5.24 (s, 2H), 4.86 (bs, 1H), 3.54 (s, 3H), 3.14 (q, J=6.6, 2H), 1.61 (m, 2H), 1.45 (s, 6H), 1.41 (s, 9H), 1.27 (s, 6H), 1.21-1.29 (m, 2H)

Example 50

Preparation of tert-butyl 1-(4-(3'-((3-ethylureido)methyl)-2-(methoxymethoxy)-biphenyl-4-yl)-4-methylpentylamino)-2-methyl-1-oxopropan-2-yl carbamate (XLa)

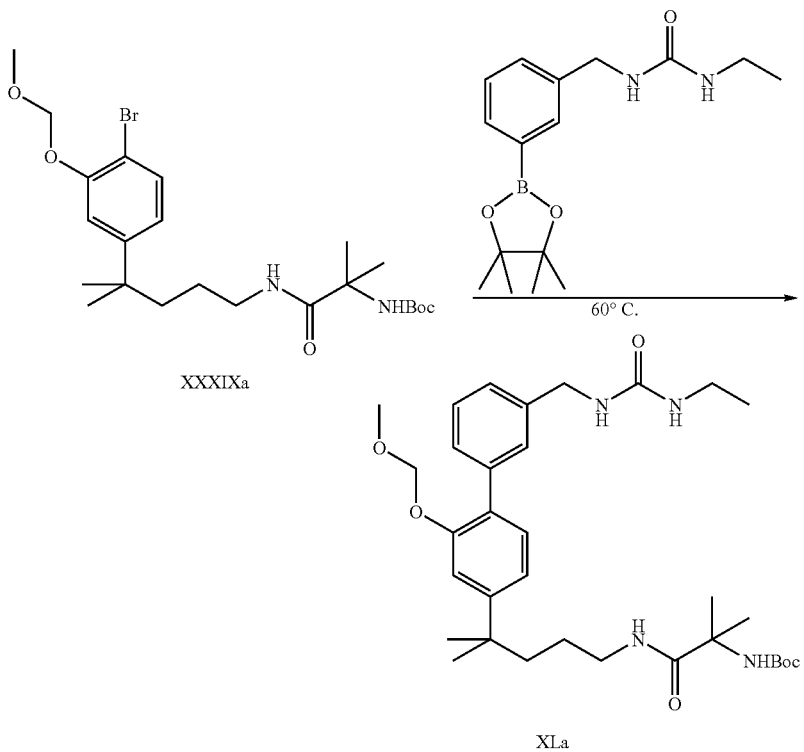

A mixture of XXXIXa (1.01 g, 2.02 mmol, 1.0 eq), 1-ethyl-3-(3-(4,4,5,5-tetramethyl-1,3,2-dioxaborolan-2-yl)benzyl) urea XIVf (0.93 g, 3.03 mmol, 1.5 eq), palladium acetate (0.068 g, 0.3 mmol, 0.15 eq), S-PHOS (0.123 g, 0.3 mmol, 0.15 eq) and potassium phosphate (1.29 g, 6.06 mmol, 3.0 eq) in tetrahydrofuran/H$_2$O (100/1 mL) was degassed with N$_2$ for 2 min and then the reaction mixture was heated at 60° C. under a nitrogen atmosphere for 16 hours. Tetrahydrofuran was removed at reduced pressure, and the residue was partitioned in ethyl acetate/H$_2$O (100 mL each). The organic layer was separated, and was washed with water, brine and dried over anhydrous magnesium sulfate. The crude product was purified with silica gel chromatography (5% methanol in dichloromethane). The 97% pure product XLa was obtained as colorless oil. Yield: 33%, 97% pure. M+1=599

$^1$H NMR (400 MHz, CDCl$_3$) δ 7.45 (s, 1H), 7.44 (d, J=8.1, 1H), 7.36 (t, J=7.6, 1H), 7.26 (b, 1H), 7.23 (d, J=8.2, 1H), 7.14 (d, J=2.0, 1H), 7.04 (dd, J=8.1, 2.0, 1H), 6.40 (bs, 1H), 5.08 (s, 2H), 4.96 (bs, 1H), 4.69 (bt, J=6.6, 1H), 4.42 (d, J=6.2, 2H), 4.37 (bt, J=6.6, 1H), 3.38 (s, 3H), 3.14-3.25 (m, 4H), 1.65 (m, 2H), 1.45 (s, 6H), 1.41 (s, 9H), 1.33 (m, 2H), 1.32 (s, 6H), 1.12 (t, J=7.4, 3H)

Example 51

Preparation of 2-amino-N-(4-(5'-((3-ethylureido) methyl)-2-hydroxybiphenyl-4-yl)-4-methylpentyl)-2-methylpropanamide hydrochloride (73)

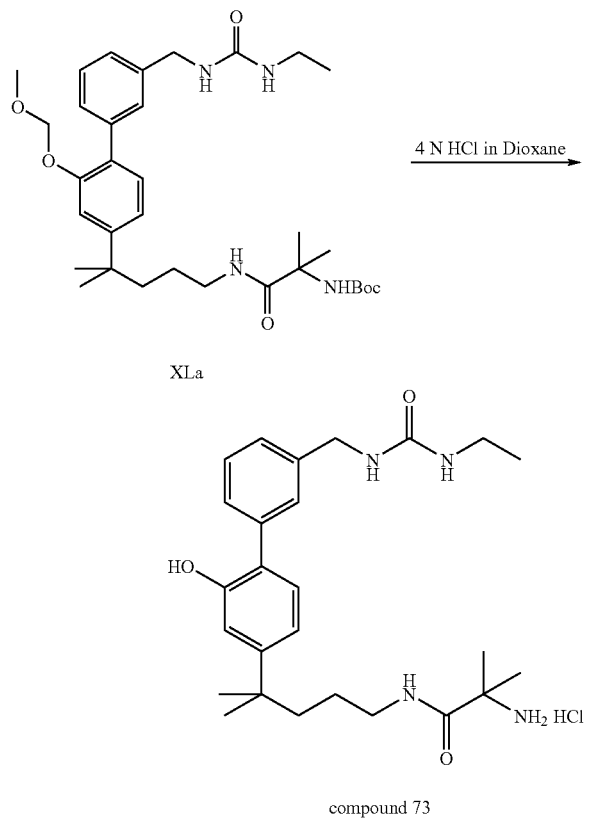

To a solution of XLa (0.20 g, 0.40 mmol, 1.0 eq) in dichloromethane (3 mL) was slowly added HCl/dioxane (4M, 10 mL). The reaction mixture was stirred at room temperature for 16 hours. The solvent was removed under reduced pressure, and the residue was triturated/washed with tetrahydrofuran and ether. Yield: 99.2%, 97% pure. M+1=455

$^1$H NMR (400 MHz, DMSO-d$_6$) δ 9.36 (bs, 1H), 8.25 (t, J=5.6, 1H), 8.17 (s, 2H), 7.39 (s, 1H), 7.38 (d, J=6.9, 1H), 7.31 (t, J=7.8, 1H), 7.15 (d, J=8.6, 1H), 7.14 (d, J=7.6, 1H), 6.93, (d, J=1.5, 1H), 6.83 (dd, J=8.0, 1.5, 1H), 6.38 (bs, 1H), 4.22 (s, 2H), 2.99-3.09 (m, 4H), 1.56 (m, 2H), 1.42 (s, 6H), 1.24 (s, 6H), 1.21 (m, 2H), 0.99 (t, J=7.1, 3H)

Example 52

Preparation of N-(4-(4-bromo-3-(methoxymethoxy) phenyl)-4-methylpentyl)-nicotinamide (XXXIXb)

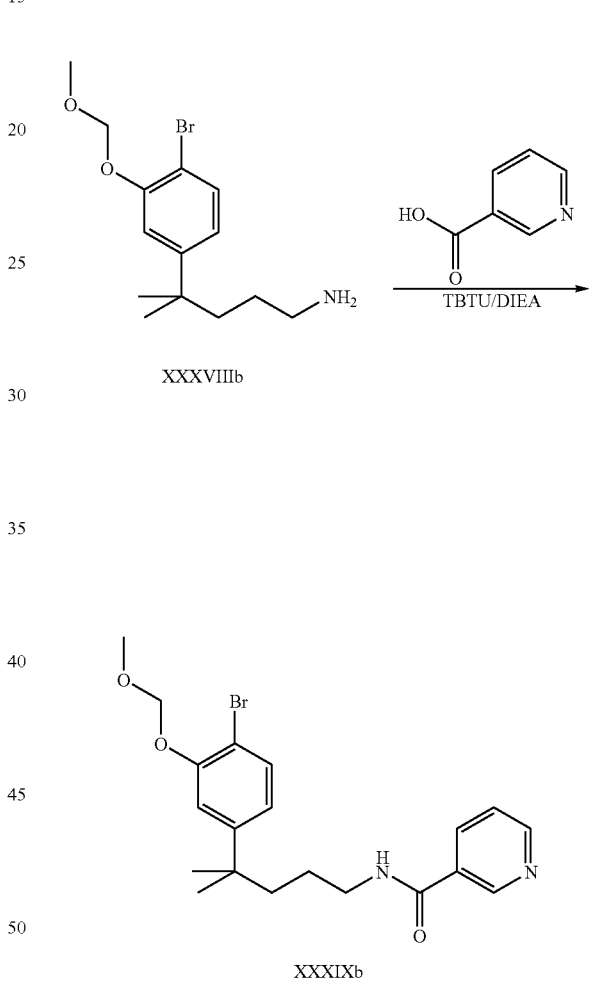

To a mixture of XXXVIIIb (1.38 g, 4.38 mmol, 1.0 eq), TBTU (bromo-tris-pyrrolidino-phosphonium hexafluorophosphate, 2.11 g, 6.57 mmol, 1.5 eq) and nicotinic acid (0.81 g, 6.57 mmol, 1.5 eq) in acetonitrile (20 mL) was added diisopylethylamine (2.34 mL, 13.14 mmol, 3.0 eq) at 0° C. The reaction mixture was stirred at room temperature for 4 hours. Ethyl acetate (50 mL) and water (50 mL) were added, and the organic layer was separated and washed with water, brine and dried over anhydrous magnesium sulfate. Ethyl acetate was removed under reduced pressure, and the product was purified by column chromatography (methanol/dichloromethane, 0-5%). Product XXXIXb was obtained as slightly colored oil. Yield: 63%, 95% pure. M+1=421

Example 53

Preparation of N-(4-(5'-((3-ethylureido)methyl)-2-(methoxymethoxy)-biphenyl-4-yl)-4-methylpentyl) nicotinamide (XLb)

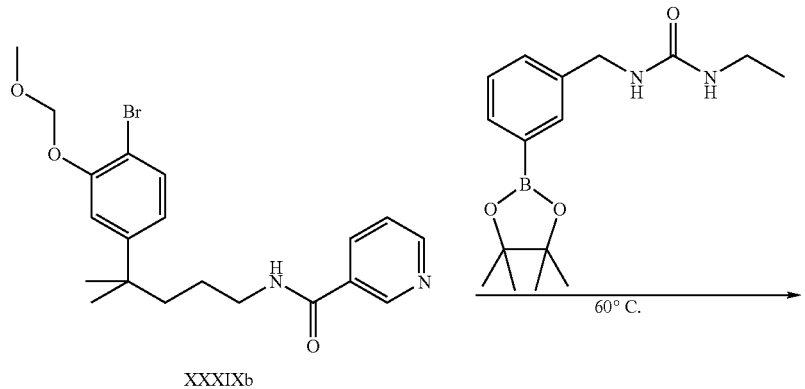

A mixture of XXXIXb (0.75 g, 1.786 mmol, 1.0 eq), 1-ethyl-3-(3-(4,4,5,5-tetramethyl-1,3,2-dioxaborolan-2-yl)benzyl)urea XIVf (0.814 g, 2.68 mmol, 1.5 eq), palladium acetate (0.080 g, 0.36 mmol, 0.2 eq), S-PHOS (0.146 g, 0.36 mmol, 0.2 eq) and potassium phosphate (1.14 g, 5.36 mmol, 3.0 eq) in tetrahydrofuran/H$_2$O (100/0.2 mL) was degassed with N$_2$ for 2 min and then was heated at 60° C. under a nitrogen atmosphere for 6 hours. Tetrahydrofuran was removed at reduced pressure, and the residue was partitioned in ethyl acetate/H$_2$O (100 mL each). The organic layer was separated, and was washed with water, brine and dried over anhydrous magnesium sulfate. The crude product was purified with silica gel chromatography (5% methanol in dichloromethane). The pure product was obtained as colorless oil. Yield: 19%, 100% pure. M+1=519

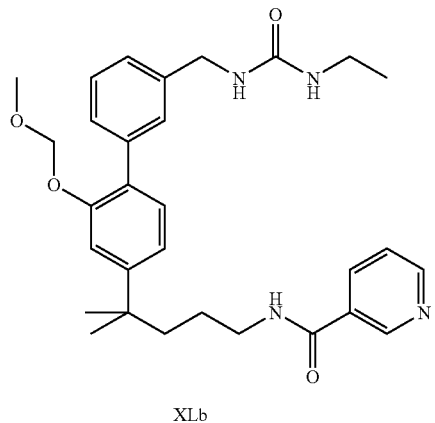

XLb $^1$H NMR (400 MHz, CDCl$_3$) δ 8.92 (d, J=1.5, 1H), 8.67 (t, J=2.3, 1H), 8.08 (m, 1H), 7.41 (m, 2H), 7.33 (m, 2H), 7.20 (m, 2H), 7.14 (d, J=1.9, 1H), 7.02 (dd, J=8.1, 1.9, 1H), 6.48 (bs, 1H), 5.04 (s, 2H), 4.98 (bs, 1H), 4.58 (b, 1H), 4.37 (d, J=5.0, 2H), 3.38 (q, J=6.1, 2H), 3.34 (s, 3H), 3.16 (m, 2H), 1.68-1.72 (m, 2H), 1.39-1.48 (m, 2H), 1.34 (s, 6H), 1.07 (t, J=7.3, 3H)

Example 54

Preparation of N-(4-(5'-((3-ethylureido)methyl)-2-hydroxybiphenyl-4-yl)-4-methylpentyl)nicotinamide hydrochloride (74)

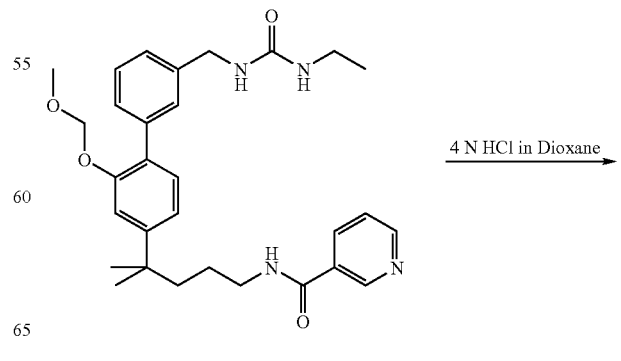

XLb

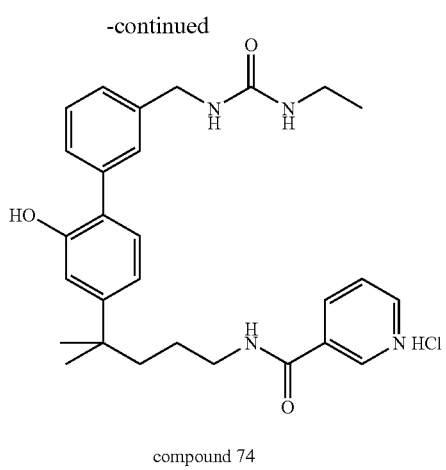

compound 74

To a solution of XLb (0.15 g, 0.29 mmol, 1.0 eq) in dichloromethane (3 mL) was slowly added HCl/dioxane (4M, 10 mL). The reaction mixture was stirred at room temperature for 16 hours. The solvent was removed under reduced pressure, and the residue was triturated/washed with dichloromethane, tetrahydrofuran, and ether, and dried in the vacuum oven (50° C., 48 hours).

Yield: 95%, 99% pure. M+1=475. $^1$H NMR (400 MHz, DMSO-d$_6$) δ 9.35 (b, 1H), 9.10 (bs, 1H), 8.83 (bs, 1H), 8.45 (bs, 1H), 7.77 (bs, 1H), 7.38 (s, 1H), 7.37 (d, J=5.6, 1H), 7.30 (t, J=9.6, 1H), 7.13 (d, J=8.1, 2H), 6.93 (s, 1H), 6.85 (d, J=9.6, 1H), 4.22 (s, 2H), 3.22 (m, 2H), 3.01 (q, J=7.1, 2H), 1.60-1.66 (m, 2H), 1.30-1.38 (m, 2H), 1.26 (s, 6H), 0.98 (t, J=7.2, 3H)

Preparation of 1-ethyl-3-((2'-methoxy-4'-(2-methyl-7-morpholino-7-oxoheptan-2-yl)biphenyl-3-yl)methyl)urea (75)

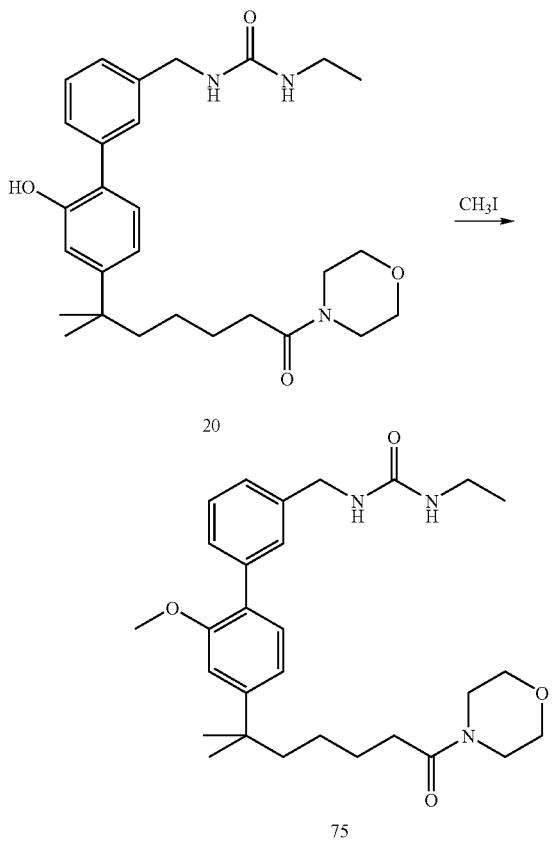

A mixture of 20 (0.1 g, 0.208 mmol, 1.0 eq), iodomethane (0.05 mL, 0.832 mmol, 4.0 eq), and K$_2$CO$_3$ (0.115 g, 0.832 mmol, 4.0 eq) in acetone (3 mL) was heated to 60° C. overnight. LC/MS showed SM/product ~1/1. More K$_2$CO$_3$ (0.2 g, 1.45 mmol, 7 eq) and iodomethane (0.2 mL, 3.21 mmol, 15.4 eq) were added, and the mixture was heated again to 60° C. overnight. Acetone was removed under reduced pressure, and the residue was partitioned in water/ethyl acetate. The aqueous layer was extracted with ethyl acetate (2×20 mL), and the combined organic layer was washed by water (20 mL), brine (20 mL) and dried over anhydrous K$_2$CO$_3$. The solvent was removed under reduced pressure, and the residue was purified by column chromatography (silica gel, 60-100% ethyl acetate in hexane). Yield: 23%, 98% pure. M+1=496

$^1$H NMR (400 MHz, CDCl$_3$) δ 7.46 (s, 1H), 7.44 (d, J=7.6, 1H), 7.36 (t, J=7.6, 1H), 7.24 (d, J=8.1, 1 H), 7.23 (d, J=7.6, 1H), 6.97 (dd, J=8.1, 1.5, 1H), 6.92 (d, J=1.5, 1H), 4.59 (t, J=5.5, 1H), 4.42 (d, J=5.5, 2H), 4.25 (t, J=5.5, 1H), 3.80 (s, 3H), 3.61 (m, 4H), 3.57 (m, 2H), 3.40 (m, 2H), 3.22 (m, 2 H), 2.25 (t, J=7.6, 2H), 1.66 (m, 2H), 1.58 (m, 2H), 1.34 (s, 6H), 1.15 (m, 2H), 1.13 (t, J=7.1, 3H).

Preparation of N-(4-(5'-((3-ethylureido)methyl)-2-methoxybiphenyl-4-yl)-4-methyl-pentyl)pivalamide (76)

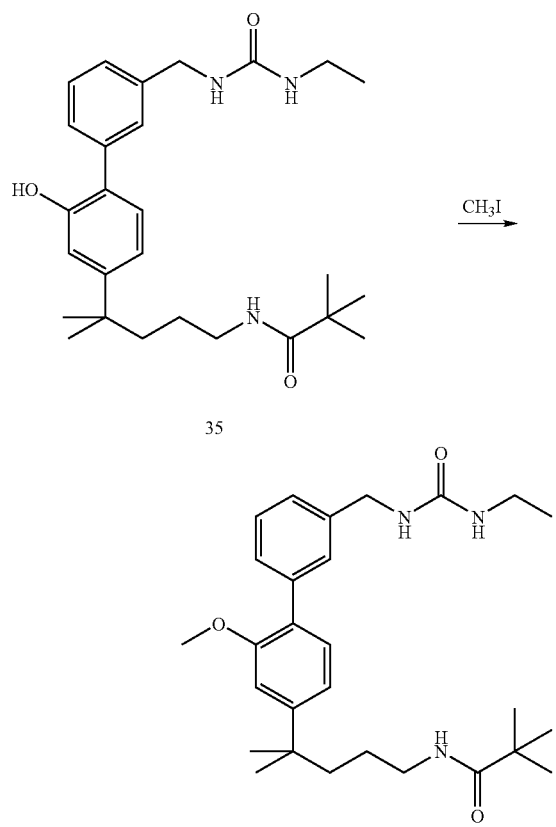

A mixture of 35 (0.23 g, 0.508 mmol, 1.0 eq), iodomethane (0.13 mL, 2.1 mmol, 4.1 eq), and K$_2$CO$_3$ (0.56 g, 4.06 mmol, 8.0 eq) in acetone (5 mL) was heated to 70° C. for 24 hours. LC/MS showed complete conversion. Acetone was removed under reduced pressure, and the residue was partitioned in water/ethyl acetate. The aqueous layer was extracted with ethyl acetate (2×20 mL), and the combined organic layer was washed by water (20 mL), brine (20 mL) and dried over anhydrous K$_2$CO$_3$. The solvent was removed under reduced pressure, and the residue was purified by column chromatography (neutral aluminum gel, 0-3% methanol in dichloromethane). Yield: 63%, 99% pure. M+1=468

$^1$H NMR (400 MHz, CDCl$_3$) δ 7.43 (s, 1H), 7.42 (d, J=7.6, 1H), 7.33 (t, J=7.6, 1H), 7.21 (d, J=8.0, 1H), 7.21 (d, J=7.6, 1H), 6.95 (dd, J=8.0, 1.5, 1H), 6.90 (d, J=1.5, 1H), 5.60 (bt, 1H), 5.02 (bt, 1H), 4.69 (bt, 1H), 4.37 (d, J=4.0, 2H), 3.78 (s, 3H), 3.14 (m, 4H), 1.63 (m, 2H), 1.33 (s, 6H), 1.29 (m, 2H), 1.15 (s, 9H), 1.07 (t, J=7.1, 3H)

Preparation 1-ethyl-3-((2'-hydroxy-4'-(2-methyl-7-morpholinoheptan-2-yl)biphenyl-3-yl)methyl)urea (77)

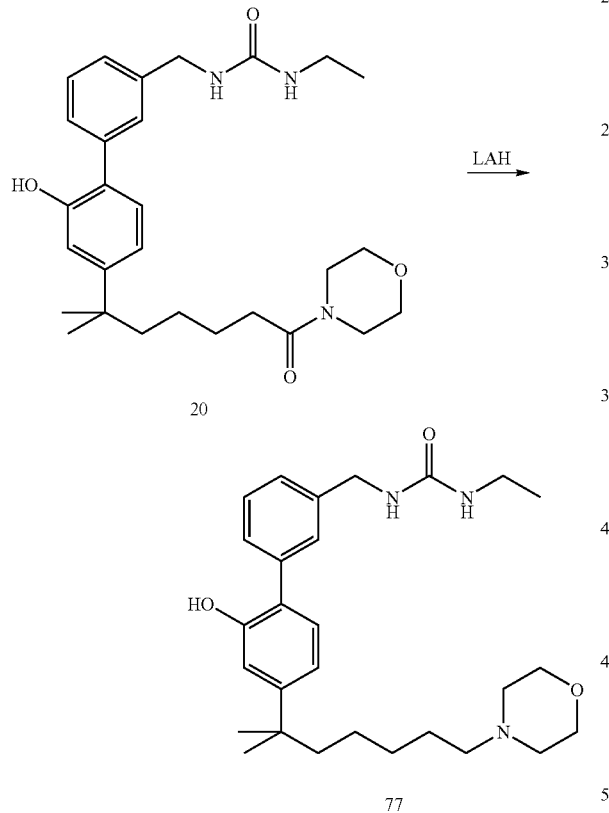

To a solution of 20 (0.2 g, 0.416 mmol, 1.0 eq) in tetrahydrofuran (10 mL) under nitrogen atmosphere at 0° C. was added lithium aluminum hydride (1.0 M in THF, 1.6 mL, 1.60 mmol, 4.0 eq). The mixture was slowly warmed up to room temperature over 2.5 hours, and LC/MS showed the reaction was complete. The reaction was quenched with ice chips, and then water/ethyl acetate was added. The aqueous layer was extracted with ethyl acetate (2×20 mL), and the combined organic layer was washed with water (20 mL), brine (20 mL) and dried over anhydrous MgSO$_4$. The solvent was removed under reduced pressure, and the residue was purified by column chromatography (neutral aluminum gel, 2% methanol in dichloromethane).

Yield: 98%, 99% pure. M+1=468 $^1$H NMR (400 MHz, DMSO-d$_6$) δ 9.30 (s, 1H), δ 7.39 (s, 1H), 7.38 (d, J=5.0, 1H), 7.30 (t, J=7.5, 1H), 7.14 (d, J=8.0, 1H), 7.13 (d, J=5.0, 1H), 6.90 (d, J=1.8, 1H), 6.83 (dd, J=7.6, 1.8, 1H), 6.29 (t, J=5.6, 1H), 5.86 (t, J=5.6, 1H), 4.22 (d, J=6.1, 2H), 3.52 (m, 4H), 3.02 (m, 2H), 2.28 (bs, 4H), 2.17 (m, 2H), 1.55 (m, 2H), 1.34 (m, 2H), 1.23 (s, 6H), 1.21 (m, 2H), 1.09 (m, 2H), 0.99 (t, J=7.0, 3H)

Elemental Analysis:
C$_{28}$H$_{41}$N$_3$O$_3$, 0.5H$_2$O
Theory: % C 70.55; % H 8.88; % N 8.82
Found: % C 70.25; % H 8.66; % N 8.62

Preparation of 1-ethyl-3-((2'-hydroxy-4'-(2-methyl-5-(neopentylamino)pentan-2-yl)biphenyl-3-yl)methyl)urea (78)

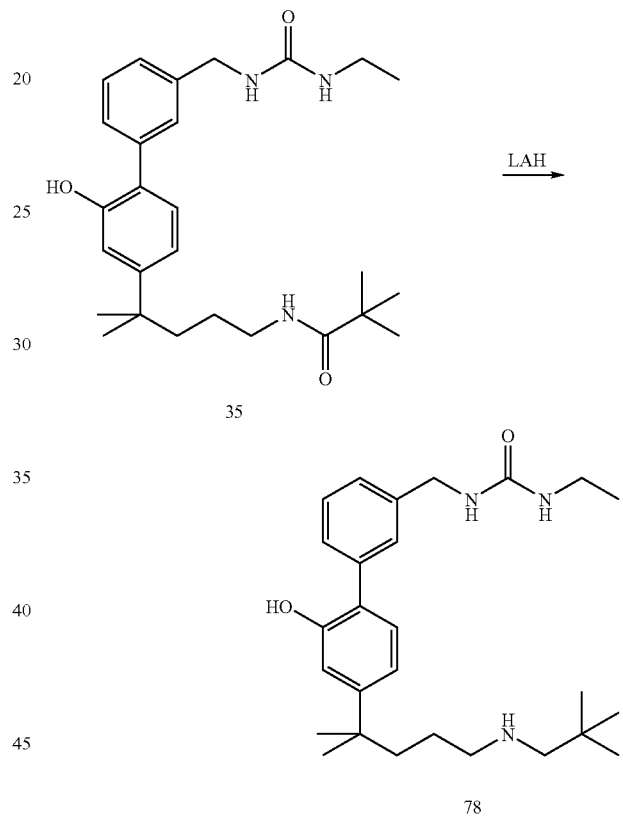

To a solution of 35 (0.1 g, 0.22 mmol, 1.0 eq) in tetrahydrofuran (10 mL) under nitrogen at 0° C. was added lithium aluminum hydride (1.0 M in THF, 1.76 mL, 1.76 mmol, 4.0 eq). The mixture was slowly warmed up to room temperature over 2.5 hours. The reaction was quenched with ice chips, and then water and ethyl acetate were added. The aqueous layer was extracted with ethyl acetate (2×20 mL), and the combined organic layer was washed with water (20 mL), brine (20 mL) and dried over anhydrous MgSO$_4$ The solvent was removed under reduced pressure, and the residue was purified by column chromatography (silica gel, 2-10% methanol in dichloromethane).

Yield: 16%, 96% pure. M+1=440 $^1$H NMR (400 MHz, CDCl$_3$) δ 7.36 (m, 1H), 7.32 (m, 2H), 7.22 (d, J=6.5, 1H), 7.09 (d, J=7.5, 1H), 6.85-6.88 (m, 2H), 4.98 (b, 1H), 4.63 (b, 1H), 4.31 (d, J=5.1, 2H), 3.18 (m, 2H), 2.54 (t, J=7.6, 2H), 2.32 (s, 2H), 1.58 (m, 2H), 1.35 (m, 2H), 1.29 (s, 6H), 1.10 (t, J=7.2, 3H), 0.86 (s, 9H)

Biological Assays:

In Vitro Methods

Preparation of Membranes for hCB1 and hCB2 Receptor Binding and Receptor-Mediated Stimulation of [$^{35}$S]GTPγS Binding:

Chinese hamster ovary cells (CHO-K1), stably transfected with either hCB1 or hCB2, were washed two times with cold PBS, scraped from 500 cm$^2$ tissue culture plates, and pelleted by centrifugation at 1000×g for 10 min. The supernatant was discarded and the pellet was re-suspended in Tris assay buffer (50 mM Tris HCl, pH 7.8, containing 1.0 mM EGTA, 5.0 mM MgCl$_2$, 10 µg/mL leupeptin, 10 µg/mL pepstatin A, 200 µg/mL bacitracin, and 0.5 µg/mL aprotinin), homogenized with a Polytron homogenizer (Brinkmann) at a setting of 1 for 20 sec and centrifuged at 38,000×g for 20 min at 4° C. The pellet was re-suspended in Tris assay buffer and aliquots of 1 mg protein/mL were stored at −80° C. for further use.

Preparation of Rat Cerebellar Membranes for Cannabinoid Receptor-Mediated Stimulation of [$^{35}$S]GTPγS Binding:

Rat cerebella were excised and placed into homogenization buffer (50 mM Tris HCl, pH 7.4, containing 3 mM MgCl$_2$ and 1 mM EGTA) and homogenized for 20 sec using a Polytron homogenizer at a setting of 1 and centrifuged at 4° C. for 10 min at 48,000×g. The supernatant was removed and the pellet was re-suspended in homogenization buffer and centrifuged at 4° C. for 10 min at 48,000×g. The supernatant was removed and the pellets were re-suspended in 50 mM Tris HCl, pH 7.4, containing 3 mM MgCl$_2$ and 0.2 mM EGTA and stored as aliquots of 1 mg protein/mL at −80° C. for further use.

Inhibition of CB Receptor Binding by Test Compounds:

Binding assays were performed by incubating 0.2-0.6 nM (34,000-100,000 dpm) of [$^3$H]CP55940 with membranes prepared from cells expressing cloned human CB1 or CB2 receptors in buffer A (50 mM Tris HCl, pH 7.0, 5.0 mM MgCl$_2$, 1.0 mM EGTA and 1.0 mg/mL fatty acid free bovine serum albumin). After incubation for 60 min at room temperature for the hCB2 binding assay or 120 min at 30° C. for the hCB1 assay, the assays were filtered through GF/C filters that had been pre-soaked overnight in 0.5% (w/v) PEI and 0.1% BSA in water. The filters were rinsed 6 times with one mL of cold wash buffer (50 mM Tris HCl, pH 7.0, 5.0 mM MgCl$_2$, 1.0 mM EGTA and 0.75 mg/mL fatty acid free bovine serum albumin), 30 µL of MicroScint 20 was added to each filter and the radioactivity on the filters determined by scintillation spectroscopy. Nonspecific binding was determined in the presence of 10 µM WIN55212-2.

Cannabinoid Receptor-Mediated Stimulation of [$^{35}$S]GTPγS Binding:

hCB1-mediated stimulation of [$^{35}$S]GTPγS binding was measured in a mixture containing 100-150 pM [$^{35}$S]GTPγS, 150 mM NaCl, 45 mM MgCl$_2$, 3 mM GDP, 0.4 mM DTT, 1 mM EGTA, 1 mg/mL fatty acid free BSA, 25 µg of membrane protein and agonist in a total volume of 250 µL of buffer A in 96 well Basic Flashplates (Perkin Elmer). After incubation at room temperature for 2 hours the plates were centrifuged at 800×g at 4° C. for 5 min and the radioactivity bound to the membranes was determined by scintillation spectrometry using the Topcount (Perkin Elmer).

hCB2-mediated [$^{35}$S]GTPγS binding was measured in the same way except the assay mixture contained 10 mM GDP and the incubation time was 6 hours. [$^{35}$S]GTPγS binding in rat cerebellar homogenate was determined in a mixture containing 40-60 pM [$^{35}$S]GTPγS, homogenate assay buffer (50 mM Tris-HCl, 3 mM MgCl$_2$, 0.2 mM EGTA), 100 mM NaCl, 10 mM MgCl$_2$, 100 mM GDP, 20 µg homogenate protein/well and agonist in a total volume of 250 µL in 96 well Basic Flashplates (Perkin Elmer). After incubation at 30° C. for 2 hours, the plates were centrifuged at 800×g at 4° C. for 5 min and the radioactivity bound to the membrane was determined by scintillation spectrometry using the Topcount (Perkin Elmer).

$K_i$ values in receptor binding experiments were determined by Cheng-Prusoff correction of IC$_{50}$ values derived from automated nonlinear regression analysis of sigmoidal titration curves using a three-parameter modification (slope set to 1.0) of the four-parameter equation described by DeLean et al., 1978. EC$_{50}$ values in functional assays were also derived from automated nonlinear regression analysis of sigmoidal titration curves using the three-parameter modification of the four-parameter equation.

REFERENCES

Cheng, Y.-C. and W. H. Prusoff. Relationship between the inhibition constant (K$_i$) and the concentration of inhibitor which causes 50 percent inhibition (I$_{50}$) of an enzymatic reaction (Biochem. Pharmacol. 22:3099-3108 (1973)).

DeLean, A. P., P. J. Munson, and D. Rodbard. Simultaneous analysis of families of sigmoidal curves: Application to bioassay, radioligand assay, and physiological dose-response curves (Am. J. Physiol. 235:E97-E102 (1978)).

In Vitro Results

Compounds 1-78, listed in Table 4, were tested for their affinity toward the human cloned CB1 and CB2 receptors. All ligands tested bound to the human CB1 and/or CB2 receptor with affinity ranging from 0.1-5000 nM. These ligands displayed various degrees of selectivity, CB1 vs. CB2. The functional potency of selected ligands was also evaluated in vitro. These compounds were found to exhibit agonist activity at CB1 and/or CB2 receptors. For example, Compound 12 (K$_i$(CB1)=1.6 nM, K$_i$(CB2)=0.56 nM) was found to possess potent in vitro CB1 receptor agonist potency (EC$_{50}$=15.5 nM) and potent in vitro CB2 receptor agonist potency (EC$_{50}$=15.2 nM). Compound 15 (K$_i$(CB1)=1.1 nM, K$_i$(CB2)=0.40 nM) was found to possess potent in vitro CB1 receptor agonist potency (EC$_{50}$=29.1 nM) and potent in vitro CB2 receptor agonist potency (EC$_{50}$=5.1 nM).

In Vivo Methods

Catalepsy Ring Test

The apparatus consisted of a 5.5 centimeter ring attached to a ring stand at a height of 16 centimeters. Male ICR mice (20-25 g) were placed on the ring 60 or 90 minutes after dosing (i.p.) with test compounds or vehicle. Normal behavior for a mouse would be to walk around and investigate the ring. Catalepsy was shown when the mouse remained motionless. The amount of time (in seconds, in a 5 minute test session) the mouse spent motionless was determined.

Mice that fell or jumped were allowed 5 "escapes". If 5 "escapes" happened before 2.5 minutes into the test, the data were disregarded. The immobility index (% catalepsy) was determined by the amount of time spent immobile divided by the length of the test (P. Little et al. *Pharmac. Biochem. & Behavior* 1989, 32, 661-666). Since the CB1 receptor is thought to be responsible for psychoactivity, the catalepsy ring test is an excellent in vivo screen for CB1 activity.

TABLE 1

Results of the Catalepsy Ring Test (Treatment in mg/kg i.p.)

| Compound | % catalepsy @ 30 mg/kg | % catalepsy @ 100 mg/kg |
|---|---|---|
| Vehicle | 1.11 ± 0.61 | 0.83 ± 0.78 |
| 11 | 6.65 ± 1.87 | 18.80 ± 3.33 |
| 71 | 3.38 ± 2.75 | 24.65 ± 3.36 |
| 17 | 12.21 ± 2.79 | 47.93 ± 5.98 |
| 41 | 13.07 ± 2.85 | 58.78 ± 7.95 |
| 20 | 3.07 ± 1.15 | 5.05 ± 1.81 |
| WIN @ 10 mg/kg | 51.64 ± 2.69 | — | compound 11

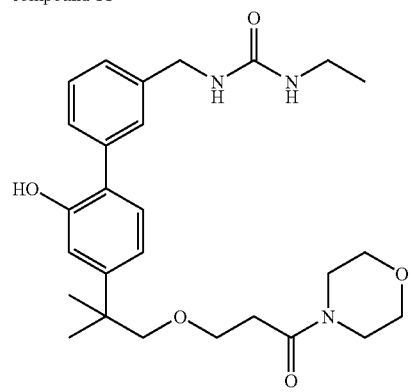

TPSA = 100
cLogP = 2.93
MW = 483
compound 71

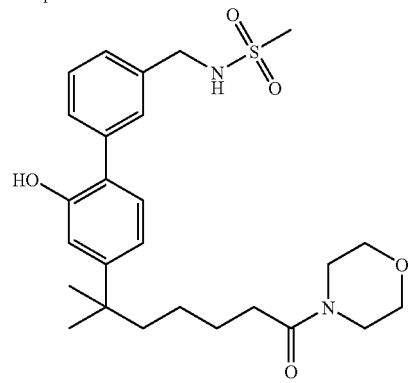

TPSA = 96
cLogP = 2.91
MW = 488
compound 17

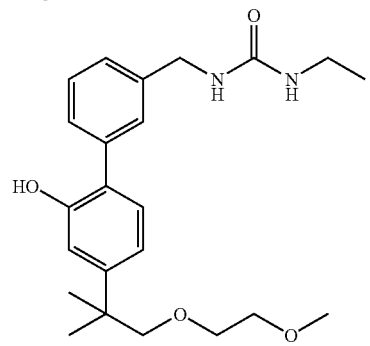

TPSA = 79
cLogP = 3.03
MW = 400
compound 41

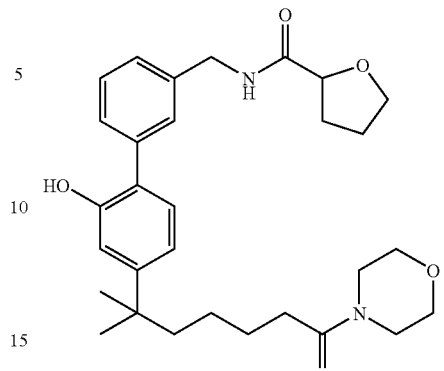

TPSA = 89
cLogP = 3.53
MW = 508
compound 20

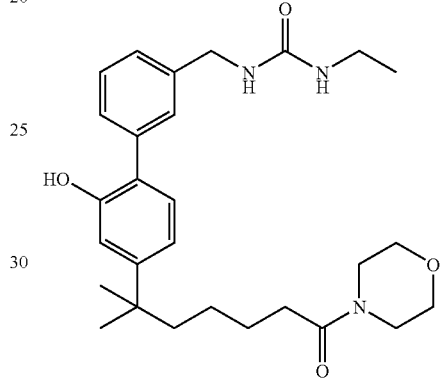

TPSA = 91
cLogP = 3.84
MW = 481

Neuropatic Pain

Preparation of Animals.

Male Sprague-Dawley rats (120-250 g, Harlan Laboratories, Columbus, Ohio) were housed in pairs and allowed free access to food and water throughout the study. Room temperature and humidity were maintained at 21° C. and 70%, respectively. Nerve injury was produced with tight ligation of the left L5 spinal nerve (Kim and Chung, 1992; LaBuda and Fuchs, 2000a, 2000b, LaBuda, Donahue and Fuchs, 2001). Briefly, animals were placed in the prone position to access the left L4-L6 spinal nerves. Under magnification, approximately one third of the L6 transverse process was removed. The L5 spinal nerve was identified and carefully dissected free from the adjacent L4 spinal nerve and then tightly ligated using 6-0 silk suture. The wound was treated with an antiseptic solution, the muscle layer was sutured, and the wound was closed with wound clips. Sham-operated surgical controls were prepared in the same manner, but the L5 spinal nerve was not exposed. All housing conditions and experimental procedures were performed in accordance with the ethical guidelines of the IASP and the Adolor Corporation Animal Care and Use Committee.

Behavioral Testing.

Seven to ten animals per group were used for all behavioral assays. After a 7-10 day post-surgical recovery, animals were tested for baseline sensitivity to tactile stimulation of both hindpaws. Allodynic animals were defined as animals having a threshold of less than 7.5 grams of pressure applied to the injured hindpaw. Tactile sensitivity was evaluated using von Frey monofilaments before and after treatment. Animals received a coded injection of physiological saline or test compound (0, 10 or-30 mg/kg, i.p.). Thirty minutes after treatment, tactile sensitivity was evaluated. Five to seven days later, animals were tested using a different compound. Each animal was tested three times with different compounds. All behavioral testing was performed between 9:00 AM and 5:00 PM in a well-illuminated room with white background noise.

Tactile Sensitivity.

Animals were placed in a Plexiglas chamber (20 cm×10.5 cm×40.5 cm) and habituated for 15 minutes. The chamber was positioned on top of a mesh screen so that von Frey monofilaments could be presented to the plantar surfaces of both hindpaws. Measurements of tactile sensitivity for each hindpaw were obtained using the up/down method (Dixon, 1980) with seven von Frey monofilaments (0.04, 0.07, 0.16, 0.4, 1, 6, and 15 grams). Each trial started with a von Frey force of 0.4 g delivered to the right hindpaw and then the left hindpaw for approximately 1-2 sec each. If there was no withdrawal response, the next higher force was delivered. If there was a response, the next lower force was delivered. This procedure was performed until no response was made at the highest force (15 grams) or until four stimuli were administered following the initial response. The 50% paw withdrawal threshold for each paw was calculated using the following formula: [Xth]log=[vFr]log+ky where [vFr] is the force of the last von Frey filament used, k=0.2249 which is the average interval (in log units) between the von Frey monofilaments, and y is a value that depends upon the pattern of withdrawal responses (Dixon, 1980). If an animal did not respond to the highest von Frey filament (15 g), then the paw was assigned a value of 18.23 g. Testing for tactile sensitivity was performed twice and the mean 50% withdrawal value assigned as the tactile sensitivity for the right and left paws for each animal.

Statistical Analysis.

Tactile sensitivity for both hindpaws before and after treatments were analyzed using one-way analysis of variance (ANOVA) followed by post-hoc comparisons (protected t-test) for group differences. An alpha level of 0.05 was used for all analyses.

REFERENCES

Dixon, W. J., Efficient analysis of experimental observations. *Annu Rev Pharmacol Toxicol* 1980, 20, 441-462.

Kim, S. H., and J. M. Chung. An experimental model for peripheral neuropathy produced by segmental spinal nerve ligation in the rat. *Pain* 1992, 50, 355-363.

LaBuda, C. J. and Fuchs, P. N., Place avoidance paradigm: A simple method for measuring the aversive quality of inflammatory and neuropathic pain in rats. *Exp Neurol* 2000a, 163, 490-494.

LaBuda, C. J. and Fuchs, P. N., Morphine and gabapentin decrease mechanical hyperalgesia and escape/avoidance behavior in a rat model of neuropathic pain. *Neurosci Letters*, 2000b, 290, 137-140.

LaBuda, C. J., Donahue, R., Fuchs, Enhanced formalin nociceptive responses following L5 nerve ligation in the rat reveals neuropathy-induced inflammatory hyperalgesia. *Pain* 2001, 94, 59-63.

TABLE 2

Results of the Neuropathic Pain Assay
n = 8 in the 10 and 30 mg/kg groups.

| | Threshold [g] |
|---|---|
| Sham | 18.17 ± 0.13 |
| Ligation | 4.41 ± 1.19 |
| Compound 20 @ 10 mg/kg | 12.16 ± 2.41 [#] |
| Compound 20 @ 30 mg/kg | 12.02 ± 2.54 [#] |

[#] = $p < 0.05$ compared to vehicle-treated, L5 SNL animals.

TABLE 3

A 2.5 mg/kg dose (i.p.) of the nonselective CB agonist WIN55,212-2 (WIN+) and the inactive enantiomer WIN55,212-3 (2.5 mg/kg, i.p., WIN−) were tested as controls. Our non-sedating, CB agonists, compound 20 and compound 35 reversed L5 SNL-induced tactile allodynia. (n = 7-8/group).

| | Threshold [g] |
|---|---|
| Sham | 11.17 ± 0.99 |
| Ligation | 3.73 ± 1.17 |
| WIN− @ 2.5 mg/kg | 6.25 ± 1.19 |
| WIN+ @ 2.5 mg/kg | 15.03 ± 1.70 |
| Compound 20 @ 3 mg/kg | 9.14 ± 3.36 |
| Compound 20 @ 10 mg/kg | 16.69 ± 1.19 [#] |
| Compound 35 @ 10 mg/kg | 10.96 ± 2.66 [#] |

[#] = $p < 0.05$ compared to vehicle-treated, L5 SNL animals.

TABLE 4

| Compound | Name | Structure | M + 1 |
|---|---|---|---|
| 1 | 1-[4'-(1,1-Dimethyl-heptyl)-2'-hydroxy-biphenyl-2-yl]-3-ethyl-urea | 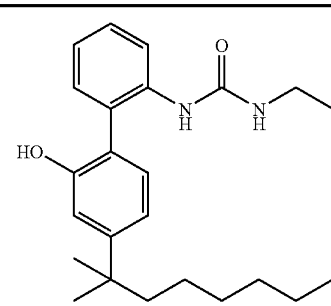 | 383 |

TABLE 4-continued

| Compound | Name | Structure | M + 1 |
|---|---|---|---|
| 2 | N-[4'-(1,1-Dimethyl-heptyl)-2'-hydroxy-biphenyl-2-yl]-methane sulfonamide | 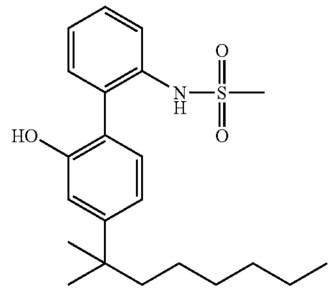 | 390 |
| 3 | N-[4'-(1,1-Dimethyl-heptyl)-2'-hydroxy-biphenyl-3-yl]-methane sulfonamide | 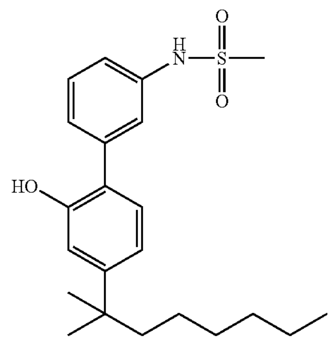 | 390 |
| 4 | 6-(2-Hydroxy-3'-methanesulfonylamino-biphenyl-4-yl)-6-methyl-heptanoic acid methyl ester | 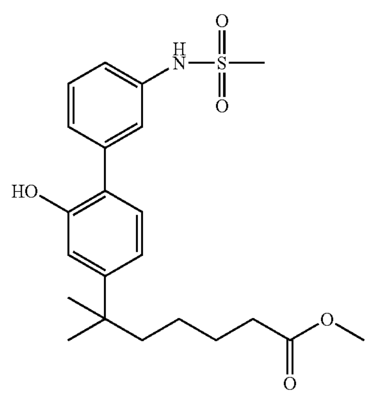 | 420 |
| 5 | 1-[4'-(1,1-Dimethyl-heptyl)-2'-hydroxy-biphenyl-3-ylmethyl]-3-ethyl-urea | 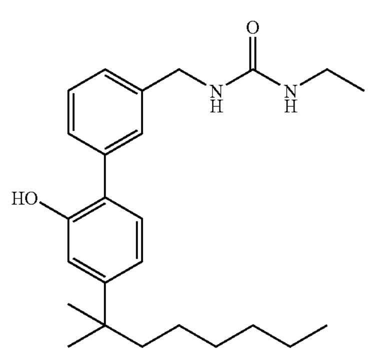 | 397 |

TABLE 4-continued

| Compound | Name | Structure | M + 1 |
|---|---|---|---|
| 6 | 1-[4'-(1,1-Dimethyl-heptyl)-2'-hydroxy-biphenyl-2-ylmethyl]-3-ethyl-urea | 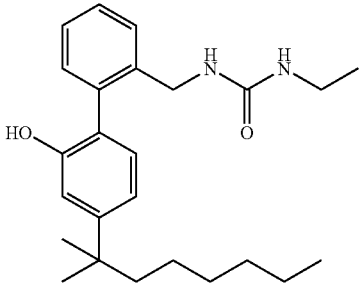 | 397 |
| 7 | 1-{2-[4'-(1,1-Dimethyl-heptyl)-2'-hydroxy-biphenyl-2-yl]-ethyl}-3-ethyl-urea | 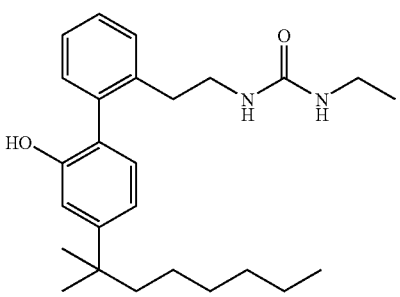 | 411 |
| 8 | N-[4'-(1,1-Dimethyl-heptyl)-2'-hydroxy-biphenyl-3-ylmethyl]methane sulfonamide | 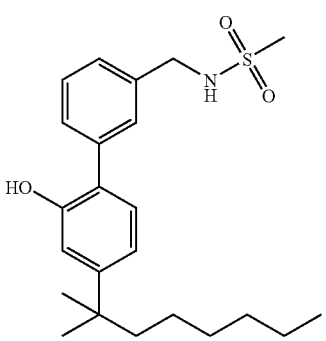 | 404 |
| 9 | N-[4'-(1,1-Dimethyl-heptyl)-2'-hydroxy-biphenyl-2-ylmethyl]-methane sulfonamide | 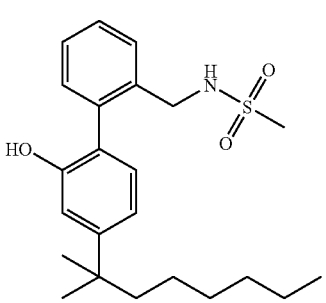 | 404 |
| 10 | N-{2-[4'-(1,1-Dimethyl-heptyl)-2'-hydroxy-biphenyl-2-yl]-ethyl}-methane sulfonamide | 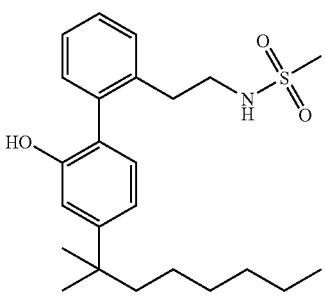 | 418 |

TABLE 4-continued

| Compound | Name | Structure | M + 1 |
|---|---|---|---|
| 11 | 1-{4'-[1,1-Dimethyl-2-(3-morpholin-4-yl-3-oxo-propoxy)-ethyl]-2'-hydroxy-biphenyl-3-yl-methyl}-3-ethyl-urea | 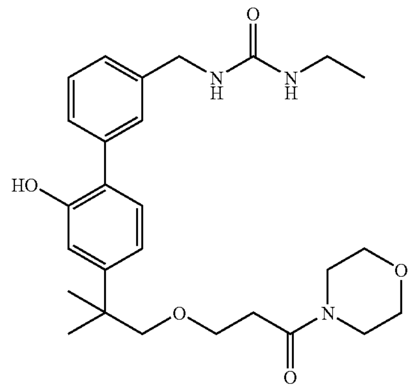 | 484 |
| 12 | 1-[4'-(2-Butoxy-1,1-dimethyl-ethyl)-2'-hydroxy-biphenyl-2-ylmethyl]-3-ethyl-urea | 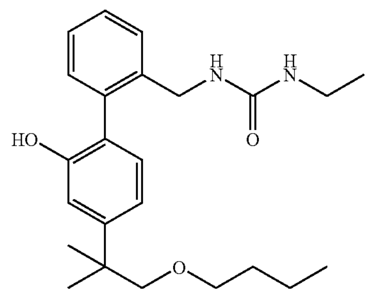 | 399 |
| 13 | 1-[4'-(2-Butoxy-1,1-dimethyl-ethyl)-2'-hydroxy-biphenyl-2-ylmethyl]-3-propyl-urea | 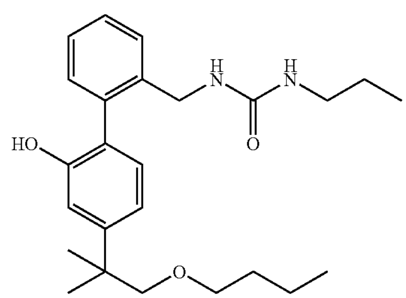 | 413 |
| 14 | 1-[4'-(2-Butoxy-1,1-dimethyl-ethyl)-2'-hydroxy-biphenyl-3-ylmethyl]-3-ethyl-urea | 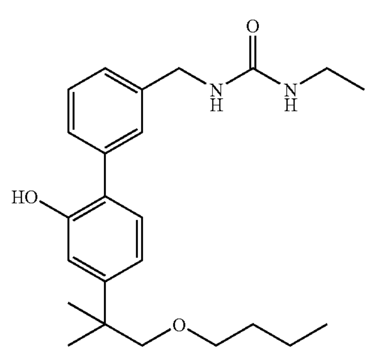 | 399 |

TABLE 4-continued

| Compound | Name | Structure | M + 1 |
|---|---|---|---|
| 15 | 1-[4'-(2-Butoxy-1,1-dimethyl-ethyl)-2'-hydroxy-biphenyl-3-ylmethyl]-3-propyl-urea | 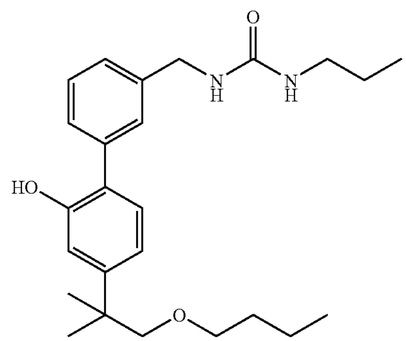 | 413 |
| 16 | 1-Ethyl-3-{2'- hydroxy-4'-[2-(2-methoxy-ethoxy)-1,1-dimethyl-ethyl]-biphenyl-2-ylmethyl}-urea | 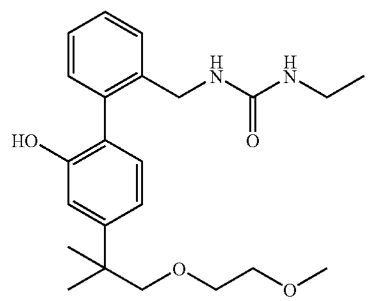 | 401 |
| 17 | 1-Ethyl-3-{2'- hydroxy-4'-[2-(2-methoxy-ethoxy)-1,1-dimethyl-ethyl]-biphenyl-3-ylmethyl}-urea | 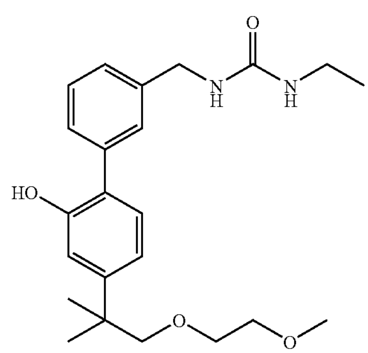 | 401 |
| 18 | 1-[4'-(1,1-Dimethyl-6-morpholin-4-yl-6-oxo-hexyl)-2'-hydroxy-biphenyl-2-ylmethyl]-3-ethyl-urea | 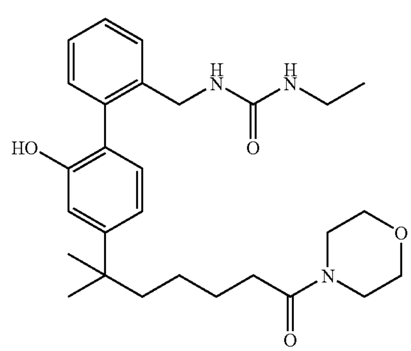 | 482 |

TABLE 4-continued

| Compound | Name | Structure | M + 1 |
|---|---|---|---|
| 19 | 1-[4'-(1,1-Dimethyl-6-morpholin-4-yl-6-oxo-hex-4-enyl)-2'-hydroxy-biphenyl-2-yl-methyl]-3-ethyl-urea | 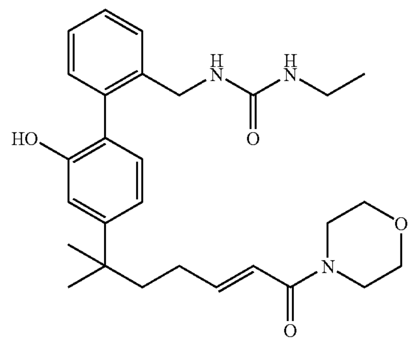 | 480 |
| 20 | 1-[4'-(1,1-Dimethyl-6-morpholin-4-yl-6-oxo-hexyl)-2'-hydroxy-biphenyl-3-yl-methyl]-3-ethyl-urea | 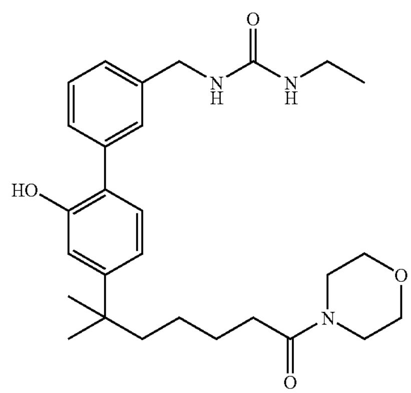 | 482 |
| 21 | 1-[4'-(1,1-Dimethyl-6-morpholin-4-yl-6-oxo-hexyl)-2'-hydroxy-biphenyl-2-yl-methyl]-3-methyl-urea | 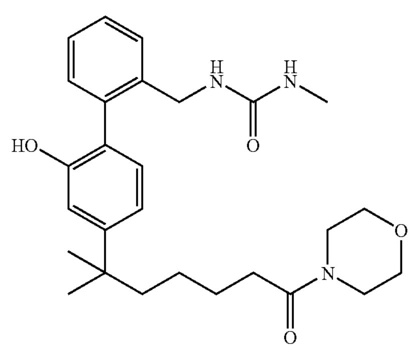 | 468 |
| 22 | 1-[4'-(1,1-Dimethyl-6-morpholin-4-yl-6-oxo-hexyl)-2'-hydroxy-biphenyl-2-yl-methyl]-3-isopropyl-urea | 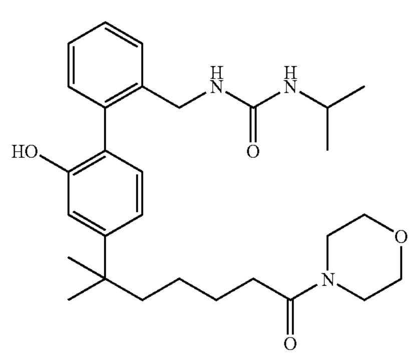 | 496 |

TABLE 4-continued

| Compound | Name | Structure | M + 1 |
| --- | --- | --- | --- |
| 23 | 1-[4'-(1,1-Dimethyl-6-morpholin-4-yl-6-oxo-hexyl)-2'-hydroxy-biphenyl-2-yl-methyl]-3-(4-methoxy-phenyl)-urea | 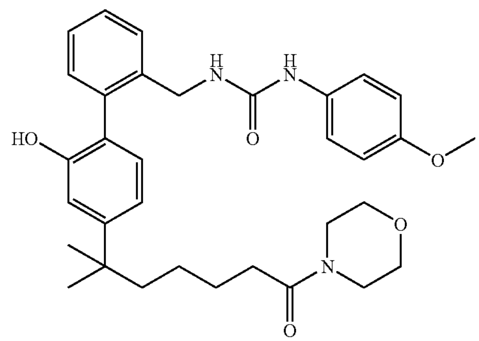 | 560 |
| 24 | {3-[4'-(1,1-Dimethyl-6-morpholin-4-yl-6-oxo-hexyl)-2'-hydroxy-biphenyl-2-yl-methyl]-ureido}-acetic acid ethyl ester | 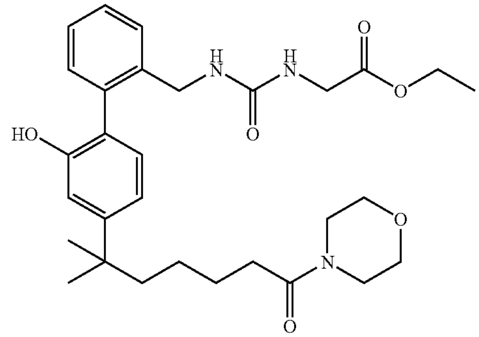 | 540 |
| 25 | 1-(4-Dimethylamino-phenyl)-3-[4'-(1,1-dimethyl-6-morpho-lin-4-yl-6-oxo-hexyl)-2'-hydroxy-biphenyl-2-yl-methyl]-urea | 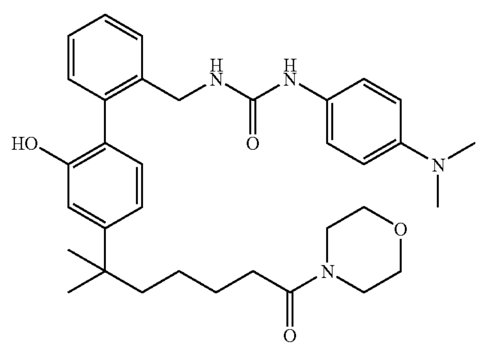 | 573 |
| 26 | 1-(3-Cyano-phenyl)-3-[4'-(1,1-dimethyl-6-morpholin-4-yl-6-oxo-hexyl)-2'-hydroxy-biphenyl-2-yl-methyl]-urea | 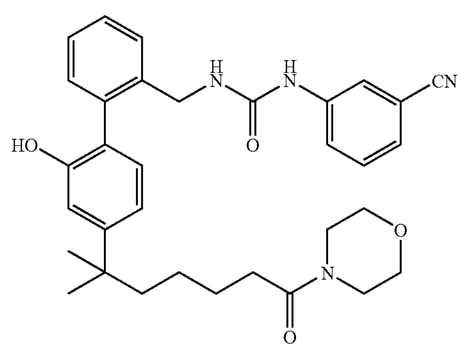 | 555 |

TABLE 4-continued

| Compound | Name | Structure | M + 1 |
|---|---|---|---|
| 27 | 1-[4'-(1,1-Dimethyl-6-morpholin-4-yl-6-oxo-hexyl)-2'-hydroxy-biphenyl-2-yl-methyl]-3-(3-methoxy-phenyl)-urea | 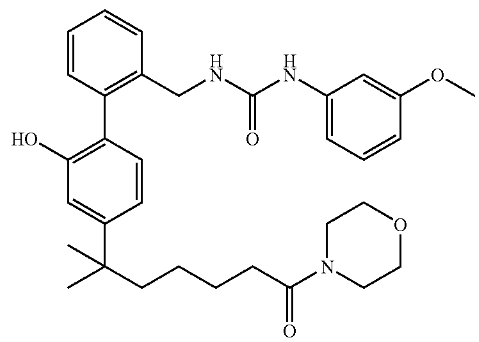 | 560 |
| 28 | 1-[4'-(1,1-Dimethyl-6-morpholin-4-yl-6-oxo-hexyl)-2'-hydroxy-biphenyl-3-ylmethyl]-3-methyl-urea | 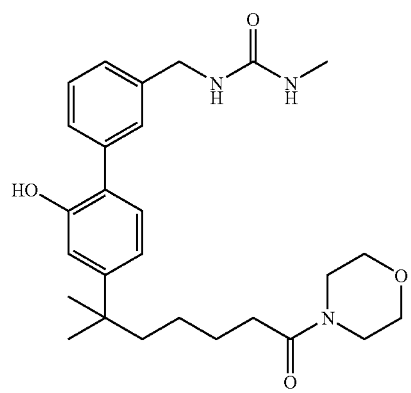 | 468 |
| 29 | 1-[4'-(1,1-Dimethyl-6-morpholin-4-yl-6-oxo-hexyl)-2'-hydroxy-biphenyl-3-yl-methyl]-3-isopropyl-urea | 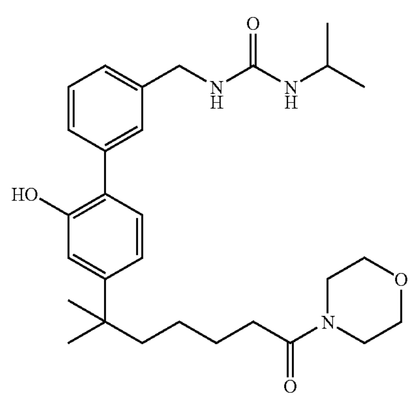 | 496 |
| 30 | 1-[4'-(1,1-Dimethyl-6-morpholin-4-yl-6-oxo-hexyl)-2'-hydroxy-biphenyl-3-yl-methyl]-3-(4-methoxy-phenyl)-urea | 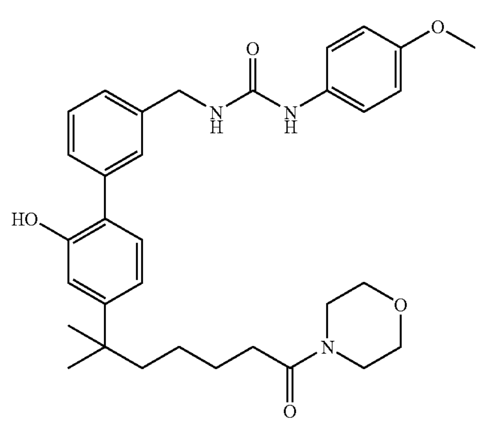 | 560 |

TABLE 4-continued
| Compound | Name | Structure | M + 1 |
|---|---|---|---|
| 31 | {3-[4'-(1,1-Dimethyl-6-morpholin-4-yl-6-oxo-hexyl)-2'-hydroxy-biphenyl-3-yl-methyl]-ureido}-acetic acid ethyl ester | 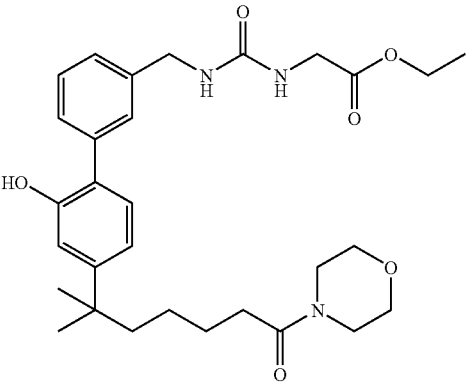 | 540 |
| 32 | 1-(4-Dimethylamino-phenyl)-3-[4'-(1,1-dimethyl-6-morpholin-4-yl-6-oxo-hexyl)-2'-hydroxy-biphenyl-3-yl-methyl]-urea | 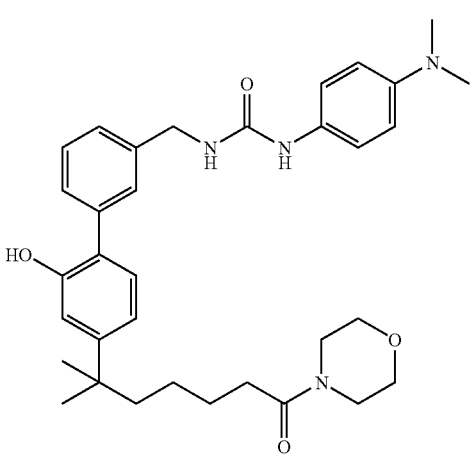 | 573 |
| 33 | 1-(3-Cyano-phenyl)-3-[4'-(1,1-dimethyl-6-morpholin-4-yl-6-oxo-hexyl)-2'-hydroxy-biphenyl-3-yl-methyl]-urea | 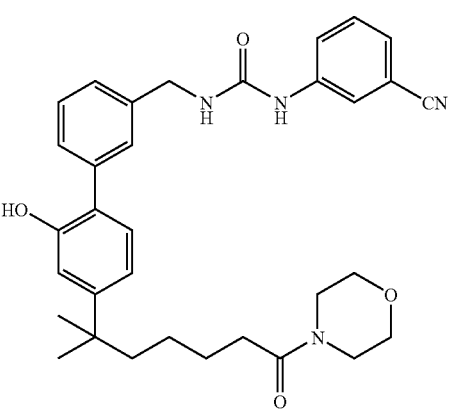 | 555 |

TABLE 4-continued

| Compound | Name | Structure | M + 1 |
|---|---|---|---|
| 34 | 1-[4'-(1,1-Dimethyl-6-morpholin-4-yl-6-oxo-hexyl)-2'-hydroxy-biphenyl-3-ylmethyl]-3-(3-methoxy-phenyl)-urea | 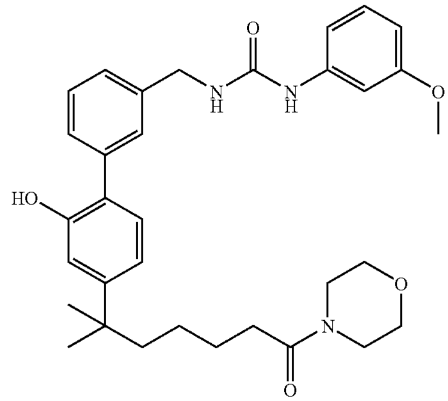 | 560 |
| 35 | N-(4-{3'-[(3-Ethyl-ureido)-methyl]-2-hydroxy-biphenyl-4-yl}-4-methyl-pentyl)-2,2-dimethyl-propionamide | 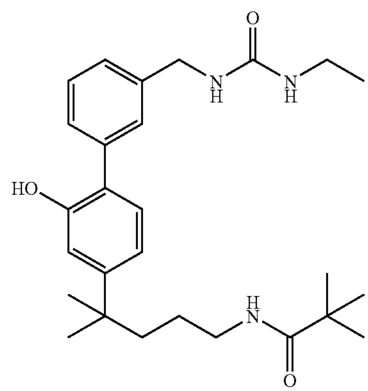 | 454 |
| 36 | 1-(4-{2'-[(3-Ethyl-ureido)-methyl]-2-hydroxy-biphenyl-4-yl}-4-methyl-pentyl)-3-isopropyl-urea | 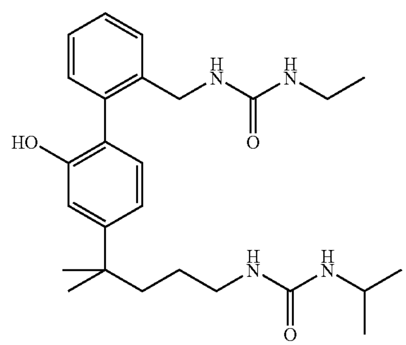 | 455 |
| 37 | 1-(4-{3'-[(3-Ethyl-ureido)-methyl]-2-hydroxy-biphenyl-4-yl}-4-methyl-pentyl)-3-isopropyl-urea | 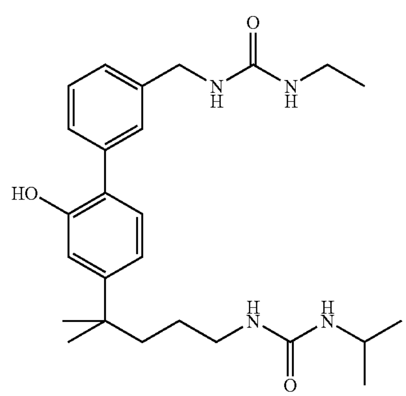 | 455 |

TABLE 4-continued

| Compound | Name | Structure | M + 1 |
|---|---|---|---|
| 38 | Ethyl-carbamic acid 4-{3'-[(3-ethyl-ureido)-methyl]-2-hydroxy-biphenyl-4-yl}-4-methyl-pentyl ester | 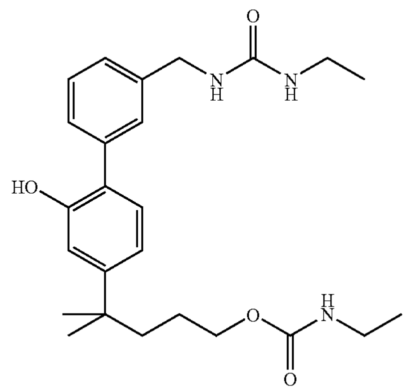 | 442 |
| 39 | Ethyl-carbamic acid 4-{2'-[(3-ethyl-ureido)-methyl]-2-hydroxy-biphenyl-4-yl}-4-methyl-pentyl ester | 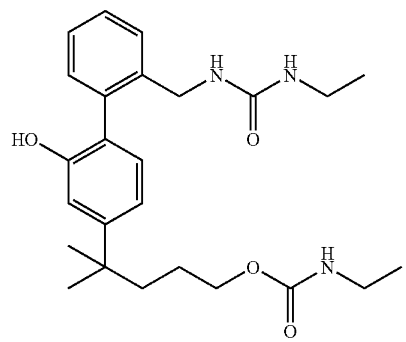 | 442 |
| 40 | Morpholine-4-carboxylic acid (4-{3'-[(3-ethyl-ureido)-methyl]-2-hydroxy-biphenyl-4-yl}-4-methyl-pentyl)-amide | 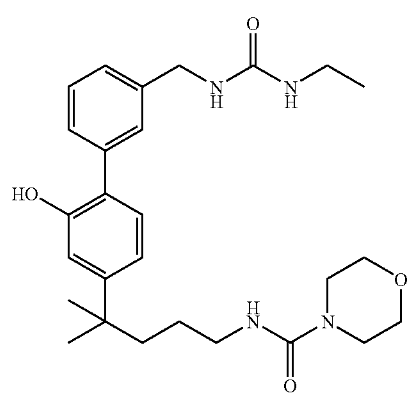 | 483 |
| 41 | Tetrahydrofuran-2-carboxylic acid [4'-(1,1-dimethyl-6-morpholin-4-yl-6-oxo-hexyl)-2'-hydroxy-biphenyl-3-ylmethyl]-amide | 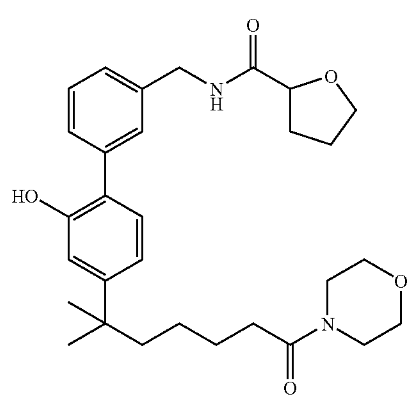 | 509 |

TABLE 4-continued

| Compound | Name | Structure | M + 1 |
|---|---|---|---|
| 42 | Furan-2-carboxylic acid [4'-(1,1-dimethyl-6-morpholin-4-yl-6-oxo-hexyl)-2'-hydroxy-biphenyl-3-ylmethyl]-amide | 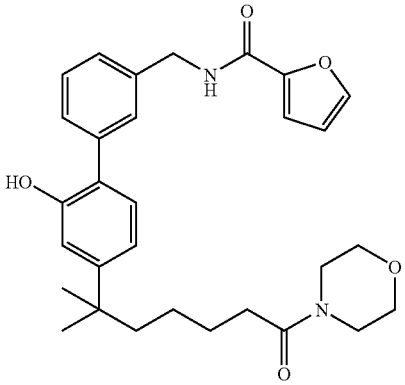 | 505 |
| 43 | Furan-3-carboxylic acid [4'-(1,1-dimethyl-6-morpholin-4-yl-6-oxo-hexyl)-2'-hydroxy-biphenyl-3-ylmethyl]-amide | 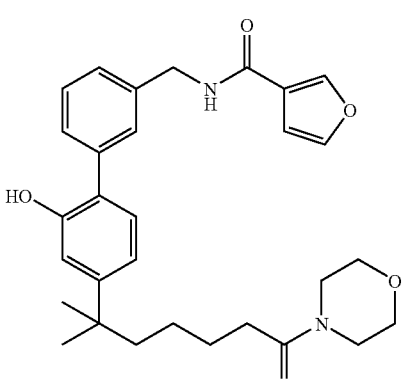 | 505 |
| 44 | Isoxazole-5-carboxylic acid [4'-(1,1-dimethyl-6-morpholin-4-yl-6-oxo-hexyl)-2'-hydroxy-biphenyl-3-ylmethyl]-amide | 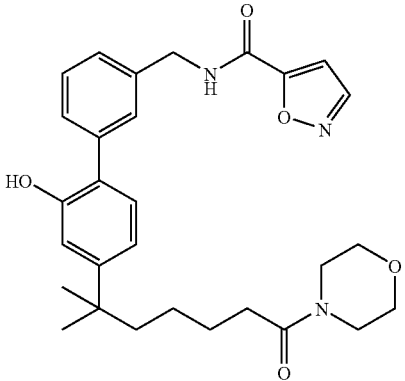 | 506 |
| 45 | 2,5-Dimethyl-furan-3-carboxylic acid [4'-(1,1-dimethyl-6-morpholin-4-yl-6-oxo-hexyl)-2'-hydroxy-biphenyl-3-ylmethyl]-amide | 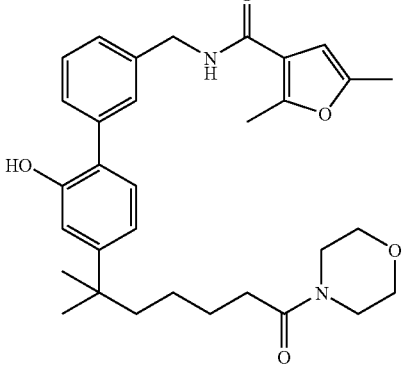 | 533 |

TABLE 4-continued

| Compound | Name | Structure | M + 1 |
|---|---|---|---|
| 46 | N-[4'-(1,1-Dimethyl-6-morpholin-4-yl-6-oxo-hexyl)-2'-hydroxy-biphenyl-3-ylmethyl]-nicotinamide | 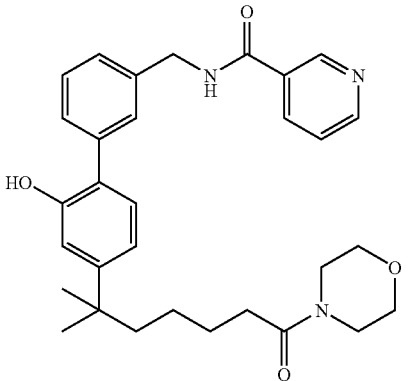 | 516 |
| 47 | Pyrazine-2-carboxylic acid [4'-(1,1-dimethyl-6-morpholin-4-yl-6-oxo-hexyl)-2'-hydroxy-biphenyl-3-ylmethyl]-amide | 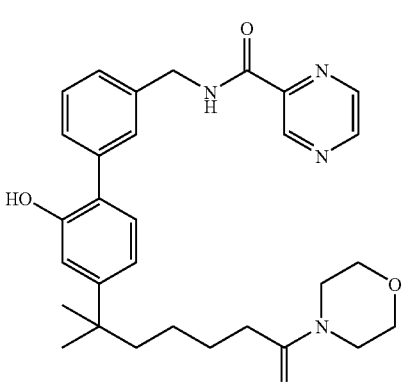 | 517 |
| 48 | 1-Methyl-1H-pyrrole-2-carboxylic acid [4'-(1,1-dimethyl-6-morpholin-4-yl-6-oxo-hexyl)-2'-hydroxy-biphenyl-3-ylmethyl]-amide | 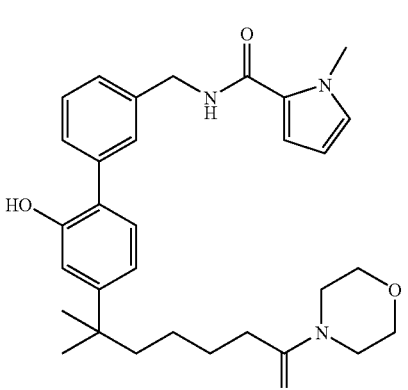 | 518 |
| 49 | 5-Methyl-isoxazole-3-carboxylic acid [4'-(1,1-dimethyl-6-morpholin-4-yl-6-oxo-hexyl)-2'-hydroxy-biphenyl-3-ylmethyl]-amide | 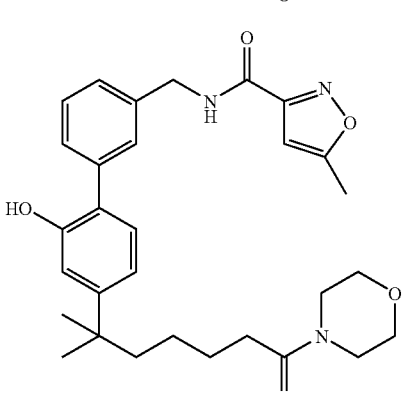 | 520 |

TABLE 4-continued

| Compound | Name | Structure | M + 1 |
|---|---|---|---|
| 50 | Thiophene-3-carboxylic acid [4'-(1,1-dimethyl-6-morpholin-4-yl-6-oxo-hexyl)-2'-hydroxy-biphenyl-3-ylmethyl]-amide | 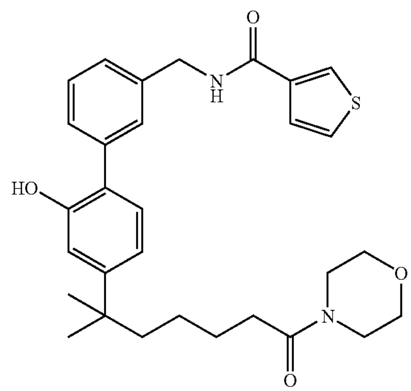 | 521 |
| 51 | 5-Oxo-pyrrolidine-2-carboxylic acid [4'-(1,1-dimethyl-6-morpholin-4-yl-6-oxo-hexyl)-2'-hydroxy-biphenyl-3-ylmethyl]-amide | 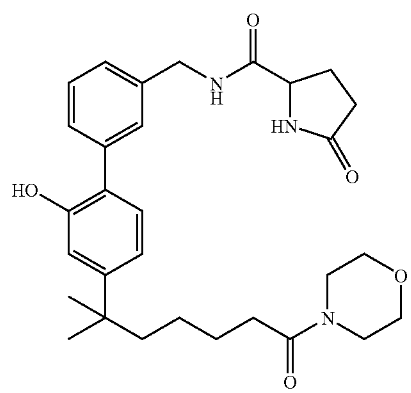 | 522 |
| 52 | [1,2,3]Thiadazole-4-carboxylic acid [4'-(1,1-dimethyl-6-morpholin-4-yl-6-oxo-hexyl)-2'-hydroxy-biphenyl-3-ylmethyl]-amide | 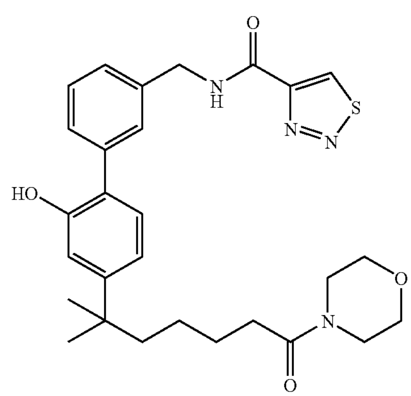 | 523 |
| 53 | 5-Methyl-pyrazine-2-carboxylic acid [4'-(1,1-dimethyl-6-morpholin-4-yl-6-oxo-hexyl)-2'-hydroxy-biphenyl-3-ylmethyl]-amide | 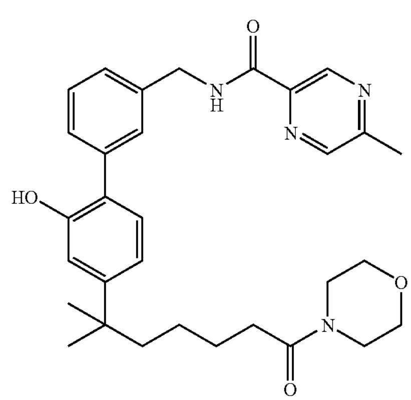 | 531 |

TABLE 4-continued

| Compound | Name | Structure | M + 1 |
|---|---|---|---|
| 54 | N-[4'-(1,1-Dimethyl-6-morpholin-4-yl-6-oxo-hexyl)-2'-hydroxy-biphenyl-3-ylmethyl]-1-hydroxy-isonicotinamide N-oxide | 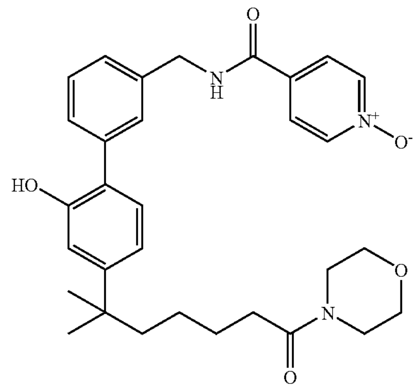 | 532 |
| 55 | 1,5-Dimethyl-1H-pyrazole-3-carboxylic acid [4'-(1,1-dimethyl-6-morpholin-4-yl-6-oxo-hexyl)-2'-hydroxy-biphenyl-3-ylmethyl]-amide | 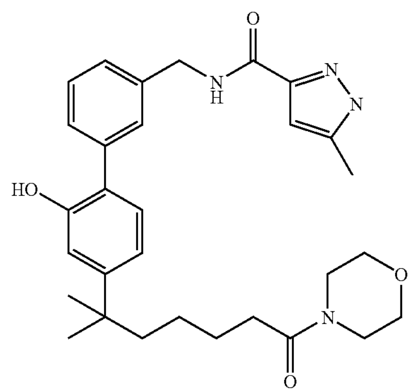 | 533 |
| 56 | Tetrahydro-furan-2-carboxylic acid [4'-(1,1-dimethyl-6-morpholin-4-yl-6-oxo-hexyl)-2'-hydroxy-biphenyl-2-ylmethyl]-amide | 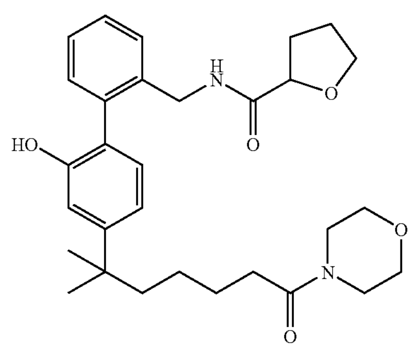 | 509 |
| 57 | Furan-2-carboxylic acid [4'-(1,1-dimethyl-6-morpholin-4-yl-6-oxo-hexyl)-2'-hydroxy-biphenyl-2-ylmethyl]-amide | 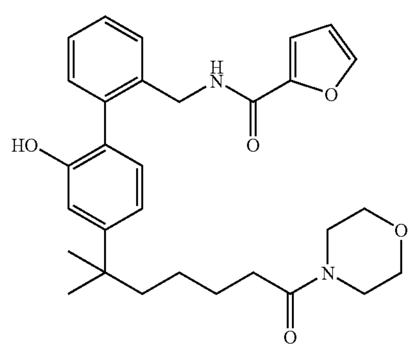 | 505 |

TABLE 4-continued

| Compound | Name | Structure | M + 1 |
|---|---|---|---|
| 58 | Furan-3-carboxylic acid [4'-(1,1-dimethyl-6-morpholin-4-yl-6-oxo-hexyl)-2'-hydroxy-biphenyl-2-ylmethyl]-amide | 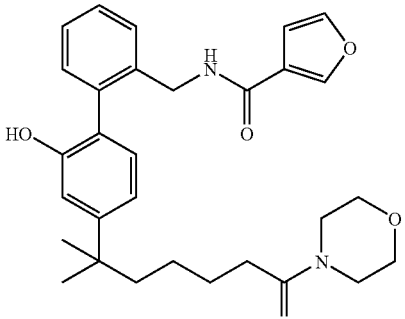 | 505 |
| 59 | Isoxazole-5-carboxylic acid [4'-(1,1-dimethyl-6-morpholin-4-yl-6-oxo-hexyl)-2'-hydroxy-biphenyl-2-ylmethyl]-amide | 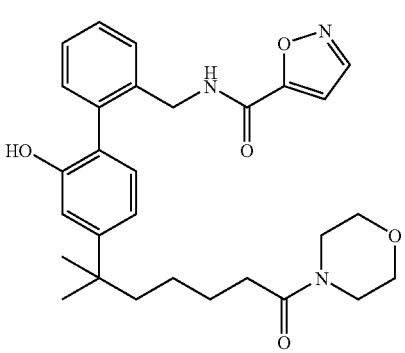 | 506 |
| 60 | 2,5-Dimethyl-furan-3-carboxylic acid [4'-(1,1-dimethyl-6-morpholin-4-yl-6-oxo-hexyl)-2'-hydroxy-biphenyl-2-ylmethyl]-amide | 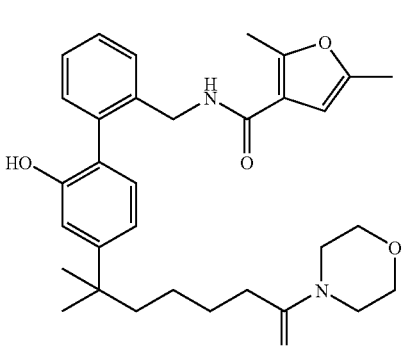 | 533 |
| 61 | N-[4'-(1,1-Dimethyl-6-morpholin-4-yl-6-oxo-hexyl)-2'-hydroxy-biphenyl-3-ylmethyl]-nicotinamide | 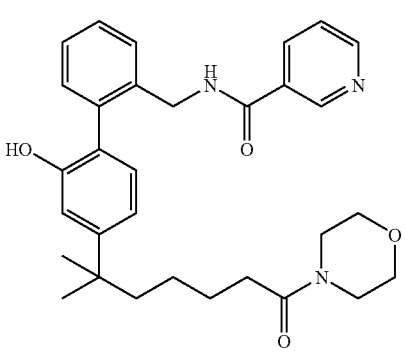 | 516 |

TABLE 4-continued

| Compound | Name | Structure | M + 1 |
|---|---|---|---|
| 62 | Pyrazine-2-carboxylic acid [4'-(1,1-dimethyl-6-morpholin-4-yl-6-oxo-hexyl)-2'-hydroxy-biphenyl-2-ylmethyl]-amide | 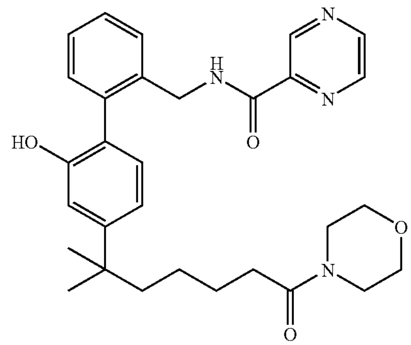 | 517 |
| 63 | 1-Methyl-1H-pyrrole-2-carboxylic acid [4'-(1,1-dimethyl-6-morpholin-4-yl-6-oxo-hexyl)-2'-hydroxy-biphenyl-2-ylmethyl]-amide | 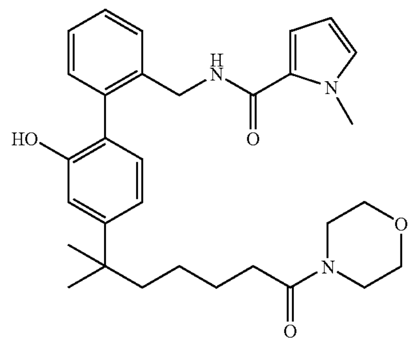 | 518 |
| 64 | 5-Methyl-isoxazole-3-carboxylic acid [4'-(1,1-dimethyl-6-morpholin-4-yl-6-oxo-hexyl)-2'-hydroxy-biphenyl-2-ylmethyl]-amide | 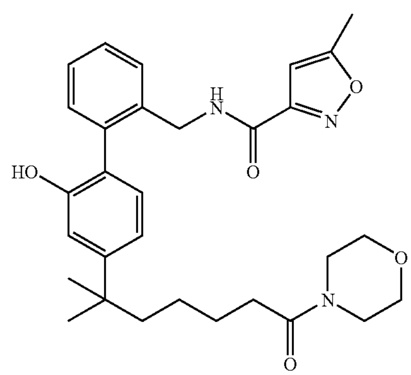 | 520 |
| 65 | Thiophene-3-carboxylic acid [4'-(1,1-dimethyl-6-morpholin-4-yl-6-oxo-hexyl)-2'-hydroxy-biphenyl-2-ylmethyl]-amide | 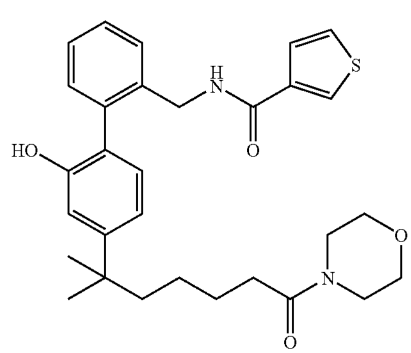 | 521 |

TABLE 4-continued

| Compound | Name | Structure | M + 1 |
|---|---|---|---|
| 66 | 5-Oxo-pyrrolidine-2-carboxylic acid [4'-(1,1-dimethyl-6-morpholin-4-yl-6-oxo-hexyl)-2'-hydroxy-biphenyl-2-ylmethyl]-amide | 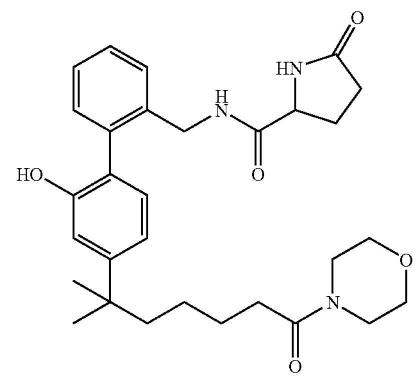 | 522 |
| 67 | [1,2,3]Thiadazole-4-carboxylic acid [4'-(1,1-dimethyl-6-morpholin-4-yl-6-oxo-hexyl)-2'-hydroxy-biphenyl-2-ylmethyl]-amide | 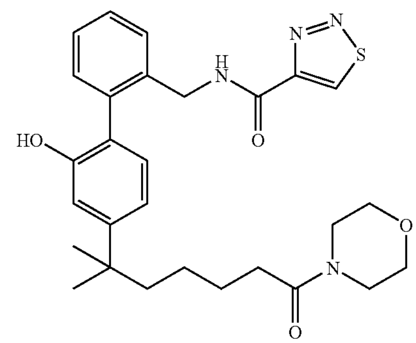 | 523 |
| 68 | 5-Methyl-pyrazine-2-carboxylic acid [4'-(1,1-dimethyl-6-morpholin-4-yl-6-oxo-hexyl)-2'-hydroxy-biphenyl-2-ylmethyl]-amide | 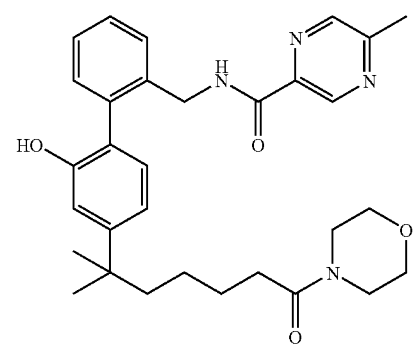 | 531 |
| 69 | Tetrahydrofuran-2-carboxylic acid [4'-(1,1-dimethyl-6-morpholin-4-yl-6-oxo-hexyl)-2'-hydroxy-biphenyl-3-ylmethyl]-amide | 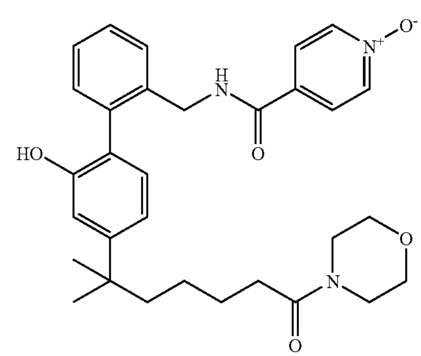 | 532 |

TABLE 4-continued

| Compound | Name | Structure | M + 1 |
|---|---|---|---|
| 70 | Furan-2-carboxylic acid [4'-(1,1-dimethyl-6-morpholin-4-yl-6-oxo-hexyl)-2'-hydroxy-biphenyl-3-ylmethyl]-amide | 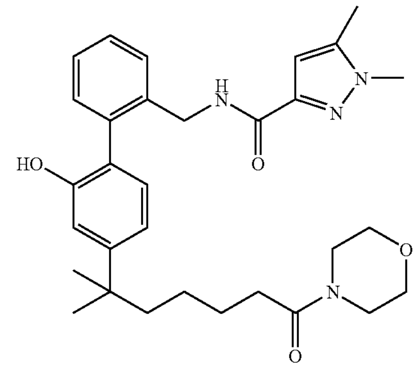 | 533 |
| 71 | 4'-(1,1-dimethyl-6-morpholin-4-yl-6-oxo-hexyl)-2'-hydroxy-biphenyl-3-ylmethyl]-methane sulfonamide | 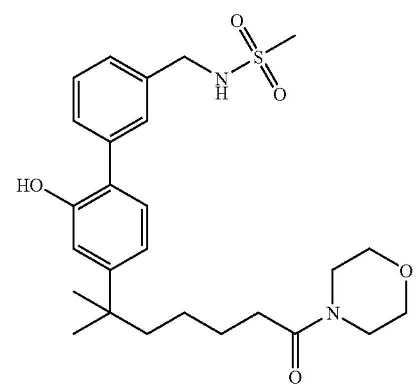 | 489 |
| 72 | 4'-(1,1-dimethyl-6-morpholin-4-yl-6-oxo-hexyl)-2'-hydroxy-biphenyl-2-ylmethyl]-methane sulfonamide | 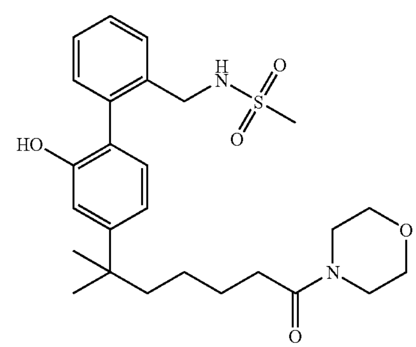 | 489 |
| 73 | 2-amino-N-(4-(3'-((3-ethyl-ureido)methyl)-2-hydroxy-biphenyl-4-yl)-4-methyl-pentyl)-2-methylpropanamide hydrochloride | 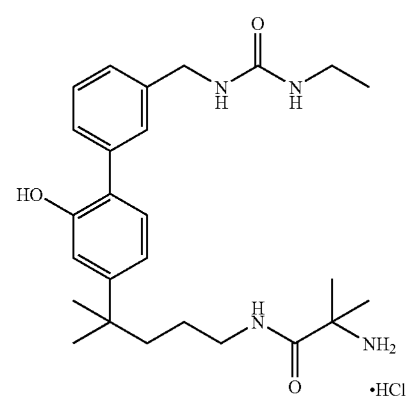 | 455 |

TABLE 4-continued

| Compound | Name | Structure | M + 1 |
|---|---|---|---|
| 74 | N-(4-3'-((3-ethylureido)-methyl)-2-hydroxybiphenyl-4-yl)-4-methylpentyl)-nicotinamide hydrochloride | 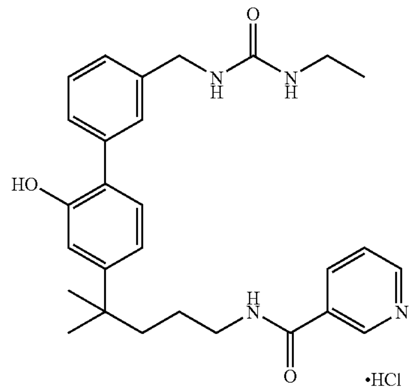 | 475 |
| 75 | 1-ethyl-3-((2'-methoxy-4'-(2-methyl-7-morpholino-7-oxoheptan-2-yl)biphenyl-3-yl)methyl)urea | 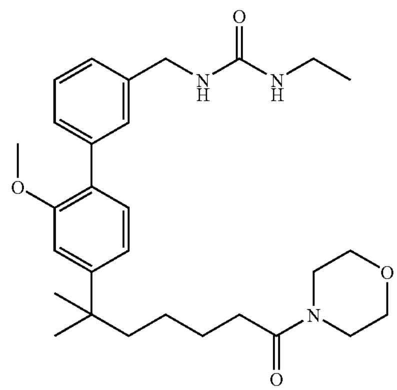 | 496 |
| 76 | N-(4-3'-((3-ethylureido)-methyl)-2-methoxybiphenyl-4-yl)-4-methylpentyl)-pivalamide | 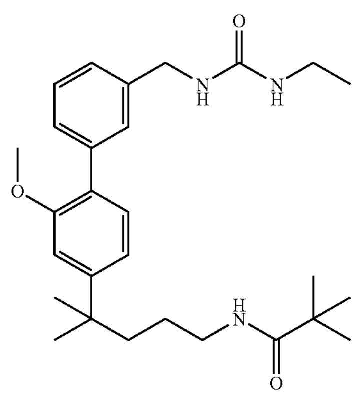 | 468 |
| 77 | 1-ethyl-3-((2'-hydroxy-4'-(2-methyl-7-morpholinoheptan-2-yl)biphenyl-3-yl)methyl)-urea | 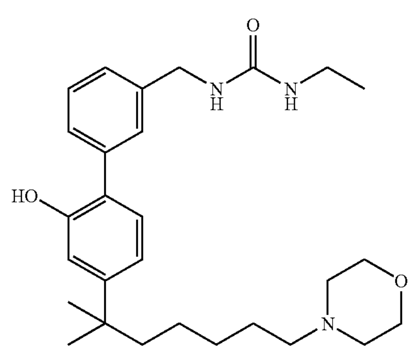 | 468 |

| Compound | Name | Structure | M + 1 |
|---|---|---|---|
| 78 | 1-ethyl-3-((2'-hydroxy-4'-(2-methyl-5-(neopentylamino)-pentan-2-yl)biphenyl-3-yl)-methyl)urea | 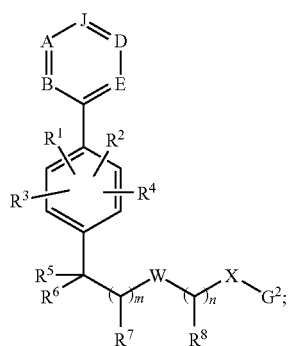 | 440 |

When ranges are used herein for physical properties, such as molecular weight, or chemical properties, such as chemical formulae, all combinations and subcombinations of ranges and specific embodiments therein are intended to be included.

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A compound of formula I:

I

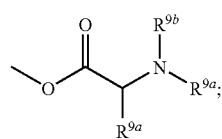

wherein:

$R^1$, $R^2$, $R^3$, and $R^4$ are each independently H, alkyl, —$OR^{9a}$, —$N(R^{10})(R^{11})$, —$C(=O)N(R^{12})(R^{13})$, —$C(=O)$—$OR^{9b}$, —$OP(=O)(OR^{9c})(OR^{9d})$, —CN, or $R^5$ and $R^6$ are each independently H or alkyl, or taken together with the carbon atom to which they are attached form a 3- to 8-membered carbocyclic ring, wherein 1 to 3 of the ring carbon atoms independently may be optionally replaced by —O—, —S—, —S(=O)—, —S(=O)$_2$—, or —N($R^{9e}$)—;

$R^7$ is H, alkyl, halogen, or —$OR^{9f}$;

each $R^8$ is independently H or alkyl;

A, B, D, and E are each independently N, $CR^{14a}$, C—[C($R^{15a}$)($R^{16a}$)]$_p$—N($R^{17}$)-$G^1$, or C—[C($R^{15b}$)($R^{16b}$)]$_p$—OC(=O)—N($R^{18a}$)($R^{18b}$);

J is N or $CR^{14b}$, provided that no more than two of A, B, D, E, and J are N;

each $G^1$ is independently —S(=O)$_2$$R^{19}$, —S(=O)$_2$N($R^{20a}$)($R^{20b}$), —C(=O)-heterocycloalkyl, —C(=O)-heteroaryl, —C(=O)—N($R^{18c}$)($R^{18d}$), —C(=CHNO$_2$)—N($R^{18c}$)($R^{18d}$), or —C(=N—CN)—N($R^{18e}$)($R^{18f}$);

$G^2$ is acyl;

each $R^{9a}$, $R^{9b}$, $R^{9c}$, $R^{9d}$, $R^{9e}$, and $R^{9f}$ is independently H or alkyl;

each $R^{10}$, $R^{11}$, $R^{12}$, and $R^{13}$ is independently H, alkyl, alkenyl, aryl, or heteroaryl, or each $R^{10}$ and $R^{11}$ or $R^{12}$ and $R^{13}$, taken together with the nitrogen atom to which they are attached, independently form a 4- to 8-membered heterocyclic ring wherein 1 or 2 of the ring carbon atoms independently may be optionally replaced by —O—, —S—, —S(=O)—, —S(=O)$_2$—, —NH—, —N(alkyl)-, —N(C(=O)—$R^{9a}$)—, or —N(S(=O)$_2$—$R^{9a}$)—;

each $R^{14a}$ and $R^{14b}$ is independently H, halogen, alkyl, —CH$_2$F, —CHF$_2$, —CF$_3$, —CN, —(CH$_2$)$_r$-OH, or —(CH$_2$)$_r$—O-alkyl;

each $R^{18a}$, $R^{18b}$, $R^{18c}$, $R^{18d}$, $R^{18e}$, $R^{18f}$, $R^{20a}$, and $R^{20b}$ is independently H, alkyl, alkenyl, or aryl, or each $R^{18a}$ and $R^{18b}$ or $R^{18c}$ and $R^{18d}$ or $R^{20a}$ and $R^{20b}$, taken together with the nitrogen atom to which they are attached independently form a 4- to 8-membered heterocyclic ring wherein 1 or 2 of the ring carbon atoms independently may be optionally replaced by —O—, —S—, —S(=O)$_2$—, —NH—, —N(alkyl)-, —N(C(=O)—$R^{9a}$)—, or —N(S(=O)$_2$—$R^{9a}$)—;

each $R^{19}$ is independently H, alkyl, aryl, OH, or —O-alkyl;

W is a single bond;

X is —N($R^{21}$)—;

each $R^{15a}$, $R^{15b}$, $R^{16a}$, $R^{16b}$, $R^{17}$, and $R^{21}$ is independently H or alkyl; or $R^{17}$ and $R^{18c}$, taken together with the atoms through which they are connected form a 4- to 8-membered heterocyclic ring wherein 1 or 2 of the ring carbon atoms independently may be optionally replaced by —O—, —S—, —S(=O)—, —S(=O)$_2$—, —NH—, —N(alkyl)-, —N(C(=O)—R$^{9a}$)—, or —N(S(=O)$_2$—R$^{9a}$)—;

m is 1;

n is 2;

each p is independently an integer from 0 to 5; and each r is independently an integer from 0 to 4;

with the proviso that:

at least one of A, B, D, and E is C—[C(R$^{15a}$)(R$^{16a}$)]$_p$—N(R$^{17}$)-G$^1$ or C—[C(R$^{15b}$)(R$^{16b}$)]$_p$—OC(=O)—N(R$^{18a}$)(R$^{18b}$);

or a pharmaceutically acceptable salt thereof.

2. A compound according to claim 1, wherein R$^1$ is —OR$^{9a}$ or —N(R$^{10}$)(R$^{11}$).

3. A compound according to claim 2, wherein R$^1$ is —OR$^{9a}$.

4. A compound according to claim 3, wherein R$^1$ is —OH.

5. A compound according to claim 1, wherein R$^3$ and R$^4$ are each independently H or alkyl.

6. A compound according to claim 5, wherein R$^3$ and R$^4$ are each H.

7. A compound according to claim 1, wherein R$^5$ and R$^6$ are each independently H or alkyl, or taken together with the carbon atom to which they are attached form a 3- to 8-membered carbocyclic ring, wherein one of the ring carbon atoms may be optionally replaced by —O—, —S—, —S(=O)—, —S(=O)$_2$—, or —N(R$^{9e}$)—.

8. A compound according to claim 7, wherein R$^5$ and R$^6$ are each independently H or alkyl, or taken together with the carbon atom to which they are attached form a 3- to 6-membered carbocyclic ring, wherein one of the ring carbon atoms may be optionally replaced by —O—, —S—, —S(=O)—, —S(=O)$_2$—, or —N(R$^{9e}$)—.

9. A compound according to claim 8, wherein R$^5$ and R$^6$ are each independently H or alkyl, or taken together with the carbon atom to which they are attached form a 3- to 6-membered carbocyclic ring.

10. A compound according to claim 9, wherein R$^5$ and R$^6$ are each independently H or alkyl.

11. A compound according to claim 10 wherein R$^5$ and R$^6$ are methyl.

12. A compound according to claim 1, wherein R$^7$ and R$^8$ are each independently H or alkyl.

13. A compound according to claim 12, wherein R$^7$ and R$^8$ are H.

14. A compound according to claim 1, wherein A, B, D, and E are each independently CR$^{14a}$, C—[C(R$^{15a}$)(R$^{16a}$)]$_p$—N(R$^{17}$)-G$^1$, or C—[C(R$^{15b}$)(R$^{16b}$)]$_p$—OC(=O)—N(R$^{18a}$)(R$^{18b}$).

15. A compound according to claim 14, wherein A, B, D, and E are each independently CR$^{14a}$ or C—[C(R$^{15a}$)(R$^{16a}$)]$_p$—N(R$^{17}$)-G$^1$.

16. A compound according to claim 15, wherein G$^1$ is —C(=O)—N(R$^{18c}$)(R$^{18d}$) and R$^{17}$ and R$^{18c}$, taken together with the atoms through which they are connected form a 4- to 8-membered heterocyclic ring wherein 1 or 2 of the ring carbon atoms independently may be optionally replaced by —O—, —S—, —S(=O)—, —S(=O)$_2$—, —NH—, —N(alkyl)-.

17. A compound according to claim 15, wherein R$^{17}$ is H or alkyl.

18. A compound according to claim 15, wherein two or three of A, B, D, and E are each independently CR$^{14a}$.

19. A compound according to claim 1, wherein J is CR$^{14b}$.

20. A compound according to claim 1, wherein each G$^1$ is independently —S(=O)$_2$R$^{19}$, —C(=O)-heterocycloalkyl, —C(=O)-heteroaryl, or —C(=O)—N(R$^{18c}$)(R$^{18d}$).

21. A compound according to claim 20, wherein each G$^1$ is —C(=O)-heteroaryl or —C(=O)—N(R$^{18c}$)(R$^{18d}$).

22. A compound according to claim 1 wherein R$^{9a}$ is H.

23. A compound according to claim 1, wherein R$^{14a}$ is H.

24. A compound according to claim 1, wherein R$^{14b}$ is H.

25. A compound according to claim 1, wherein at least one of R$^{14a}$ and R$^{14b}$ is —(CH$_2$)$_r$—OH or —(CH$_2$)$_r$—O-alkyl.

26. A compound according to claim 1 wherein each R$^{18c}$ and R$^{18d}$ is independently H, alkyl, or aryl, or each R$^{18c}$ and R$^{18d}$, taken together with the nitrogen atom to which they are attached independently form a 4- to 8-membered heterocyclic ring wherein 1 or 2 of the ring carbon atoms independently may be optionally replaced by —O—, —S—, —S(=O)—, —S(=O)$_2$—, —NH—, or —N(alkyl)-.

27. A compound according to claim 26 wherein each R$^{18c}$ and R$^{18d}$ is independently H or alkyl optionally substituted with alkoxycarbonyl.

28. A compound according to claim 27, wherein at least one of R$^{18c}$ and R$^{18d}$ is alkyl substituted with C$_1$-C$_3$ alkoxycarbonyl.

29. A compound according to claim 28, wherein at least one of R$^{18c}$ and R$^{18d}$ is —CH$_2$C(=O)—OCH$_2$CH$_3$.

30. A compound according to claim 26, wherein one of R$^{18c}$ and R$^{18d}$ is optionally substituted aryl.

31. A compound according to claim 30, wherein one of R$^{18c}$ and R$^{18d}$ is phenyl substituted with alkoxy, cyano, or dialkylamino.

32. A compound according to claim 31, wherein one of R$^{18c}$ and R$^{18d}$ is phenyl substituted with meta-alkoxy, meta-cyano, meta-dialkylamino, para-alkoxy, para-cyano, or para-dialkylamino.

33. A compound according to claim 1, wherein at least one of R$^{15a}$, R$^{16a}$, and R$^{21}$ is H.

34. A compound according to claim 33, wherein R$^{15a}$, R$^{16a}$, and R$^{21}$ are each H.

35. A compound according to claim 1, wherein at least one of R$^{17}$ and R$^{18c}$ is H.

36. A compound according to claim 1, wherein p is 1.

37. A compound according to claim 1, wherein r is 1 or 2.

38. A compound according to claim 1, wherein one of A and D is C—[C(R$^{15a}$)(R$^{16a}$)]$_p$—N(R$^{17}$)-G$^1$ or one of B and E is C—[C(R$^{15a}$)(R$^{16a}$)]$_p$—N(R$^{17}$)-G$^1$.

39. A compound according to claim 38, wherein R$^{17}$ is H.

40. A compound according to claim 39, wherein R$^1$ is —OR$^{9a}$.

41. A compound according to claim 40 wherein R$^2$, R$^3$, and R$^4$ are each H.

42. A compound according to claim 41, wherein R$^5$ and R$^6$ are each alkyl.

43. A compound according to claim 42, wherein R$^5$ and R$^6$ are each independently C$_1$-C$_3$ alkyl.

44. A compound according to claim 43, wherein R$^5$ and R$^6$ are each methyl.

45. A compound according to claim 44, wherein R$^7$ and R$^8$ are each H.

46. A compound according to claim 45, wherein J is CR$^{14b}$, one of D and E is C—[C(R$^{15a}$)(R$^{16a}$)]$_p$—N(R$^{17}$)-G$^1$, and A and B and the other of D and E are each independently CR$^{14a}$.

47. A compound according to claim 46, of formula IIa or IIb:

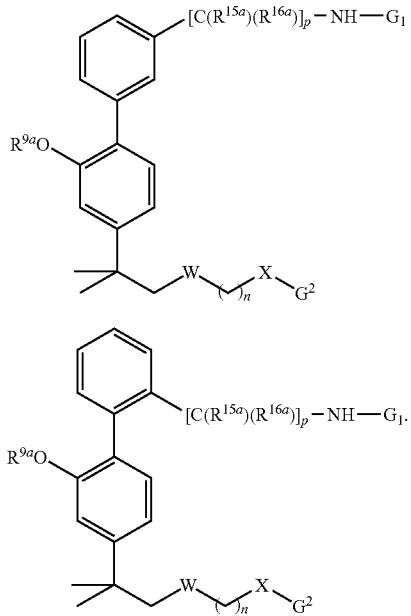

48. A compound according to claim 47 wherein $G^2$ is —C(=O)—$C_1$-$C_6$ alkyl.

49. A compound according to claim 47, wherein $G^1$ is —C(=O)—N($R^{18c}$)($R^{18d}$).

50. A compound according to claim 49, wherein $G^1$ is —C(=O)—NH($C_1$-$C_3$ alkyl).

51. A compound according to claim 47, wherein $G^1$ is —C(=O)-heterocycloalkyl.

52. A compound according to claim 51, wherein $G^1$ is:

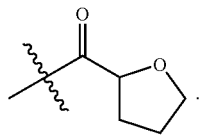

53. A compound according to claim 47, wherein $G^1$ is —S(=O)$_2$-alkyl.

54. A compound according to claim 53, wherein $G^1$ is —S(=O)$_2$—$CH_3$.

55. A compound according to claim 1 which exhibits activity toward the cannabinoid receptors.

56. A compound according to claim 1 selected from the group consisting of:
N-(4-{3'-[(3-ethylureido)-methyl]-2-hydroxybiphenyl-4-yl}-4-methylpentyl)-2,2-dimethylpropionamide;
2-amino-N-(4-(3'-((3-ethylureido)methyl)-2-hydroxybiphenyl-4-yl)-4-methylpentyl)-2-methylpropanamide;
N-(4-(3'-((3-ethylureido)-methyl)-2-methoxybiphenyl-4-yl)-4-methylpentyl)-pivalamide;
or a pharmaceutically acceptable salt thereof.

57. A pharmaceutical composition comprising a pharmaceutically acceptable carrier and a compound according to claim 1.

58. A pharmaceutical composition according to claim 57, further comprising at least one cannabinoid.

59. A pharmaceutical composition according to claim 58, wherein the cannabinoid is $\Delta^9$-tetrahydrocannabinol or cannabidiol.

60. A pharmaceutical composition according to claim 57, further comprising at least one opioid.

61. A pharmaceutical composition according to claim 60, wherein said opioid is selected from the group consisting of alfentanil, buprenorphine, butorphanol, codeine, dezocine, dihydrocodeine, fentanyl, hydrocodone, hydromorphone, levorphanol, loperamide, meperidine (pethidine), methadone, morphine, nalbuphine, oxycodone, oxymorphone, pentazocine, propiram, propoxyphene, sufentanil and tramadol, and mixtures thereof.

62. A pharmaceutical composition according to claim 57, further comprising at least one analgesic.

63. A pharmaceutical composition according to claim 62, wherein the analgesic is a COX2 inhibitor, aspirin, acetaminophen, ibuprophen, or naproxen, or a mixture thereof.

64. A pharmaceutical composition according to claim 57, further comprising at least one agent selected from the group consisting of an anti seizure agent, an anti-depressant, an NMDA receptor antagonist, an ion channel antagonist, a nicotinic receptor agonist, an anti-Parkinson's agent, and mixtures thereof.

65. A pharmaceutical composition according to claim 64 wherein said anti-seizure agent is carbamazepine, gabapentin, lamotrigine, or phenytoin, or a mixture thereof.

66. A pharmaceutical composition according to claim 64 wherein said anti-depressant is amitryptiline.

67. A pharmaceutical composition according to claim 64, wherein said antiParkinson's agent is deprenyl, amantadine, levodopa, or carbidopa, or a mixture thereof.

68. A compound according to claim 1, wherein each $G^1$ is independently —S(=O)$_2$$R^{19}$, —S(=O)$_2$N($R^{20a}$)($R^{20b}$), —C(=O)-heterocycloalkyl, —C(=O)-heteroaryl, —C(=O)—N($R^{18c}$)($R^{18d}$), or —C(=N—CN)—N($R^{18e}$)($R^{18f}$).

69. A compound according to claim 1, each $R^{17}$ is independently H or alkyl.

70. A compound according to claim 1, $R^{21}$ is H or lower alkyl.

71. A compound according to claim 56 which is N-(4-{3'-[(3-ethylureido)-methyl]-2-hydroxybiphenyl-4-yl}-4-methylpentyl)-2,2-dimethylpropionamide or a pharmaceutically acceptable salt thereof.

72. A compound according to claim 56 which is 2-amino-N-(4-(3'-((3-ethylureido)methyl)-2-hydroxybiphenyl-4-yl)-4-methylpentyl)-2-methylpropanamide or a pharmaceutically acceptable salt thereof.

73. A compound according to claim 56 which is N-(4-(3'-((3-ethylureido)-methyl)-2-methoxybiphenyl-4-yl)-4-methylpentyl)-pivalamide or a pharmaceutically acceptable salt thereof.

* * * * *